(12) United States Patent
Loibner et al.

(10) Patent No.: US 9,777,068 B2
(45) Date of Patent: Oct. 3, 2017

(54) METHOD FOR TREATING A GD2 POSITIVE CANCER

(75) Inventors: Hans Loibner, Vienna (AT); Manfred Schuster, Vienna (AT); Evelyne Janzek-Hawlat, Vienna (AT); Susanne Wiederkum, Stubenberg am See (AT); Bernhard Peball, Vienna (AT); Stefan Stranner, Vienna (AT); Oliver Mutschlechner, Wiener Neudorf (AT); Franz Groiss, Langenzersdorf (AT); Ruth Ladenstein, Vienna (AT); Holger Lode, Greifswald (DE)

(73) Assignee: APEIRON BIOLOGICS AG, Vienna (AT)

( * ) Notice: Subject to any disclaimer, the term of this patent is extended or adjusted under 35 U.S.C. 154(b) by 0 days.

(21) Appl. No.: 14/409,161

(22) PCT Filed: Jul. 31, 2012

(86) PCT No.: PCT/EP2012/064970
§ 371 (c)(1),
(2), (4) Date: Dec. 18, 2014

(87) PCT Pub. No.: WO2013/189554
PCT Pub. Date: Dec. 27, 2013

(65) Prior Publication Data
US 2015/0139942 A1 May 21, 2015

Related U.S. Application Data

(63) Continuation-in-part of application No. PCT/EP2012/061618, filed on Jun. 18, 2012.

(51) Int. Cl.
*C07K 16/30* (2006.01)
*A61K 39/395* (2006.01)
*A61K 31/485* (2006.01)
*A61K 45/06* (2006.01)
*A61K 39/00* (2006.01)

(52) U.S. Cl.
CPC ........ *C07K 16/3084* (2013.01); *A61K 31/485* (2013.01); *A61K 39/39558* (2013.01); *A61K 45/06* (2013.01); *A61K 2039/505* (2013.01); *A61K 2039/54* (2013.01); *A61K 2039/545* (2013.01); *C07K 2317/24* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,833,525 B2 | 11/2010 | Shenoy et al. | |
| 2014/0170155 A1 | 6/2014 | Loibner et al. | |
| 2015/0139942 A1 | 5/2015 | Loibner et al. | 424/85.2 |

FOREIGN PATENT DOCUMENTS

| | | |
|---|---|---|
| JP | 2006521085 | 9/2006 |
| WO | WO 2005/070967 | 8/2005 |
| WO | WO 2008/049643 | 5/2008 |
| WO | WO2008049643 | * 5/2008 |
| WO | WO 2011/160119 | 12/2011 |
| WO | WO 2013/189516 | 12/2013 |
| WO | WO 2013/189554 | 12/2013 |

OTHER PUBLICATIONS

Murray et al, JCO Jan. 1994 vol. 12 No. 1 184-193, abstract.*
Murray et al, J Clin Oncl 12:184-193, 1994, #C2 of IDS dated Dec. 18, 2014.*
Ozkaynak et al, J Clin Oncol 18:4077-85, 2000, #C6 of IDS dated Sep. 2, 2015.*
Yu et al, N. Eng J Med 363:1324-34, 2010, #C3 of IDS dated Dec. 18, 2014.*
Lode et al, Kinderkrebsinfo, DE, clinical trial, publication Apr. 11, 2012.*
Gilman, A.L. et al: "Phase I Study of ch14.18 With Granulocyte-Macrophage Colony-Stimulating Factor and Interleukin-2 in Children With Neuroblastoma After Autologous Bone Marrow Transplantation or Stem-Cell Rescue: A Report From the Children's Oncology Group", Journal of Clinical Oncology, vol. 27, No. 1, (Nov. 24, 2008), pp. 85-91.
Beckman et al.: "Antibody Constructs in Cancer Therapy", Cancer, vol. 109, No. 2, (Jan. 15, 2007), pp. 170-179.
Cespedes et al.: "Mouse models in oncogenesis and cancer therapy", Clin. Transl. Oncol., 8(5), (2006), pp. 318-329.
Dennis: "Off by a whisker", Nature Publishing Group, 442, (2006), pp. 739-741.
Fujimori et al.: "A Modeling Analysis of Monoclonal Antibody Percolation Through Tumors: A Binding-Site Barrier", Journal of Nuclear Medicine, 31, (1990), pp. 1191-1198.
Ozkaynak, M. F.: "Phase I study of chimeric human/murine antiganglioside GD2 monoclonal antibody (ch14.18) with granulocyte-macrophage colony-stimulating factor in children with neuroblastoma immediately after hematopoietic stem-cell transplantation: A Children's Cancer Group study", Journal of Clinical Oncology, American Society of Clinical Oncology, US, vol. 18, No. 24, (Dec. 15, 2000), pp. 4077-4085.
Rudnick et al.: "Affinity and Avidity in Antibody-Based Tumor Targeting", Cancer Biotherapy and Radiopharmaceuticals, vol. 24, No. 2, (Nov. 2, 2009), pp. 155-162.
Talmadge et al.: "Murine Models to Evaluate Novel and Conventional Therapeutic Strategies for Cancer", American Journal of Pathology, vol. 170, No. 3, (Mar. 2007), pp. 793-804.

(Continued)

*Primary Examiner* — Lei Yao
(74) *Attorney, Agent, or Firm* — Norton Rose Fulbright US LLP

(57) ABSTRACT

The present invention relates to a method for treating a GD2 positive cancer by administering a preparation comprising an anti-GD2 antibody to a patient as a continuous intravenous infusion over 24 hours per day.

19 Claims, 17 Drawing Sheets

(56) References Cited

OTHER PUBLICATIONS

Thurber et al.: "Antibody tumor penetration: Transport opposed by systemic and antigen-mediated clearance", Advance Drug Delivery Reviews, 60, (2008), pp. 1421-1434.
Vriesendorp et al.: "Preclinical analysis of radiolabeled anti-GD2 immunoglobulin G.", Cancer 18(12 Suppl), (1997), pp. 2642-2649.
Kowalczyk A. et al.: "The GD2-specific 14G2a monoclonal antibody induce apoptosis and enhances cytotoxicity of chemotherapeautic drugs in IMR-32 human neuroblastoma cells", Cancer Letters, vol. 281, (2009), pp. 171-182.
Mujoo, K. et al.: "Functional Properties and Effect on Growth Suppression of Human Neuroblastoma Tumors by Isotype Switch Variants of Monoclonal Antiganglioside GD2 Antibody 14.18[1]", Cancer Research, vol. 49, (1989), pp. 2857-2861.
Raffaghello, L. et al.: "Anti-GD2 monoclonal antibody immunotherapy: a promising strategy in the prevention of neuroblastoma relapse", Cancer Letters, vol. 197, (2003), pp. 205-209.
Voskoglou-Nomikos, T. et al.: "Clinical Predictive Value of the in Vitro Cell Line, Human Xenograft, and Mouse Allograft Preclinical Cancer Models1", Clinical Cancer Research, vol. 9, (2003), pp. 4227-4239.
Lode, H and Dobke, J.: "A Phase I/II Dose Schedule Finding Study of ch14.18/CHO Continuous Infusion Combined with Subcutaneous Aldesleukin (=Proleukin) (IL-2) in Patients with Primary Refractory or Relapsed Neuroblastoma. A SIOPEN Study", Jun. 13, 2012 (Jun. 13, 2012), pp. 1-3 Retrieved from the Internet: URL:http://www.kinderkrebsinfo.de/health_professionals/clinical_trials/phase_i_ii_trials_in_the_gpoh/longterminfusion_study_lti_ch1418/index_eng.html [retrieved on Dec. 10, 2012].
Murray, James L. et al: "Phase I trial of murine monoclonal antibody 14G2a administered by prolonged intravenous infusion in patients with neuroectodermal tumors", *Journal of Clinical Oncology*, vol. 12, No. 1, 1994, pp. 184-193.
Yu, Alice L. et al: "Anti-GD2 Antibody with GM-CSF, Interleukin-2, and Isotretinoin for Neuroblastoma", *New England Journal of Medicine*, vol. 363, No. 14, Sep. 30, 2010 (Sep. 30, 2010), pp. 1324-1334.
Yu, Alice L. et al: "Phase I trial of a human-Mouse chimeric antidisialoganglioside monoclonal antibody ch14.18 in patients with refractory neuroblastoma and osteosarcoma", *Journal of Clinical Oncology, American Society of Clinical Oncology*, US, vol. 16, No. 6, Jun. 1, 1998 (Jun. 1, 1998), pp. 2169-2180.
Saleh, Mansoor N. et al.: "Phase I Trial of the Murine Monoclonal Anti-GD-2 Antibody 14G2A in Metastatic Melanoma", *Cancer Research*, vol. 52, No. 16, 1992, pp. 4342-4347.
Frost, Jami D. et al: "A Phase 1/IB trial of murine monoclonal anti-GD2 antibody 14.G2a plus interleukin-2 in children with refractory neuroblastoma", *Cancer*, vol. 80, No. 2, Jul. 15, 1997 (Jul. 15, 1997), pp. 317-333.
Handgretinger, R. et al.: "A phase I study of human/mouse chimeric antiganglioside GD2 antibody ch14.18 in patients with neuroblastoma", *European Journal of Cancer*, vol. 31, No. 2, Jan. 1, 1995 (Jan. 1, 1995), pp. 261-267.
Handgretinger, Rupert et al: "A phase I study of neuroblastoma with the anti-ganglioside GD2 antibody 14.G2a", *Cancer Immunology and Immunotherapy*, Springerverlag, Berlin, DE, vol. 35, No. 3, Jan. 1, 1992 (Jan. 1, 1992), pp. 199-204.
Navid, F. et al: "Anti-GD2 antibody therapy for GD2-expressing tumors.", *Current Cancer Drug Targets* Mar. 2010, vol. 10, No. 2, Mar. 2010 (201 0-03), pp. 200-209.
Chames, Patrick et al.: "Bispecific antibodies for cancer therapy the light at the end of the tunnel?", *MABS*, val. 1, No. 6, Nov. 2009 (Nov. 2009), pp. 539-547.
Mueller, Barbara M. et al: "Enhancement of Antibody-Dependent Cytotoxicity With a Chimeric Anti-GD2 Antibody", *The Journal of Immunology, The American Association of Immunologists*, US, vol. 144, No. 4, Feb. 15, 1990 (Feb. 15, 1990), pp. 1382-1386.
Batova, Ayse et al: "The CH14.18-GM-CSF Fusion Protein Is Effective At Mediating Antibody-Dependent Cellular Cytotoxicity and Complement-Dependent Cytotoxicity in Vitro", *Clinical Cancer Research, The American Association for Cancer Research*, US, vol. 5, No. 12, Dec. 1, 1999 (Dec. 1, 1999), pp. 4259-4263.
Shusterman, Suzanne S. et al: "Antitumor Activity of Hu14.18-IL2 in Patients With Relapsed/Refractory Neuroblastoma: A Children's Oncology Group (COG) Phase II Study", *Journal of Clinical Oncology*, Oct. 2010, pp. 1-10.
Idusogie et al., "Mapping of the C1q binding site on rituxan, a chimeric antibody with a human IgG1 Fc", *J. Immunol.*, 164(8):4178-4184, 2000.
International Search Report & Written Opinion issued in PCT Appl No. PCT/EP2012/064970, dated Jan. 11, 2013.
International Search Report issued in PCT Appl No. PCT/EP2012/061618, dated Jan. 7, 2013.
Zeng et al., "Anti-neuroblastoma effect of ch14.18 antibody produced in CHO cells is mediated by NK-cells in mice", *Molecular Immunology*, 42(11):1311-1319, 2005.
"High Risk Neuroblastoma Study 1 of SIOP-Europe (SIOPEN)", SIOP, Jul. 1, 2009, pp. 1-303, Retrieved from the Internet: URL:http://www.oncauvergne.fr/index.php?option=com_docman&task=doc_download&gid=928&Itemid= [retrieved on Mar. 27, 2014].
"Press Release: Oncology Alliance. Apeiron, CCRI and SIOPEN Join Forces against Neuroblastoma", Apeiron Biologics AG., Jun. 2011, 8 pages. Vienna. Retrieved from the internet: URL:http://www.life-sciences-germany.com/news/apeiron-ccri-siopen-neuroblastoma-biologics-group-forschung-und-2001-97329.html [retrieved on Mar. 20, 2014].
Balwierz et al., "Treatment results of children with neuroblastoma: report of Polish Pediatric Solid Tumor Group", Przegl Lek, 67: 387-92, 2010. (Abstract provided).
Castel et al., "Treatment of high-risk neuroblastoma with anti-GD2 antibodies", Clinical and Translational Oncology, 12(12): 788-793, 2010.
Drozynska et al., "Initial results of the treatment of six patients with high risk neuroblastoma in the years 2002-2006", Med Wieku Rozwoj, 11(3 pt 2): 325-30, 2011. (Abstract provided).
Gains et al., "Ten challenges in the management of neuroblastoma", Future Oncology, 8(7): 839-858, 2012.
Kushner et al., "Phase II trial of the anti-GD2 monoclonal antibody 3F8 and granulocyte-macrophage colony-stimulating factor for neuroblastoma", Journal of Clinical Oncology, 19(22): 4189-4194, 2001.
Lode et al., "Long-term continuous infusion of anti-GD2 antibody CH14.18/CHO in relapsed/refractory neuroblastoma patients", Journal for ImmunoTherapy of Cancer, 1(Suppl 1): 244, 2013.
Office Action issued in European Patent Application No. 13193953. 0, dated Apr. 16, 2014.
Simon, "Consolidation Treatment With Chimeric Anti-GD2-Antibody ch14. 18 in Children Older than 1 Year With Metastatic Neuroblastoma", Journal of Clinical Oncology, 22(17): 3549-3557, 2004.
Simon et al.: Long Term Outcome of High-Risk Neuroblastoma Patients After Immunotherapy With Antibody Ch14.18 or Oral Metronomic Chemotherapy, BMC Cancer, (2011), 11:21, pp. 1-8.
Cheung et al, "Humanizing murine IgG3 anti-GD2 antibody m3F8 substantially improves antibody-dependent cell-mediated cytotoxicity while retaining targeting in vivo," *Oncolmmunology*, 1.4, (Jul. 2012): 447-486).
Lode et al. "Long-term continuous infusion of anti-GD2 antibody CH14.18/CHO in relapsed/refractory neuroblastoma patients", *Journal for ImmunoTherapy of Cancer*, 1 (Suppl. 1): 244, 2013.
NCT00072358, "Phase II Study of Anti-GD2 3F8 Antibody nd GM-CSF for High-Risk Neuroblastoma," *ClinicalTrials.gov archive*, version Jul. 8, 2013.

\* cited by examiner

Morphine dose reduction in continuous versus non-continuous infusion

| morphine application | SIOPEN phase I trial (n = 16) | continuous infusion pilot (n = 37) |
|---|---|---|
| starting infusion rate | 50 μg/kg KG/h | 30 μg/kg KG/h |
| additional application (bolus) | 63% | 14% |
| dose increase | 50% | 16% |

Fig. 17

METHOD FOR TREATING A GD2 POSITIVE CANCER

CROSS-REFERENCE TO RELATED APPLICATIONS

This application is a national phase application under 35 U.S.C. §371 of International Application No. PCT/EP2012/064970 filed 31 Jul. 2102, which claims priority to International Application No. PCT/EP2102/061618 filed 18 Jun. 2012. The entire contents of each of the above-referenced disclosures is specifically incorporated by reference herein without disclaimer.

FIELD OF THE INVENTION

The present invention relates to a method for treating a GD2 positive cancer by administering a preparation comprising an anti-GD2 antibody to a patient as a continuous intravenous infusion over 24 hours per day.

BACKGROUND TO THE INVENTION

Neuroblastoma, after brain cancer, is the most frequent solid cancer in children under five years of age. In high-risk neuroblastoma, more than half of the patients receiving standard therapy have a relapse and ultimately die from the disease. 90% of cases occur between ages zero to six. The worldwide incidence in industrialized countries is around 2000 cases per year.

Monoclonal antibodies against specific antigens are increasingly being used in oncology. The entirely different mode of action compared to cytotoxic therapies have made them a valuable asset as is shown by forerunners like trastuzumab, cetuximab, bevacizumab, rituximab and others. The disialoganglioside GD2 is a glycosphingolipid expressed primarily on the cell surface. GD2 expression in normal tissues is rare and primarily restricted to the central nervous system (CNS), peripheral nerves and melanocytes. In cancerous cells, GD2 is uniformly expressed in neuroblastomas and most melanomas and to a variable degree in bone and soft-tissue sarcomas, small cell lung cancer, renal cell carcinoma, and brain tumors (Navid et al., Curr Cancer Drug Targets 2010). Because of the relatively tumor-selective expression combined with its presence on the cell surface, GD2 represents a promising target for antibody-based cancer immunotherapy.

Accordingly, several anti-GD2 antibodies are subject to preclinical or clinical investigation in neuroblastoma, melanoma and other GD2-related cancers.

APN311 is a formulation of the chimeric monoclonal anti-GD2 antibody ch14.18 recombinantly produced in Chinese hamster ovary (CHO) cells, which is the standard mammalian cell line for production of commercially available antibodies. In a Phase I clinical study in relapsed/refractory neuroblastoma patients remissions were achieved with this antibody as single agent. A Phase III trial comprising treatment with APN311 was initiated in 2006 by the International Society of Paediatric Oncology European Neuroblastoma (SIOPEN) and is presently investigating the effects on event-free and overall survival related to treatment with APN311 together with isotretinoin, i.e. cis-retinoic acid (cis-RA), with or without s.c. IL-2. In a comparable US study using a treatment package of 4 drugs, namely a related antibody produced in SP2/0 murine hybridoma cells together with i.v. Interleukin-2 (IL-2), Granulocyte-macrophage colony-stimulating factor (GM-CSF) and isotretinoin, interesting survival improvement was seen in children with neuroblastoma in complete remission following initial therapies and no evidence of disease.

APN301 is a formulation of an immunocytokine comprising a humanized anti-GD2 antibody (hu14.18) and IL-2 as a fusion protein. The antibody portion specifically binds to the GD2 antigen that is strongly expressed on neuroblastoma and several other cancers. IL-2 is a cytokine that recruits multiple immune effector cell types. In neuroblastoma patients, APN301 is designed to localize GD2-positive tumor cells via the antibody component. The fused IL-2 then stimulates the patient's immune system against the tumor by activation of both, NK and T cells, whereas the Fc portion of the antibody is designed to trigger tumor cell killing by antibody-dependent cellular cytotoxicity (ADCC) and complement-dependent cytotoxicity (CDC). The immunocytokine has shown activity in a Phase II clinical study in children with relapsed/refractory neuroblastoma (Shusterman et al.; JCO 2010) and was also tested in a Phase I/II study in late stage malignant melanoma, showing immune activation.

Other anti-GD2 antibodies in research or development are, for example, the monoclonal antibody 3F8 (murine in phase II, as well as humanized in phase I), and 8B6 (specific to O-acetylated GD2, preclinical). Furthermore, anti-idiotypic antibodies such as e.g. 4B5, 1A7, and A1G4 have been under investigation as potential tumor vaccines, however, their development seems to be abandoned. WO 2008/049643 also describes anti-idiotypic antibodies, which mimic GD2 epitopes, i.e. GD2 mimotopes.

Another version of the 14.18 anti-GD2 antibody is hu14.18K322A as described in WO2005/070967, which has a point mutation in the Fc region in order to reduce CDC, but maintain ADCC, e.g. by expression in a cell line suitable for enhancing ADCC, such as YB2/0. The reduction in CDC is considered to result in reduced pain associated with the antibody treatment.

Anti-tumor activity of antibodies generally occurs via either complement dependent cytotoxicity (CDC or complement fixation) or through anti-body dependent cell-mediated cytotoxicity (ADCC). These two activities are known in the art as "effector functions" and are mediated by antibodies, particularly of the IgG class. All of the IgG subclasses except IgG4 (IgG1, IgG2, IgG3) mediate ADCC and complement fixation to some extent, with IgG1 and IgG3 being most potent for both activities. ADCC is believed to occur when Fc receptors on natural killer (NK) cells and/or other Fc receptor bearing immune cells (effector cells) bind to the Fc region of antibodies bound to antigen on a cell's surface. Fc receptor binding signals the effector cell to kill the target cell. CDC is believed to occur by multiple mechanisms; one mechanism is initiated when an antibody binds to an antigen on a cell's surface. Once the antigen-antibody complex is formed, the C1q molecule is believed to bind the antigen-antibody complex. C1q then cleaves itself to initiate a cascade of enzymatic activation and cleavage of other complement proteins, which then bind the target cell surface and facilitate its death through, for example, cell lysis and/or ingestion by macrophages.

However, CDC is considered to cause the side effect of pain, especially for anti-GD2 antibodies. As described in WO2005/070967, neurons may be particularly sensitive to complement fixation because this process involves the creation of channels in a cell membrane, allowing an uncontrolled ion flux. In pain-sensing neurons, even a small amount of complement fixation may be significant to generate action potentials. Thus, any amount of CDC resulting from anti-GD2 antibody binding on neurons will result in pain.

Accordingly, the prior art teaches that it is advantageous to reduce complement fixation so as to reduce the level of side effects in a patient and that the antitumor activity of anti-GD2 antibodies results primarily from ADCC, and not substantially from complement fixation (see e.g. WO2005/070967).

In contrast, a key aspect of the invention is that the cytolysis capacity of an anti-GD2 antibody determined by a CDC assay or a whole blood test (WBT) is essential for the anti-tumor effect of the anti-GD2 antibody. Such a WBT assay in contrast to CDC or ADCC assays measures the lytic potential of a heparinized whole blood sample. Thus, it does not only focus on one single effector mechanism but measures a combination of ADCC and CDC (and any other components and/or mechanisms present in the heparinized whole blood sample which might also be relevant to the lytic capacity against tumor cells) in a physiological setting. Accordingly, with the methods of the present invention it is possible to reduce the dose of the antibody to the minimal dose required for target cell lysis as determined by a CDC assay or a WBT. Furthermore, the methods of the invention allow to individually determine the effective antibody dose and thus, take into account the individual differences in anti-tumor responses of the patients. Another key aspect of the invention is that it is possible to reduce and manage the side effect of pain by determining the threshold dose of the anti-GD2 antibody to be administered to induce CDC and/or whole blood cytolytic activity. Another key finding of the invention is that the side effect of pain can be substantially reduced by administering the anti-GD2 antibody as a continuous infusion until the predetermined overall patient dose has been administered. Accordingly, with the methods according to the invention it is possible to substantially reduce the analgesic administration, especially the administration of strong analgesics such as morphine, during the antibody treatment, and thus, also substantially reduce the side effects of such analgesic administration.

BRIEF DESCRIPTION OF THE INVENTION

In one aspect, the present invention relates to a method for treating a GD2 positive cancer by administering a preparation comprising an anti-GD2 antibody to a patient as a continuous intravenous infusion over 24 hours per day. Said preparation comprising an anti-GD2 antibody may be administered by using a mini-pump, and may be administered for a treatment period until the predetermined overall patient dose has been administered.

In another aspect, the present invention relates to a method for treating a GD2 positive cancer by administering a preparation comprising an anti-GD2 antibody to a patient, wherein the preparation is administered in a dose sufficient to induce tumor cell lysis (cytolysis threshold dose), and wherein said cytolysis threshold dose is administered for a treatment period until the predetermined overall patient dose has been administered.

In a related aspect the invention provides an anti-GD2 antibody for use in said treatment. In a further related aspect the invention provides the use of an anti-GD2 antibody in the preparation of a medicament for said treatment. The invention is further defined by the claims. All preferred embodiments of the invention as further described herein relate to all aspects of the invention equally.

BRIEF DESCRIPTION OF THE FIGURES

FIG. 17 shows the initial infusion rate of morphine administered during the antibody infusion in two different schedules (for the SIOPEN phase I trial: 8 h antibody infusion for 5 subsequent days; for the continuous infusion pilot schedule 24 h antibody infusion for 10 subsequent days), as well as the additional morphine administrations (given as a bolus) and the increases in the morphine infusion rate or the morphine dose that were required.

DETAILED DESCRIPTION OF THE INVENTION

It has surprisingly turned out that a treatment with a preparation comprising an anti-GD2 antibody in a dose determined by cytolysis capacity, e.g. either measured by a CDC assay or by a WBT, has a beneficial effect in cancer therapy, especially on side effects such as pain. If the preparation comprising an anti-GD2 antibody is administered in a dose as low as possible but sufficient to induce CDC and/or whole blood cytolysis, and is administered in said cytolysis threshold dose for a treatment period until the predetermined overall patient dose has been administered, pain can be substantially reduced and thus, the administration of morphine or other analgesics can be substantially reduced or even stopped.

In one aspect, the invention concerns a method for treating a GD2 positive cancer by administering a preparation comprising an anti-GD2 antibody to a patient as a continuous intravenous infusion over 24 hours per day. The preparation comprising an anti-GD2 antibody may be administered for a treatment period until the predetermined overall patient dose has been administered.

In another aspect, the invention concerns a method for treating a GD2 positive cancer by administering a preparation comprising an anti-GD2 antibody to a patient, wherein the preparation is administered in a dose sufficient to induce tumor cell lysis (cytolysis threshold dose), and wherein said cytolysis threshold dose is administered until the predetermined overall patient dose has been administered.

In some embodiments, the preparation comprising an anti-GD2 antibody is administered to a patient in a dose sufficient to induce tumor cell lysis (cytolysis threshold dose), and the preparation is administered as a continuous intravenous infusion over 24 hours per day. In other embodiments, the preparation comprising an anti-GD2 antibody is administered to a patient in a dose sufficient to induce tumor cell lysis (cytolysis threshold dose), and the preparation is administered as a continuous intravenous infusion over 24 hours per day, and said cytolysis threshold dose is administered until the predetermined overall patient dose has been administered.

Figure 1:
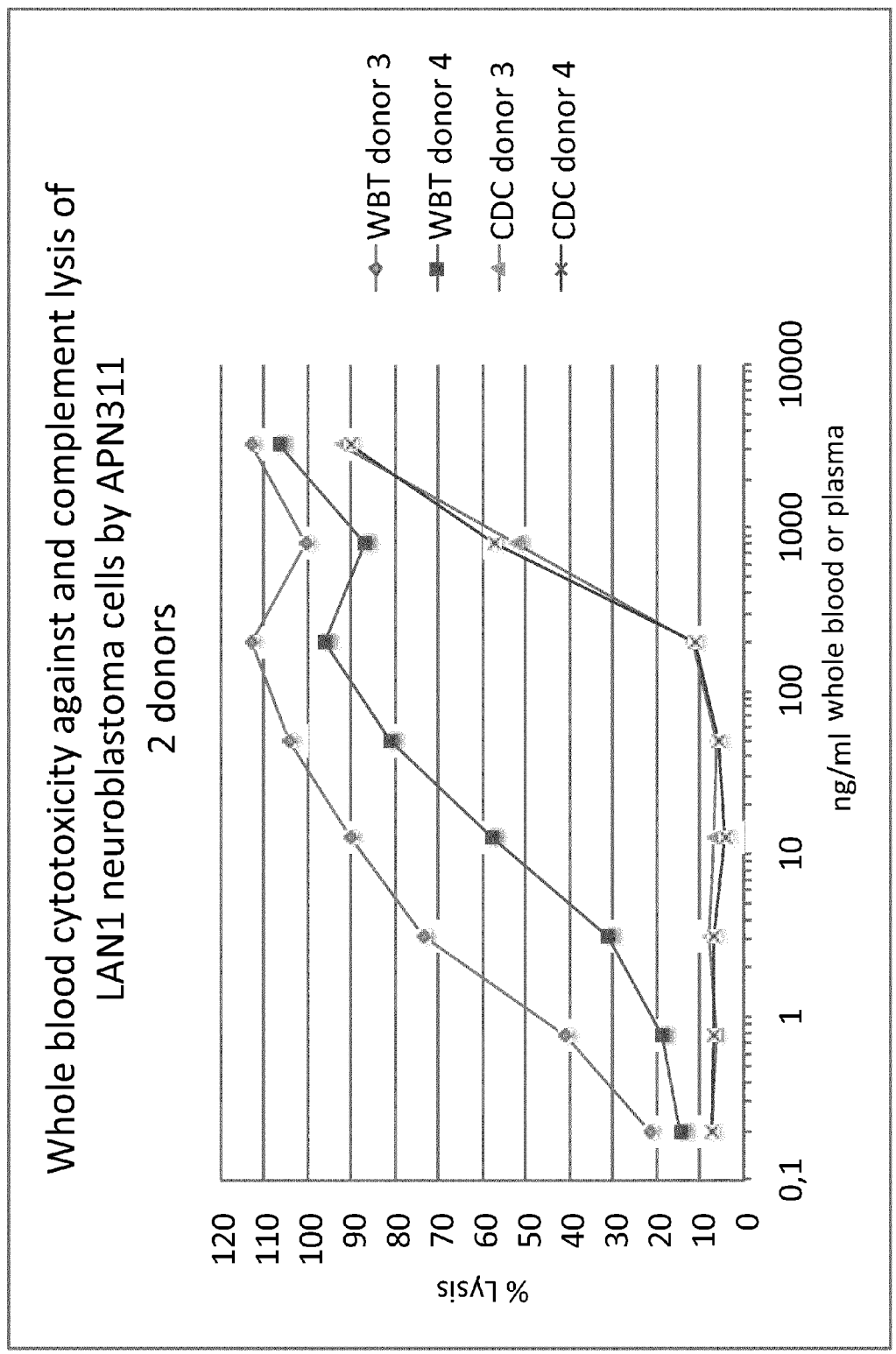
FIG. 1 shows the results of a WBT (with heparinized whole blood, using $^{51}$Cr labeled target human neuroblastoma cells) and a CDC assay (with heparinized plasma, also using $^{51}$Cr labeled target human neuroblastoma cells) of two healthy donors in the presence of APN311. As can be seen, there is a substantial difference in WBT lysis between the two donors: 50% lysis is reached at APN311 concentrations of 2 versus 10 ng/mL whole blood. However, there is no difference in CDC: 50% lysis of both donors is reached at APN311 concentrations of 1000 ng/ml plasma. In both assays (WBT and CDC assay), the same incubation time (20 h) has been used, as well as the same final concentration of complement.
Figure 2:
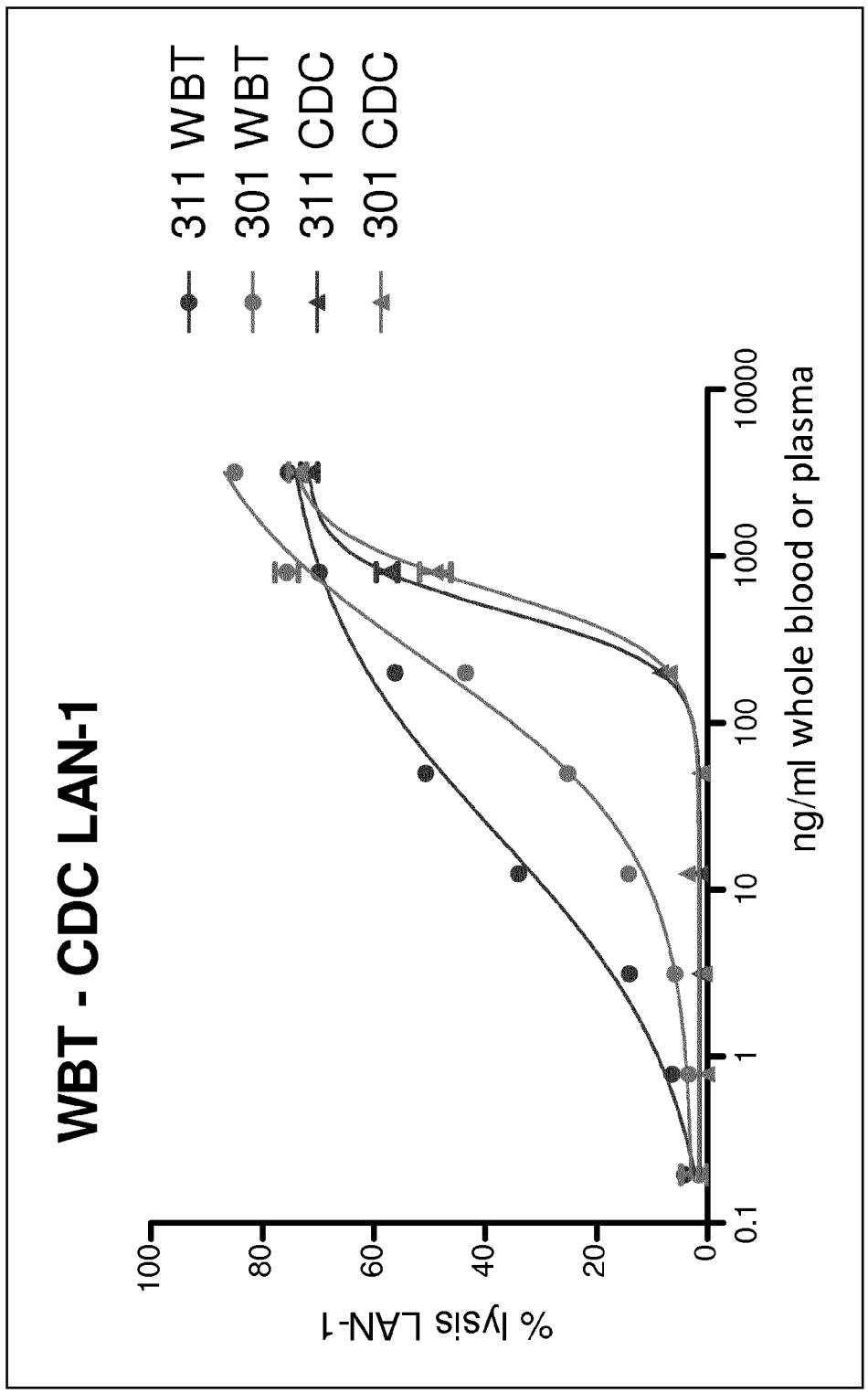
FIG. 2 shows the results of a WBT (with heparinized whole blood, using $^{51}$Cr labeled target human neuroblastoma cells) and a CDC assay (with heparinized plasma, using $^{51}$Cr labeled target human neuroblastoma cells) of one healthy donor in the presence of APN301 or APN311. There is a substantial difference in WBT lysis between the two preparations: 50% lysis is reached at an APN311 concentration of 21 ng/mL whole blood versus an APN301 concentration of 234 ng/mL. However, the difference in CDC is less substantial: 50% lysis is reached at an APN311 concentration of 470 ng/mL plasma versus an APN301 concentration of 619 ng/mL plasma.
Figure 3:
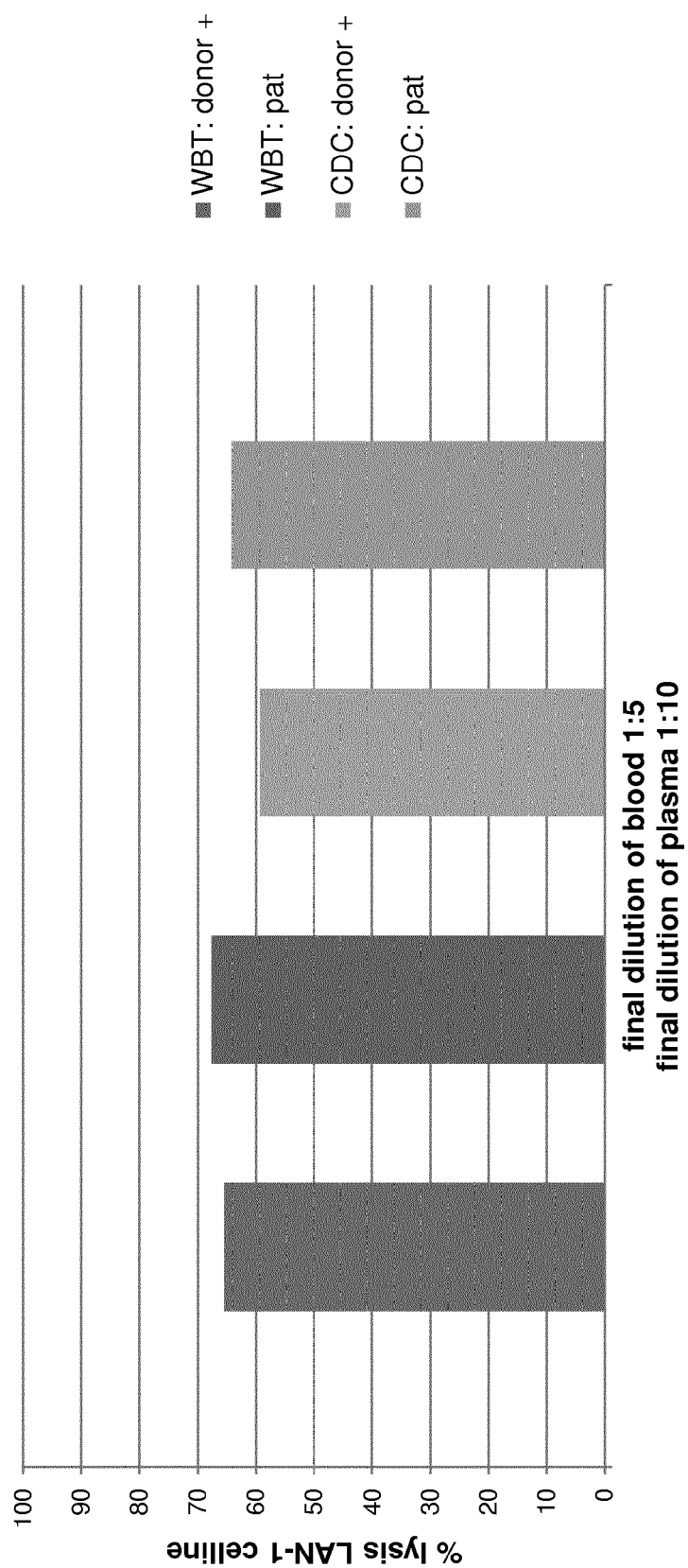
FIG. 3 shows the results of a WBT and CDC assay with whole blood or plasma of a healthy donor spiked with 5 μg/mL APN311 compared to the whole blood or plasma of a patient treated with APN311. The patient sample was collected on day 17 of the treatment cycle, i.e. at the end of the treatment period with APN311, which in this case is from day 8 to 18 of the treatment cycle.
Figure 4:
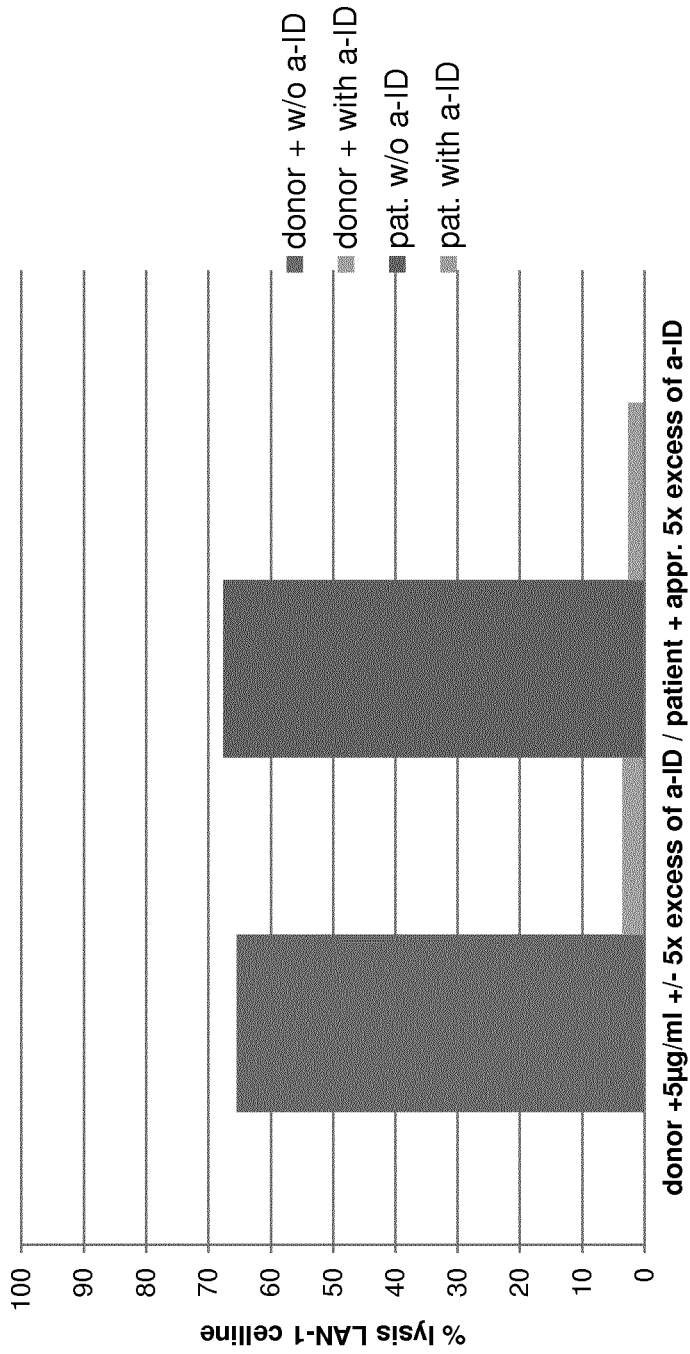
FIG. 4 shows the results of the WBT as shown in FIG. 3 compared to the same samples with the addition of a 5-fold excess of a specific anti-idiotypic (anti-ID) antibody, which inhibits the target cell lysis.
Figure 5:
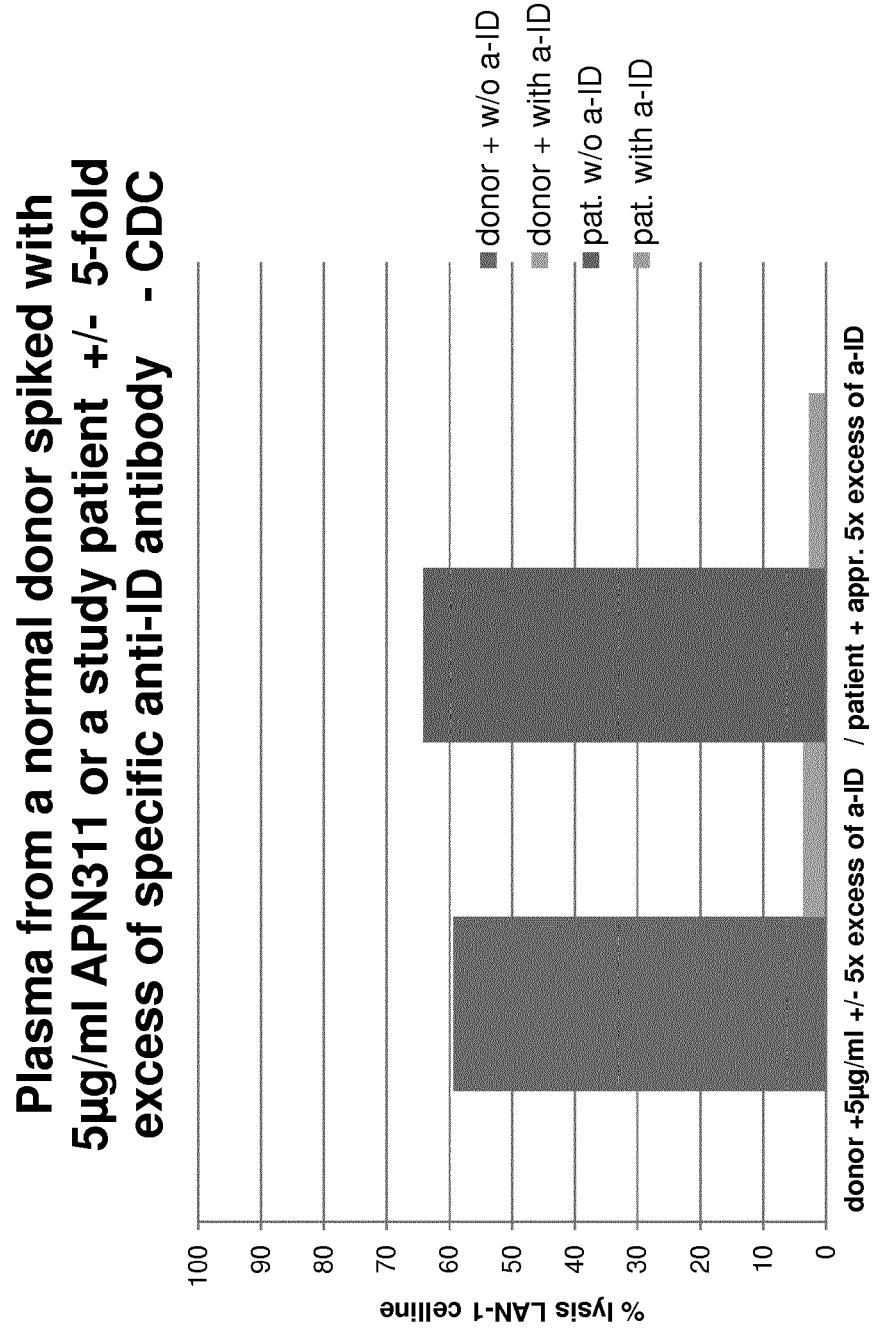
FIG. 5 shows the results of the CDC assay as shown in FIG. 3 compared to the same samples with the addition of a 5-fold excess of specific anti-ID antibody, which inhibits the target cell lysis.
Figure 7:
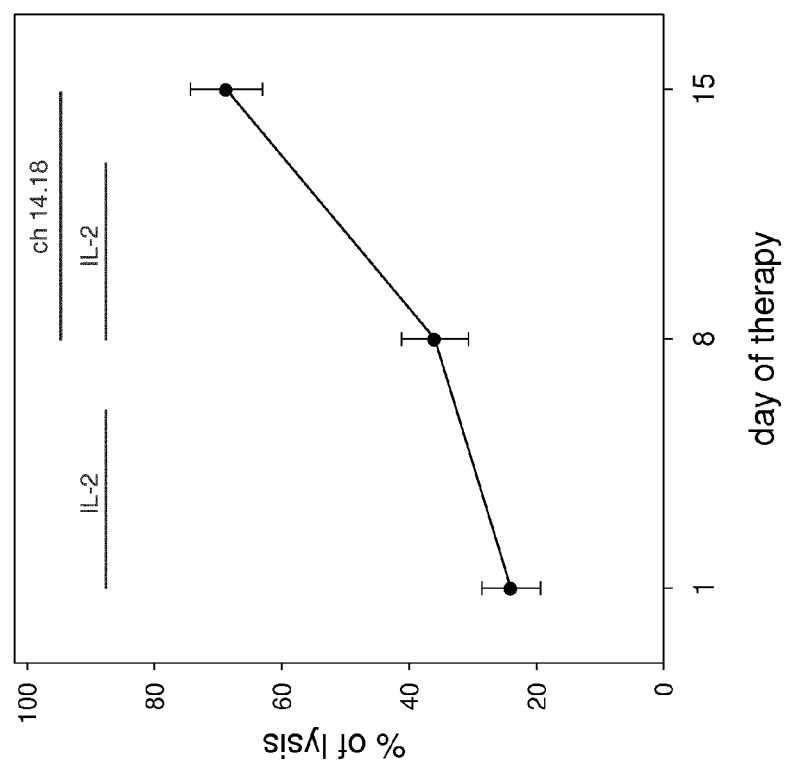
FIG. 7 shows the CDC assay results on day 1, 8, and 15 of the treatment cycle of 37 patients treated with APN311, as measured by a calcein release CDC assay. The treatment period with APN311 was from day 8 to 18, the two treatment periods with IL-2 were on days 1 to 5 and 8 to 12.

In certain embodiments, the cytolysis threshold dose is a therapeutically effective amount of the preparation comprising an anti-GD2 antibody. The therapeutically effective amount may be determined by a CDC assay or a WBT using patient's serum or plasma or heparinized whole blood. In some embodiments, the cytolysis threshold dose is a minimal cytolysis threshold dose, such as e.g. the lowest dose determined to induce a certain level of cytolysis in a CDC assay or a WBT. In one embodiment, the cytolysis threshold dose is the dose determined in a specific CDC assay or WBT to induce 30% of the maximal possible target cell lysis in that respective assay. In certain embodiments, the cytolysis threshold dose is the dose that achieves 35%, 40%, 45%, 50%, 55%, 60%, 65%, 70%, 75%, 80%, 85%, 90%, 95%, 100%, or any range in between these levels, of the maximal possible cell lysis in the respective assay (a specific CDC assay or WBT). For example, as done in Examples 2 and 3 and as shown in FIGS. 1, 2 and 7, several concentrations of the preparation comprising the anti-GD2 antibody are either spiked into the blood or plasma of the donor or already present in the blood or plasma of the patient who has been treated with the preparation comprising an anti-GD2 antibody, to determine a CDC or whole blood lysis curve. By drawing a curve between the measured concentrations of anti-GD2 antibody, the dose or concentration of anti-GD2 antibody achieving a certain threshold cytolysis (e.g. 50% of the maximal possible target cell lysis) can be determined. In the example of FIG. 1, a threshold of 50% cytolysis (e.g. 50% of the maximal possible target cell lysis) is achieved with concentrations of 2 or 10 ng/mL whole blood of the respective donor in the WBT, or with 1000 ng/mL serum or plasma in the CDC assay. In this example, the threshold cytolysis is 50%.

The terms "threshold cytolysis" and/or "level of cytolysis" as used herein means the level of target cell lysis in a specific CDC assay or WBT specified to determine the cytolysis threshold dose in serum, plasma or whole blood in said CDC assay or WBT.

In some embodiments, the threshold cytolysis is maintained even for one or more time periods within the overall treatment time, where the patient is not treated with the preparation comprising an anti-GD2 antibody, i.e. in the intervals between the treatment periods with the preparation comprising an anti-GD2 antibody (if any, i.e. if the patient is not treated continuously over the overall treatment time with the preparation comprising an anti-GD2 antibody). In certain embodiments, the level of cytolysis is maintained over the entire treatment cycle. In some embodiments, the level of cytolysis is maintained over the overall treatment time.

Figure 11:
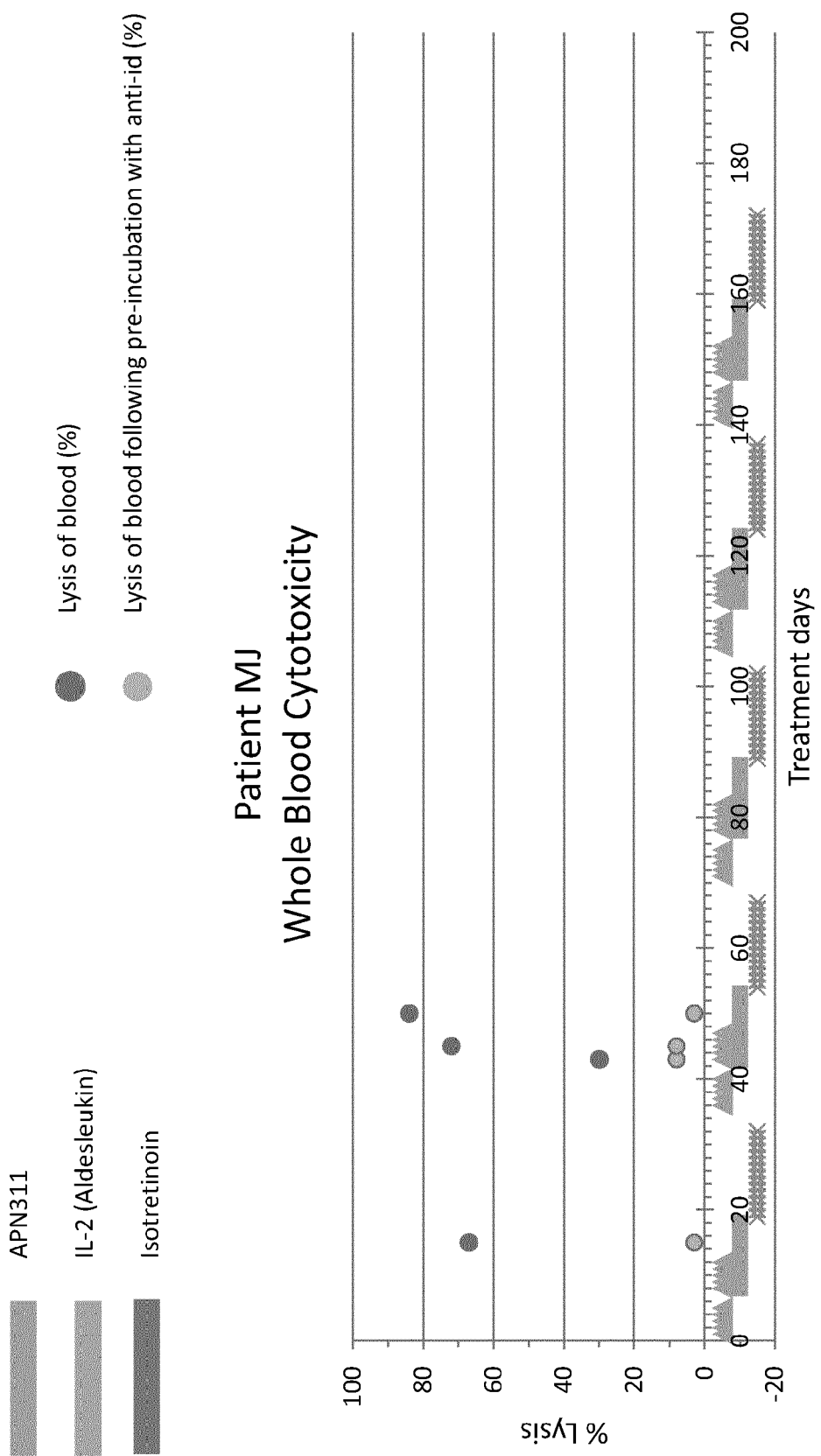
FIGS. 11 to 16 show cytolysis results obtained with blood samples from patients who are in different stages of their treatment cycles. The data are shown in a standardized format that represents the treatment schedule as applied, namely APN311 in a dose of 100 mg/m²/cycle, 10 days continuous infusion by mini-pump, i.v.; aldesleukin (IL2) in a dose of 60×10⁶ IU/m²/cycle, 10 days per cycle, administered in two 5-day periods, in a dose of 6×10⁶ IU/m²/day s.c.; and 13-cis retinoid acid (isotretinoin) in a dose of 2240 mg/m²/cycle, administered for 14 days (once a day) in a dose of 160 mg/m²/day p.o. The overall treatment time comprises 5 cycles comprising 35 days per cycle, and day 36 is the first day of the second treatment cycle. The blood samples taken at the beginning (i.e. on the first day) of the treatment period with APN311 (corresponding to day 8 of the treatment cycle) were taken prior to the start of the APN311 treatment, see also table 8.
Figure 12:
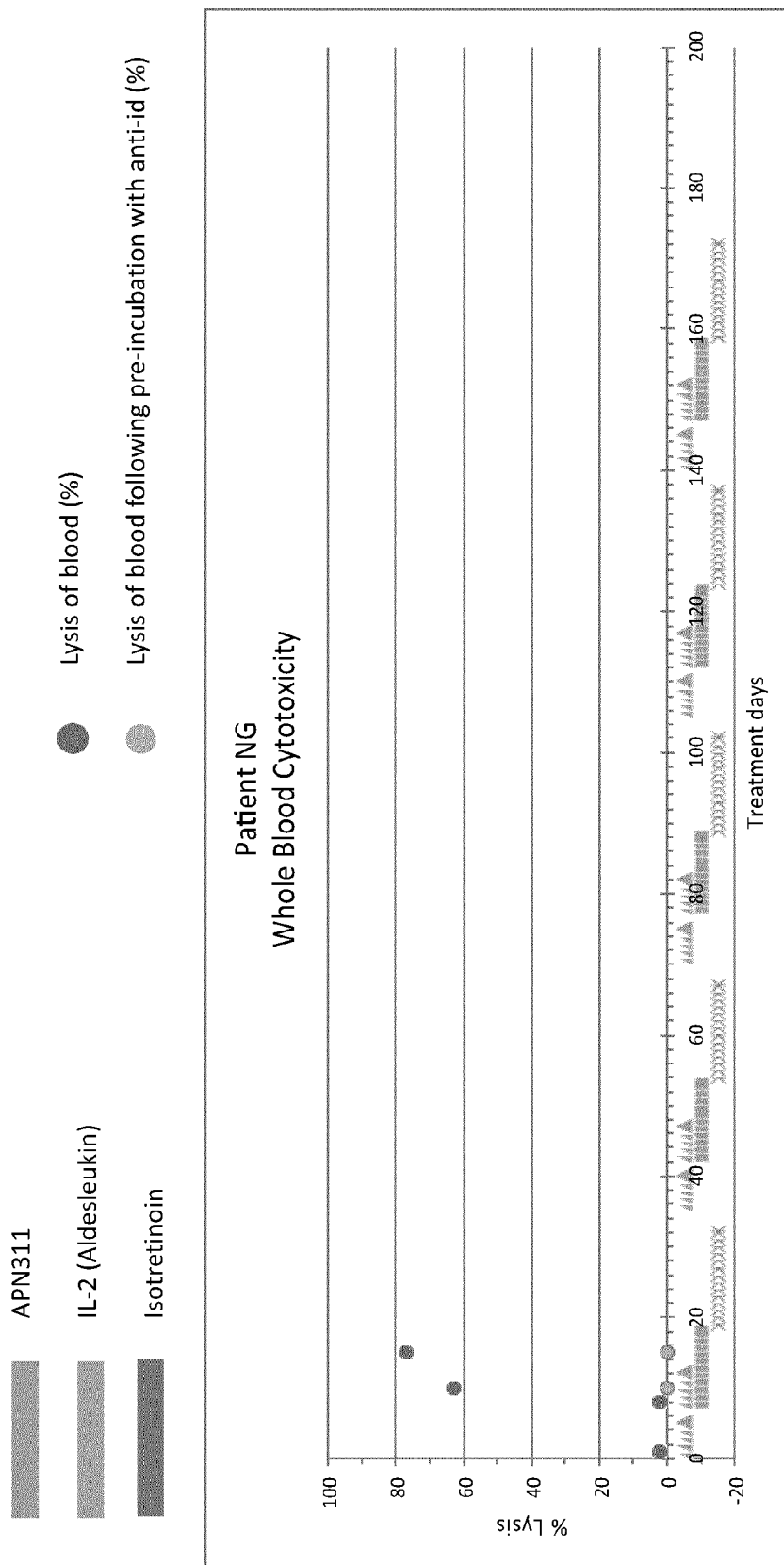
Figure 13:
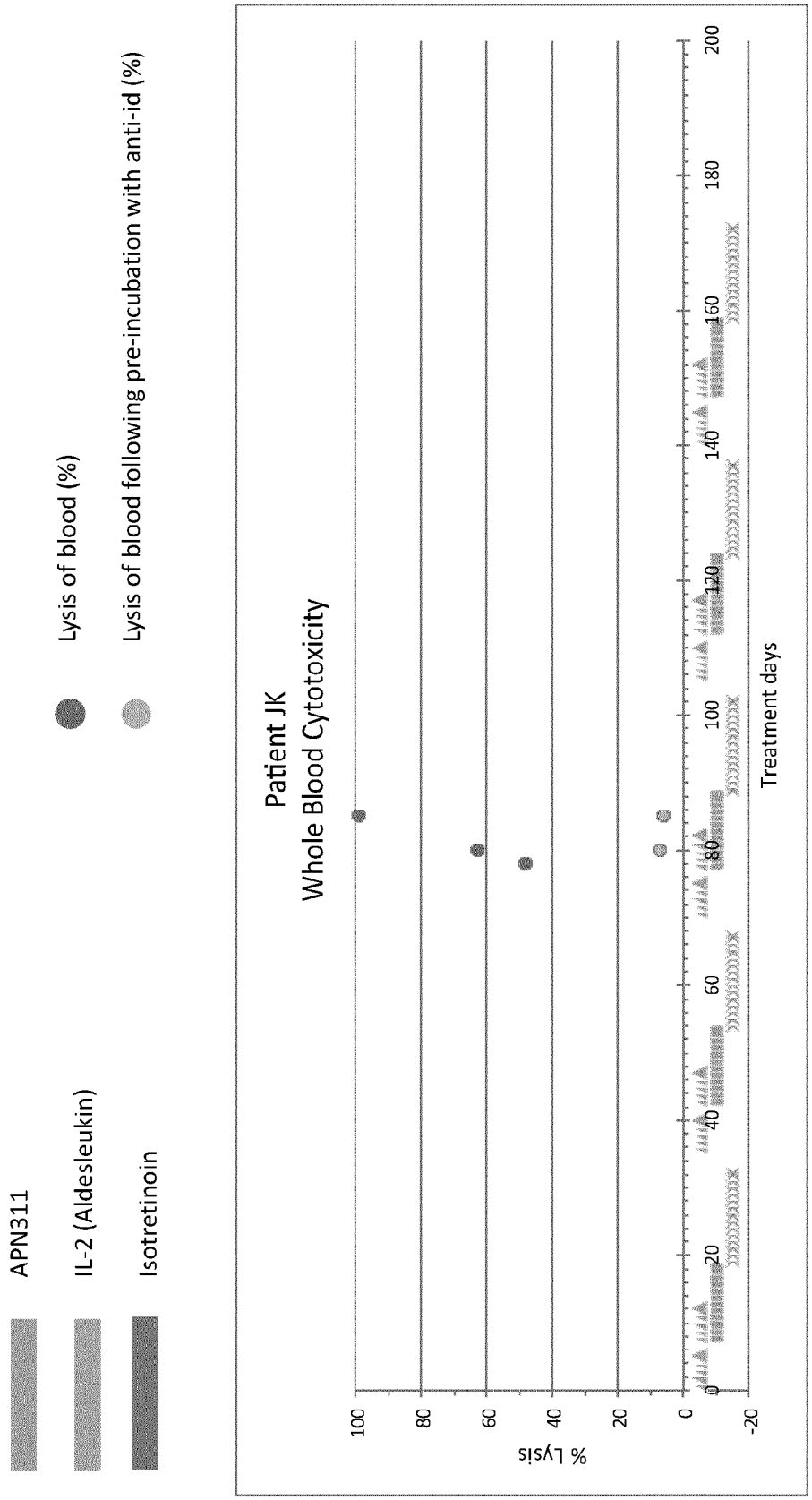
Figure 14:
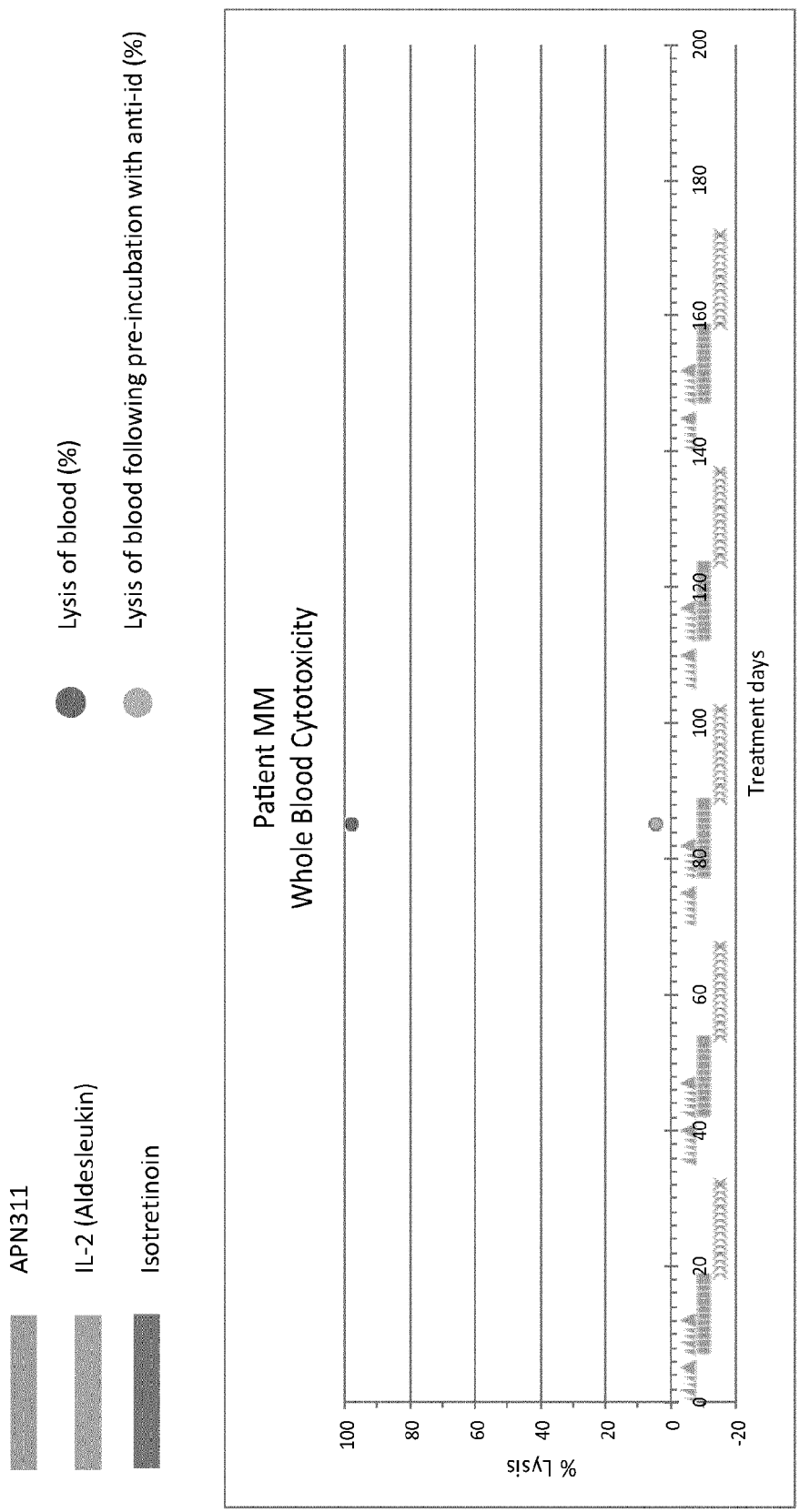
Figure 15:
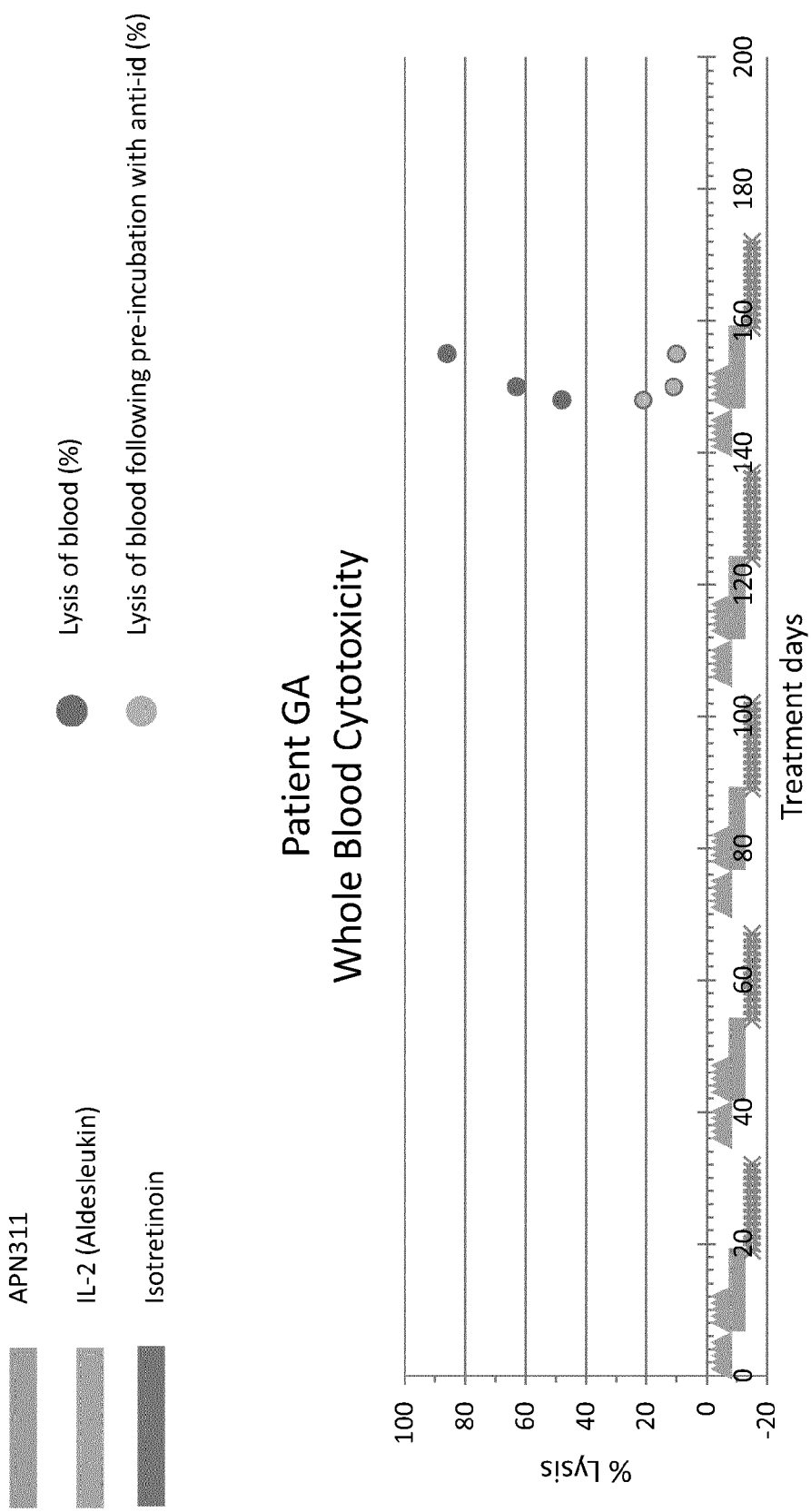
Figure 16:
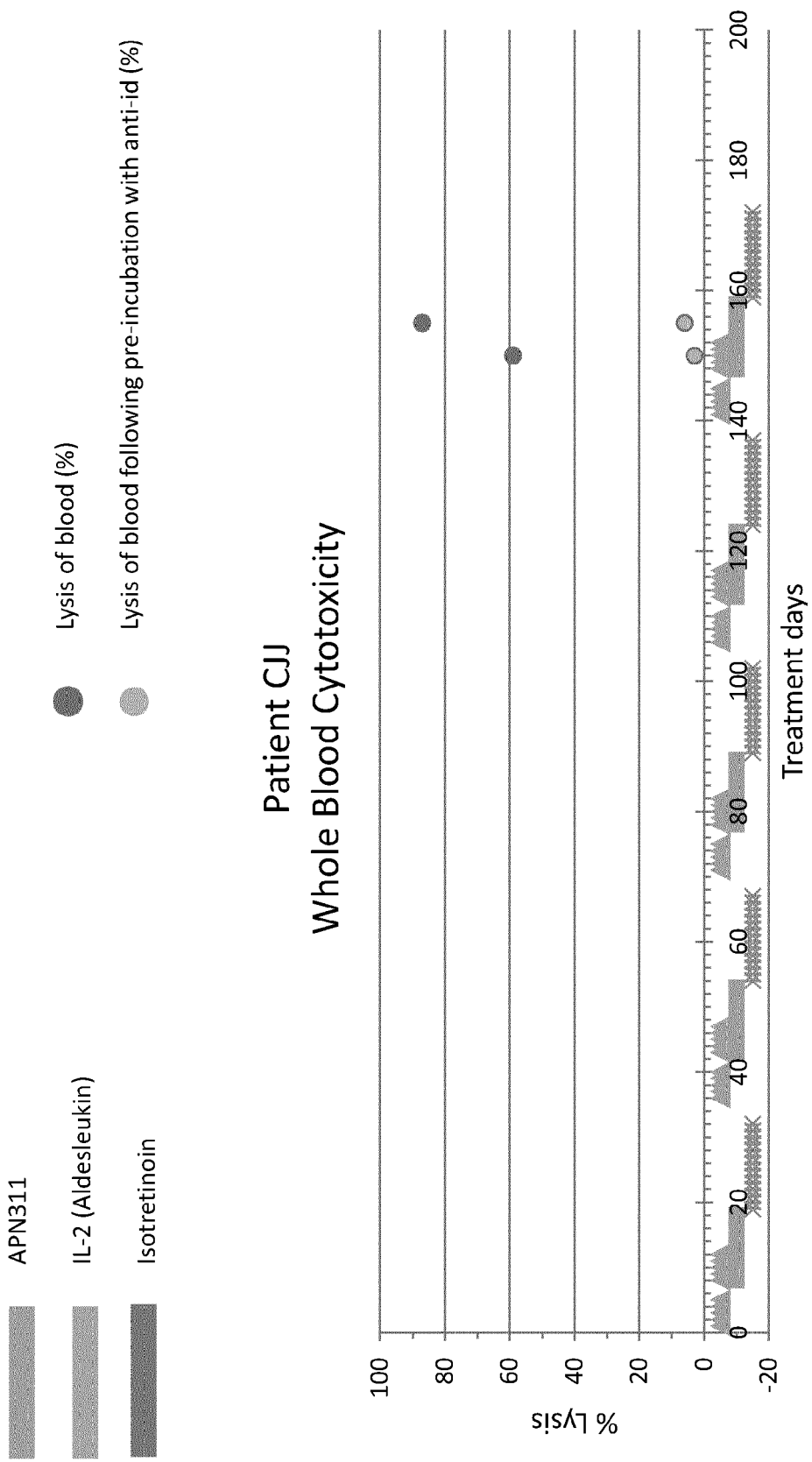

As can be seen in FIGS. 11, 13, and 15, an increased level of cytolysis between 30% and 50% has been maintained even over the interval, where the patients have not been treated with the preparation comprising an anti-GD2 antibody.

In one embodiment, the cytolysis threshold dose is determined individually for each patient.

The term "predetermined overall patient dose" as used herein shall mean the overall patient dose per treatment cycle, as further specified below.

The term "patient" as used herein shall mean an animal or human subject suffering from cancer, especially a GD2 positive cancer.

If a range is given herein, any such range shall include any range in between the given ranges (i.e. the lower and the upper limit of the range). For example, if a range is given of e.g. 1 to 5 days, this shall include 1, 2, 3, 4, and 5 days. The same applies to any other ranges, including but not limited to other time periods (e.g. infusion time in hours), any dose ranges (e.g. per m² body surface area, per kg body weight, per day, per treatment cycle etc.), infusion rates, concentrations, percentages, factors, ratios, and numbers.

The cytolysis threshold dose may be determined by a complement dependent cytolysis (CDC) assay or a whole blood test (WBT). The WBT is an assay in which the target cells or target components (i.e. cells, liposomes or other cell-like compartments to be lysed) are contacted with appropriately anti-coagulated whole blood from the patient. The CDC assay can be, for example, a standard CDC assay as known in the art (e.g. as described in Indusogie et al., J Immunol 2000, Zeng et al., Molecular Immunology 2005, or in WO2005/070967). The CDC assay and/or the WBT may be done with GD2 positive target cells, such as tumor cell lines of the GD2 positive cancer to be treated. For example, if the patient to be treated suffers from neuroblastoma, the cell line may be a neuroblastoma cell line, such as e.g. LAN-1 human neuroblastoma cells. In another example, if the patient to be treated suffers from melanoma, the cell line may be a melanoma cell line, such as e.g. M21 human melanoma cells. In still another embodiment, the target cells of the CDC assay and/or the WBT are tumor cells obtained from the patient, i.e. autologous tumor cells of the patient. In another embodiment, the target component of the CDC assay and/or WBT is a liposome displaying GD2 on the surface. The target cells or target components are labeled with a signaling component, e.g. with a radioactive component, such as $^{51}Cr$, or with a fluorescent component, such as calcein. The signaling component is comprised by the target cell or target component, i.e. is inside of the target cell or target component (e.g. a liposome packed with the signaling component and displaying GD2 on the surface), and is released upon lysis of the target cell or target component. Thus, the signaling component provides the assay readout. The target cells or components loaded with the signaling compound are contacted with the whole blood, serum, or plasma in a certain ratio. The whole blood, plasma, or serum may be diluted for the CDC or WBT, e.g. in a ratio of 1:2 or higher, e.g. 1:4, 1:5, or 1:10, or any range in between these ratios prior to adding it to the sample. However, it may also be added to the sample un-diluted. The final concentration of the whole blood, plasma, or serum in the CDC or WBT sample may e.g. be in the range of 10 to 50%. Target cell or target component lysis can be measured by release of said signaling component by a scintillation counter or spectrophotometry. For example, the target cell or target component lysis can be measured by determining the amount of $^{51}Cr$ released into the supernatant by a scintillation counter. The percentage of lysis may be determined by the following equation: 100×(experimental release−spontaneous release)/(maximum release−spontaneous release).

For the CDC assay, the cytolytic components (or effector components) are provided by serum or appropriately anti-coagulated plasma obtained from the patient or donor comprising the complement system components. For the WBT, the cytolytic components (or effector components) are provided by appropriately anti-coagulated whole blood obtained from the patient or donor comprising the complement system components as well as all cellular components, and also any further components comprised in whole blood which might be relevant to the target cell lysis, as well as the interplay of all components (e.g. complement activation is known to activate certain effector cells such as granulocytes) For the CDC and/or WBT, the serum, plasma, or whole blood may be added to the target cells or target components in different dilutions.

Furthermore, one or more samples of the CDC assay and/or WBT may be spiked with an anti-GD2 antibody in different dilutions, e.g. for generation of a standard curve.

In another embodiment, one or more anti-idiotypic (anti-id) anti-GD2 antibodies recognizing the variable domain of anti-GD2 antibodies may be added to a sample to inhibit the target cell lysis mediated by the antibody, e.g. as a negative control or to prove specificity of the assay and that the target cell lysis measured without the anti-id antibody is antibody-mediated or antibody dependent.

If the cytolysis threshold dose is determined for a patient before the start of the treatment with the preparation comprising an anti-GD2 antibody, the anti-GD2 antibody or the preparation comprising the anti-GD2 antibody is added in different dilutions to the CDC assay and/or WBT samples (in addition to the patient serum, plasma, or blood), so that the cytolysis threshold dose can be determined.

As further described herein, target cells for determination of the threshold dose may be human tumor cell lines of the same indication (e.g. human neuroblastoma cells in case of a neuroblastoma patient), or—if feasible—autologous tumor cells of the patient.

If the cytolysis threshold dose is determined for a patient during the treatment with the preparation comprising an anti-GD2 antibody, the serum, plasma, or whole blood of the patient (which comprises the anti-GD2 antibody) is added in different dilutions to the CDC assay and/or WBT samples (without the addition of separate anti-GD2 antibody), so that the cytolysis threshold dose can be determined.

The dose sufficient to induce CDC and/or whole blood cytolysis may be defined as the dose that achieves at least 20, 25, 30, 35, 40, 45, or 50%, or any range in between these levels of the maximal possible target cell lysis in that respective assay (a specific CDC assay or WBT). In one embodiment, the dose is defined as the dose that achieves at least 55%, at least 60%, at least 65%, at least 70%, at least 75%, at least 80%, at least 85%, at least 90%, at least 95%, or 100%, or any range in between these levels of maximal possible cell lysis in the respective assay (a specific CDC assay or WBT).

The cytolysis threshold dose determined in a specific CDC assay or WBT is a serum-, plasma-, and/or blood-level of anti-GD2 antibody. The dose of the preparation comprising the anti-GD2 antibody to be administered to patient to achieve such blood, plasma and/or serum antibody levels has then to be determined accordingly based on pharmacokinetic data for said preparation. As shown in FIGS. 1 and 2, antibody levels as low as 470 to 1000 ng/mL serum or plasma are sufficient to induce at least 50% tumor cell lysis in that CDC assay, e.g. 470 ng/mL (FIG. 2), or 1000 ng/mL (FIG. 1) of APN311, and 619 ng/mL of APN301 (FIG. 2). Accordingly, in one embodiment of the invention, the cytolysis threshold dose is 470 to 1000 ng/mL serum or plasma, or 470 to 10000 ng/mL serum or plasma, or any range in between these levels.

If a certain cytolysis threshold dose is determined in a CDC assay or a WBT, especially such assays in which target cells other than the patient's tumor cells are used, said cytolytic threshold determined in vitro (in vitro cytolytic threshold dose) may be increased by a certain margin of safety to ensure that the antibody dose is sufficient to induce cytolysis of the patient's tumor cells in vivo (in vivo cytolysis threshold dose). Accordingly, the in vitro cytolysis threshold dose may be increased by a factor of 1 to 10, or any range in between these factors.

In certain embodiments, the cytolysis threshold dose is 1410 to 3000 ng/mL or 2350 to 5000 ng/mL serum or plasma, or any range in between these levels.

The dose of the preparation comprising the anti-GD2 antibody to be administered to the patient is determined accordingly, i.e. it is administered in a dose to achieve said serum or plasma levels within the first 1-4 days of treatment with the preparation comprising the anti-GD2 antibody (e.g. on day 1, 2, 3, or 4 of the treatment period with the preparation comprising the anti-GD2 antibody), and said serum or plasma level is maintained over the entire treatment period with the preparation comprising the anti-GD2 antibody. As shown in FIGS. 1 and 2, antibody levels as low as 2 to 234 ng/mL in whole blood are sufficient to induce at least 50% tumor cell lysis in that WBT, e.g. 2 ng/mL (FIG. 1), or 10 ng/mL (FIG. 1), or 21 ng/mL (FIG. 2), of APN311, and 234 ng/mL of APN301 (FIG. 2). Accordingly, in one embodiment of the invention, the cytolysis threshold dose is 2 to 250 ng/mL whole blood, or 2 to 2500 ng/mL whole blood, or any range in between these levels. In certain embodiments, the cytolysis threshold dose is 2 to 100 ng/mL whole blood, or 5 to 200 ng/mL whole blood, or any range in between these levels. In some embodiments, the cytolysis threshold dose is 6 to 750, 6 to 7500, 10 to 1250, 10 to 12500, 6 to 300, 10 to 500, 15 to 600, or 25 to 1000 ng/mL whole blood.

Figure 6:
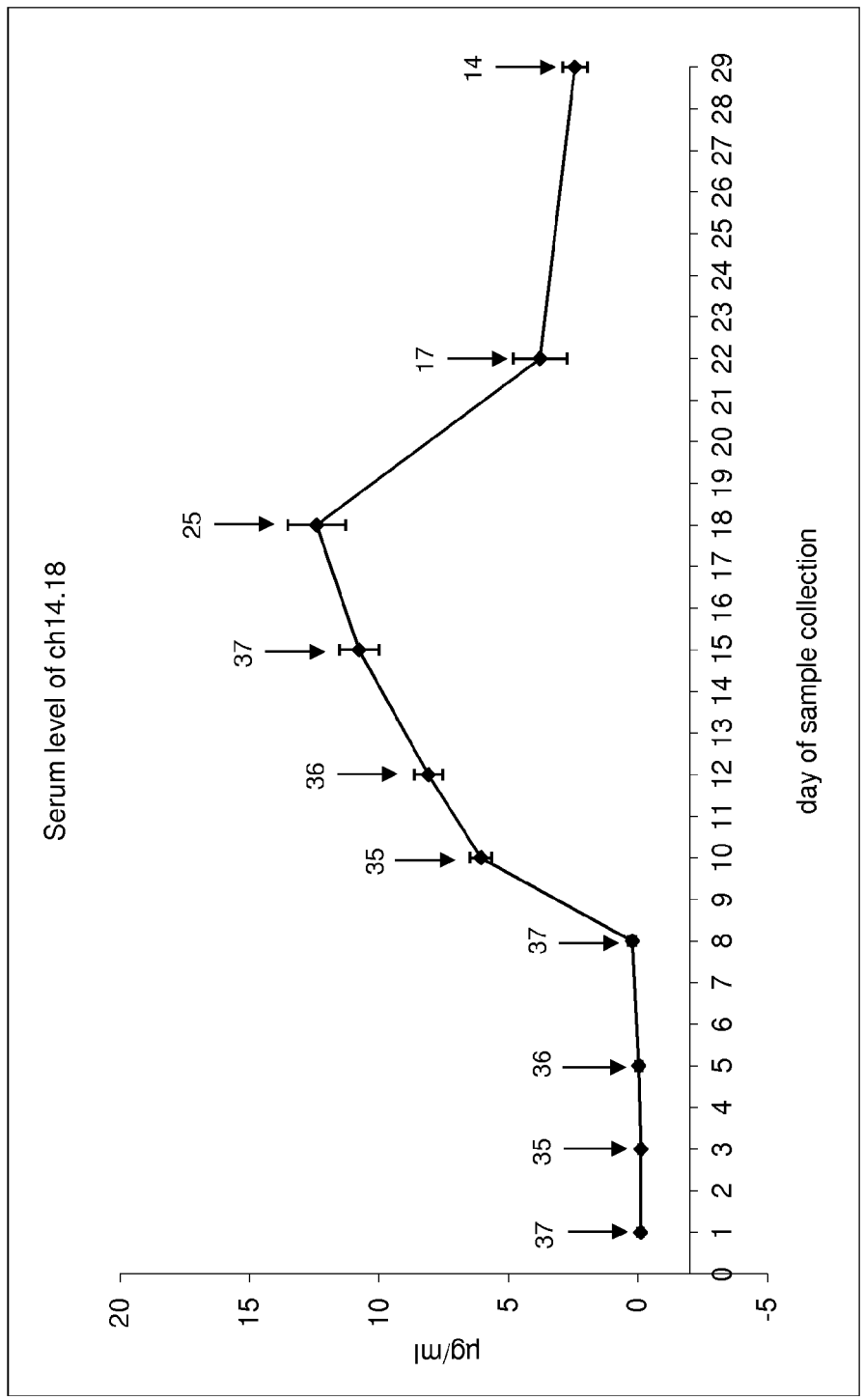
FIG. 6 shows the pharmacokinetics of APN311 in serum of patients. The numbers above the mean serum levels indicate the number of patients included in said mean at this day of sample collection. The treatment period with APN311 was from day 8 to 18, the two treatment periods with IL-2 were on days 1 to 5 and 8 to 12 of the treatment cycle.

The dose of the preparation comprising the anti-GD2 antibody to be administered to the patient is determined accordingly, i.e. it is administered in a dose to achieve said whole blood levels within the first 1-4 days of treatment with the preparation comprising the anti-GD2 antibody (e.g. on day 1, 2, 3, or 4 of the treatment period with the preparation comprising the anti-GD2 antibody), and said serum or plasma level is maintained over the entire treatment period with the preparation comprising the anti-GD2 antibody. As can be seen in FIG. 6, serum levels of 1000 ng/mL (or 1 μg/mL) can be achieved within the first one or two days of anti-GD2 antibody treatment, if the preparation comprising the anti-GD2 antibody is administered in a dose of 10 mg/m²/day as a continuous intravenous (i.v.) infusion, i.e. for 24 h per day, using a mini-pump. Thus, in one embodiment, the preparation comprising the anti-GD2 antibody is administered in a dose of 5, 7, 10 or 15, especially 10 mg/m²/day or any range in between these doses as a continuous intravenous infusion (24 h per day). In one embodiment, the cytolysis threshold dose is achieved within the first, second, third or fourth day of the treatment with the preparation comprising the anti-GD2 antibody. FIG. 7 shows that 50% of cytolysis can be achieved within the first three or four days of the treatment with the preparation comprising the anti-GD2 antibody, if the preparation comprising the anti-GD2 antibody is administered in a dose of 10 mg/m²/day as a continuous intravenous (i.v.) infusion, i.e. for 24 h per day, using a mini-pump.

With the methods of the present invention it is possible to reduce the antibody dose to the minimum dose required for tumor cell lysis and/or target cell lysis as determined by a CDC assay or a WBT. In certain embodiments, the cytolysis threshold dose of the antibody determined by a CDC assay and/or a WBT is lower than 50, 40, 30, 25, 20, 15, 10, 7, 5 mg/m²/day, or lower than any range in between these doses. Furthermore, the methods of the invention allow to individually determine the cytolysis threshold dose by a CDC assay and/or a WBT and thus, take into account the individual differences in the lytic capacity against tumor cells of the patients. Accordingly, each patient may receive his or her optimal antibody dose that is as low as possible to minimize potential side effect, especially pain, but is effective in tumor cell lysis.

The preparation may be administered to a subject in need thereof. In one embodiment, the subject is a GD2 positive cancer patient. A GD2 positive cancer is a type of cancer, in which GD2 is expressed on tumor cells and comprises, for example, neuroblastoma, glioblastoma, medulloblastoma, astrocytoma, melanoma, small-cell lung cancer, desmoplastic small round cell tumor, osteosarcoma, rhabdomyosarcoma, and other soft tissue sarcomas. In one embodiment, the patient suffers from primary refractory or relapsed high risk-neuroblastoma, or from minimal residual disease in high-risk neuroblastoma. The patient may have previously been treated or is simultaneously treated with another therapy, such as e.g. surgery, chemotherapy, radiation, stem cell transplantation, cytokine treatment (e.g. with IL-2 and/or GM-CSF), and/or retinoid treatment (e.g. with isotretinoin).

The antibody can be selected from the group of recombinant or artificial, including single chain antibodies, mammalian antibodies, human or humanized antibodies. It may comprise or be selected from constant and/or variable portions of an antibody in particular selected from Fc, Fc-like, Fv, Fab, F(ab)₂, Fab', F(ab')2, scFv, scfc, VHH. However, any such antibody fragment should comprise the Fc portion that is responsible for complement binding, and thus, can mediate the natural (or in vivo) effector functions. Preferably the antibody comprises a light and heavy chain of an antibody. The antibody may comprise one or two antigen binding regions, which may bind the same or different antigen, e.g. GD2, that may be bound specifically. The inventive antibodies can be directed—e.g. generated by immunization against—the antigens as defined above. The anti-GD2 antibody may be a humanized or chimeric GD2 antibody, e.g. a humanized or chimeric 14.18, 3F8 or 8B6 antibody, or an antigen-binding fragment thereof which mediates the natural effector functions. The anti-GD2 antibody may have one or more amino acid modifications, such as e.g. a modified Fc region. In one embodiment, the anti-GD2 antibody is hu14.18K322A. In another embodiment, the anti-GD2 antibody is a chimeric 14.18 antibody. In one embodiment, the anti-GD2 antibody has the light chain nucleotide sequence of SEQ ID NO:1 (see also Example 1) and the heavy chain nucleotide sequence of SEQ ID NO:2 (see also Example 1). In one embodiment, the anti-GD2 antibody has the light chain amino acid sequence of SEQ ID NO:3 (see also Example 1) and the heavy chain amino acid sequence of SEQ ID NO:4 (see also Example 1). The relative molecular mass of the antibody comprising of two light and two heavy chains may be approximately 150,000 Dalton. In one embodiment, the anti-GD2 antibody is APN311. The anti-GD2 antibody may be expressed in CHO cells, in SP2/0 cells, or in other suitable cell lines, such as e.g. HEK-293, MRC-5, Vero, PerC6, or NS0. In one embodiment, the anti-GD2 antibody is a chimeric 14.18 antibody expressed in SP2/0 cells. In another embodiment, the anti-GD2 antibody is a chimeric 14.18 antibody expressed in CHO cells.

The anti-GD2 antibody may also be an immunocytokine comprising a fusion protein of an anti-GD2 antibody (or an antigen-binding fragment thereof which mediates the natural effector functions) and a cytokine. The antibody part of the immunocytokine may be a humanized or chimeric GD2 antibody, e.g. a humanized or chimeric 14.18, 3F8 or 8B6 antibody. The antibody part of the immunocytokine protein may have one or more amino acid modifications, such as e.g.

a modified Fc region. In one embodiment, the antibody part of the immunocytokine is hu14.18K322A. In another embodiment, the antibody part of the immunocytokine is a humanized 14.18 antibody. The cytokine part of the anti-GD2 antibody-cytokine fusion protein may be, for example, IL-2 or Interleukin-12 (IL-12), or IL-15 or GM-CSF. The antibody and the cytokine are fused together and may comprise a linker sequence. In one embodiment, the immunocytokine has the light chain nucleotide sequence of SEQ ID NO:5 (see also Example 1) and the heavy chain nucleotide sequence of SEQ ID NO:6 (see also Example 1). In one embodiment, the immunocytokine has the light chain amino acid sequence of SEQ ID NO:7 (see also Example 1) and the heavy chain amino acid sequence of SEQ ID NO:8 (see also Example 1). In one embodiment, the immunocytokine is APN301. The immunocytokine may be expressed in NS0 cells, or in other suitable cell lines, such as e.g. CHO, HEK-293, MRC-5, Vero, or PerC6.

In certain embodiments, the anti-GD2 antibody is not fused to any other moiety. In certain embodiments, the anti-GD2 antibody is not an immunocytokine.

The preparation comprising an anti-GD2 antibody may further comprise salts and WFI. In one embodiment, the preparation comprising an anti-GD2 antibody may further comprise a buffer, e.g. phosphate buffered saline, comprising said salts and WFI.

The preparation comprising an anti-GD2 antibody may further comprise stabilizing agents, preservatives and other carriers or excipients. The preparation comprising an anti-GD2 antibody may be freeze-dried. In one embodiment, the preparation comprising an anti-GD2 antibody comprises an anti-GD2 antibody-cytokine fusion (e.g. hu14.18-IL-2) and further comprises sucrose, L-arginine, citric acid monohydrate, polysorbate 20, and hydrochloric acid. In an embodiment, the preparation comprising an anti-GD2 antibody is APN301, the anti-GD2 antibody is hu14.18-IL-2 and the preparation comprises 4 mg/mL immunocytokine, 20 mg/mL sucrose, 13.9 mg/mL L-arginine, 2 mg/mL polysorbate 20, and 2.1 mg/mL citric acid monohydrate. In an embodiment, said preparation comprising an immunocytokine and other excipients is freeze-dried, can be reconstituted in 4 mL of 0.9% sodium chloride, and the resulting solution has a pH of 5.5. In one embodiment, the preparation comprising an anti-GD2 antibody does not comprise stabilising agents, preservatives and other excipients. The preparation comprising an anti-GD2 antibody may be added to an infusion bag, e.g. an infusion bag containing 100 ml NaCl 0.9% and 5 ml human albumin 20%.

The anti-GD2 antibody or the preparation comprising an anti-GD2 antibody may be administered in daily antibody doses of 1 to 30 mg/m$^2$, 1 to 35 mg/m$^2$, 1 to 50 mg/m$^2$, or 1 to 60 mg/m$^2$, e.g. 1, 2, 3, 4, 5, 6, 7, 7.5, 8, 9, 10, 12, 15, 20, 25, 30, 32, 35, 40, 45, 50, or 60 mg/m$^2$ or any range in between these periods. For example, a daily dose of 10 mg/m$^2$ means that the patient receives 10 mg anti-GD2 antibody per m$^2$ of body surface per day. As used herein, a dose (e.g. given in mg or microgram) refers to the dose of the active ingredient, i.e. to the amount of active ingredient in the preparation. For example, the given dose may refer to the amount of anti-GD2 antibody in the preparation comprising an anti-GD2 antibody, or the immunocytokine in the preparation comprising the immunocytokine, or the cytokine in the preparation comprising the cytokine. As specified in the example above, a daily dose of 10 mg/m$^2$ means that the patient receives 10 mg anti-GD2 antibody (optionally contained in a certain volume of the preparation comprising the anti-GD2 antibody) per m$^2$ of body surface per day. As used herein, a dose given per m$^2$ means per m$^2$ of body surface area (BSA) of the patient. As used herein, a dose given per kg means per kg of body weight of the patient.

In some embodiments, the preparation comprising an anti-GD2 antibody is administered in daily doses of 1 to 15, 1 to 20, 1 to 25, 1 to 30, or 1 to 35 mg/m$^2$, or any range in between these daily doses. In certain embodiments, the preparation comprising an anti-GD2 antibody is administered in daily doses of less than 50, 40, 30 or 25 mg/m$^2$. In certain embodiments, the preparation comprising an anti-GD2 antibody is administered in daily doses of up to 7, 10, 15 or 20 mg/m$^2$. The anti-GD2 antibody may be administered in a dose of 10, 20, 25, 50, 60, 75, 80, 100, 120, 150, 200, 210, 250, or 300 mg/m$^2$/cycle or any range in between these doses. The total dose per patient per treatment cycle may be defined as the predetermined overall patient dose.

In some embodiments, the preparation comprising an anti-GD2 antibody is administered for a treatment period until a certain therapeutic effect has been reached. In some embodiments, the therapeutic effect may be an increase in immune response to the tumor, as determined, for example, by an increase in immune system biomarkers (e.g. blood parameters, such as lymphocyte counts and/or NK cell numbers; and/or cytokines). In some embodiments, the therapeutic effect may be a reduction in tumor markers (e.g. catecholamines). In some embodiments, the therapeutic effect may be determined by methods such as metaiodobenzylguanidine scintigraphy (mIBG), magnetic resonance imaging (MRI) or X-ray computed tomography (CT), and/or bone marrow histology (assessed by aspirate or trephine biopsy).

In certain embodiments, the therapeutic effect may be defined as stable disease (i.e. no further increase in lesions, tumor tissue and/or size), partial response (i.e. reduction in lesions, tumor tissue and/or size), and/or complete response (i.e. complete remission of all lesions and tumor tissue.

Complete Response (CR) may be further defined as follows:
Complete disappearance of all measurable and evaluable disease,
no new lesions,
no disease-related symptoms, and/or
no evidence of evaluable disease, including e.g. normalization of markers and/or other abnormal lab values.
In some embodiments, all measurable, evaluable, and non-evaluable lesions and sites must be assessed using the same technique as baseline.

Partial Response (PR) may be further defined as follows:
Applies only to patients with at least one measurable lesion.
Greater than or equal to 50% decrease under baseline in the sum of products of perpendicular diameters of all measurable lesions.
No progression of evaluable disease.
No new lesions.

In some embodiments, all measurable and evaluable lesions and sites must be assessed using the same techniques as baseline. The preparation comprising an anti-GD2 antibody may be administered as continuous intravenous infusion for 24 hours per day. The preparation comprising an anti-GD2 antibody may be administered for 10, 14, 15, or 21 consecutive days or any range in between these periods. The preparation comprising an anti-GD2 antibody may also be administered for 4, 5, 6, 7, 8, 9, 10, 11, 12, 13, 14, 15, 16, 17, 18, 19, 20, 21, or more consecutive days. In certain embodiments, the preparation comprising an anti-GD2 antibody is administered over the entire treatment cycle, e.g. for 35 days. In some embodiments, the preparation comprising an anti-GD2 antibody is administered as a continuous intravenous infusion for the overall treatment time, e.g. over 5 treatment cycles with 35 days each, i.e. over 180 days in total. The daily antibody dose may be reduced accordingly, so that the predetermined patient dose of the antibody is administered. In one embodiment, the predetermined patient dose of the antibody is 100 mg/m$^2$/cycle. In one embodiment, the overall treatment time comprises 5 cycles. Accordingly, in this example, the antibody dose per overall treatment time is 500 mg/m$^2$. In an embodiment, this total antibody dose of 500 mg/m$^2$ per overall treatment time is administered over 180 days, i.e. in 2.77 mg/m$^2$/day. The preparation comprising an anti-GD2 antibody may be administered as a continuous intravenous infusion over a time period of 24 hours per day. For such continuous infusion, an osmotic mini-pump may be used. In one embodiment, the preparation comprising an anti-GD2 antibody is administered as continuous intravenous infusion for 24 hours per day for 10, 14, 15 or 21 consecutive days or any range in between these periods, in daily doses as specified above (e.g. 7, 10, or 15 mg/m$^2$/day), e.g. 10 mg/m$^2$/day for 10 days, 15 mg/m$^2$/day for 10 days, 7 mg/m$^2$/day for 14 days, 15 mg/m$^2$/day for 14 days, 10 mg/m$^2$/day for 15 days, 7 mg/m$^2$/day for 21 days, or 10 mg/m$^2$/day for 21 days or any range in between these doses. In certain embodiments, the preparation comprising an anti-GD2 antibody is not administered as continuous intravenous infusion for 5 days in a daily dose of 40 mg/m$^2$. In certain embodiments, the preparation comprising an anti-GD2 antibody is not administered as continuous intravenous infusion for 5 days, i.e. not as a 120-hour-infusion. In some embodiments, the preparation comprising an anti-GD2 antibody is administered as continuous intravenous infusion for more than 5 days. In some embodiments, the preparation comprising an anti-GD2 antibody is administered as continuous intravenous infusion for 6 or more days.

The immunocytokine or the preparation comprising the immunocytokine may be administered in daily immunocytokine doses of 0.8 to 50 mg/m$^2$, e.g. 0.8, 1.6, 2, 3.2, 4, 4.8, 5, 6, 7, 7.5, 8, 9, 10, 12, 14.4, 15, 20, 25, 30, 32, 40, 45, or 50 mg/m$^2$ or any range in between these doses. For example, a daily dose of 10 mg/m$^2$ means that the patient receives 10 mg immunocytokine per m$^2$ of body surface per day. In one embodiment, one milligram of fusion protein contains approximately 0.8 mg of hu14.18 antibody and approximately 3×10$^6$ U of IL-2. The preparation comprising an immunocytokine may be administered subcutaneously or as intravenous infusion, e.g. once a day. The preparation comprising an immunocytokine may be administered i.v. over a time period of 24 hours per day. The preparation comprising an immunocytokine may be administered for 2, 3, 4, 5, 10, 14, 15, or 21 consecutive days or any range in between these periods. In another embodiment, the preparation comprising an immunocytokine is administered as continuous intravenous infusion for 24 hours per day for 10, 14, 15 or 21 consecutive days. For such continuous infusion, an osmotic mini-pump may be used. In one embodiment, the immunocytokine is administered in a dose of 12 mg/m$^2$/day for 3 consecutive days in 28-day cycles (in up to 10 cycles).

The treatment period with the preparation comprising an anti-GD2 antibody may be preceded and/or accompanied by one or more treatment periods with a cytokine. In one embodiment, the cytokine is Granulocyte colony-stimulating factor (G-CSF), GM-CSF, IL-2, IL-12, and/or IL-15. The cytokine may be administered subcutaneously (e.g. once a day), or as intravenous infusion. In one embodiment, the cytokine is IL-2 and is administered subcutaneously once a day in a dose of 6×10$^6$ IU/m$^2$/day, e.g. on days 1 and 2 and on days 8 to 14 of the treatment cycle, or e.g. on days 1 to 5 and on days 8 to 12 of the treatment cycle. In one embodiment, the overall patient dose of IL-2 is 60×10$^6$ IU/m$^2$/cycle. In another embodiment, the cytokine is GM-CSF and is administered intravenously once a day over 2 hours in a dose of 250 micrograms/m$^2$/day, e.g. on days 1 and 2 and 8 to 14 of the treatment cycle.

The treatment period with the preparation comprising an anti-GD2 antibody may be followed by one or more treatment periods with a retinoid. In one embodiment, the retinoid is a retinoic acid (RA), e.g. isotretinoin.

Any such treatment period may be repeated. Any such treatment period may be followed by an interval of no treatment, either with the same and/or with different drugs or treatments. In one embodiment, the interval may be an interval free of any treatment. In another embodiment, the interval is free of administration of the same preparation or treatment, however, other preparations or treatments may be administered during the interval.

Furthermore, the method according to the present invention may be preceded and accompanied by a treatment with one or more analgesics, such as e.g. non-steroidal anti-inflammatory drugs (NSAIDs, e.g. indometacin), and/or one or more opioids, and/or one or more other analgesics, or any combination thereof. In one embodiment, the analgesic is an opioid, e.g. morphine and/or morphine derivatives, such as e.g. hydromorphone. Other opioids are, for example, tramadol, pethidine, codeine, piritramide, levomethadone, as well as fentanyl, alfentanil, remifentanil and sufentanil.

In some embodiments, the one or more analgesics may be selected from GABA-analogues, such as e.g. gabapentin. Accordingly, the patient may be treated with gabapentin, e.g. three days prior to the start of the antibody treatment period. Gabapentin may be administered orally in a dose of 10 mg/kg/dose once, twice or three times a day. Gabapentin may be given in a dose of up to 300 mg/kg/dose. Gabapentin is available and may be administered as oral solution containing 250 mg/5 mL of gabapentin, or in capsules (100 mg, 300 mg, and 400 mg). The gabapentin treatment may be administered in addition to the treatment with morphine and/or other analgesics. Furthermore, the patient may be treated with paracetamol (10 to 15 mg/kg/dose, every 4 hours or four times a day, orally or intravenously), ibuprofen (5 to 10 mg/kg/dose orally every 6 to 12 hours), metamizol (10 to 15 mg/kg/dose orally every 4 hours), diphenhydramine (0.5 to 1 mg/kg/dose orally or intravenously), and/or indometacin (e.g. 0.3 to 0.5 mg/kg/dose, or 25 or 50 mg/dose, orally or intravenously every 6 hours). Said treatment with paracetamol, ibuprofen, metamizol, and/or indometacin may be administered in addition to the treatment with morphine and/or gabapentin, and/or other analgesics.

The one or more analgesics may be administered as intravenous infusion, especially as continuous intravenous infusion for 24 hours per day. The treatment period with the one or more analgesics may precede and/or accompany the treatment period with the preparation comprising an anti-GD2 antibody.

With the methods according to the invention, it is possible to reduce the dose, to change the route of administration (e.g. from intravenous infusion to oral), to reduce the duration of the analgesic treatment period(s), and/or to change the kind of preparation of the one or more analgesics. Thus, the present invention even allows for an outpatient management, at least for a part of the treatment cycle, of patients on treatment with a preparation comprising an anti-GD2 antibody.

In some embodiments, the daily dose of the one or more analgesics on one or more antibody treatment days according to the invention (continuous infusion) is lower than the usual daily dose administered during the treatment with a preparation comprising an anti-GD2 antibody that is administered as a non-continuous intravenous infusion, or that is administered as a continuous intravenous infusion for 5 days in a daily dose of 40 mg/m$^2$.

In certain embodiments, the dose (e.g. the daily dose) of the one or more analgesics (e.g. morphine) is reduced over time, e.g. within the overall treatment time, within a treatment cycle, during the antibody treatment period within a treatment cycle, from one antibody treatment day to the next antibody treatment day within a treatment cycle, and/or from one treatment cycle to the next. Examples of such morphine dose reductions are given in Table 9. For example, the morphine dose can be reduced by 10% from day 9 to 10 of the third treatment cycle, namely from 28% to 18% of the standard infusion rate (which in this example is 30 mcg/kg/h), or from 8.1 to 4.53 mg/kg/h, or from 0.19 to 0.11 mg/kg/day. In some embodiments, the morphine dose is continuously reduced within a treatment cycle, during the antibody treatment period within a treatment cycle, and/or from one antibody treatment day to the next antibody treatment day within a treatment cycle.

For example, such usual morphine doses administered before and/or during a non-continuous infusion (or bolus infusion, i.e. an infusion for less than 24 hours a day) treatment period with a preparation comprising an anti-GD2 antibody are given in table 1. In this example, the ch14.18/CHO (APN311) is given as an 8 hour infusion per day on 5 subsequent days for 5 cycles in a dose of 20 mg/m$^2$/day and thus 100 mg/m$^2$/cycle, and morphine hydrochloride is given on each antibody treatment day in a bolus dose of 0.05 mg/kg/h for 2 hours prior to starting the APN311 infusion, in an infusion rate of 0.03 mg/kg/h for 8 hours during the APN311 infusion, and in an interval infusion rate of 0.01 mg/kg/h for 14 hours on the first day of APN311 treatment, and for 4 hours on subsequent treatment days, if tolerated (with an interval of 10 hours with no morphine treatment). The dose was increased (e.g. increase in infusion rate during antibody infusion) and/or additional bolus doses were administered on an as needed basis. Accordingly, the prescribed morphine dose was at least 0.38 mg/kg per day, at least 2 mg/kg per treatment cycle (comprising 5 antibody treatment days), and at least 10 mg/kg per overall treatment time (comprising three cycles).

In certain embodiments, the one or more daily morphine doses and/or the one or more morphine infusion rates and/or the one or more percentages of the standard morphine doses are as specified in Table 9. For example, in one embodiment the percentage of the standard morphine dose administered on day 12 of the first treatment cycle is 41%, the morphine infusion rate on day 12 of the first treatment cycle is 12.26 mg/kg/h, and the daily morphine dose on day 12 of the first treatment cycle is 0.29 mg/kg.

TABLE 1

Morphine infusion schedule
Prepare 10 mg morphine in 40 mL glucose 5% (0.25 mg = 1 mL)

|  | duration of morphine infusion (h) | morphine infusion rate (mg/kg/h) | morphine dose mg/kg |
|---|---|---|---|
| pre-infusion | 2 | 0.05 | 0.1 |
| infusion during APN311 treatment | 8 | 0.03 | 0.24 |
| interval infusion | 14 or 4 | 0.01 | 0.14 or 0.04 |
| total dose per treatment day (mg/kg/24 h) |  |  | 0.48 or 0.38 |

In another example, APN311 is given as an 8 hour infusion per day on 5 subsequent days for 3 cycles in a dose of 10, 20, and 30 mg/m$^2$/day and 50, 100, 150 mg/m$^2$/cycle, and morphine hydrochloride is given on each antibody treatment day in a bolus dose of 0.5-1.0 mg/kg/dose (just prior to the start of infusion of the antibody), and in a rate of 0.05 mg/kg/hour continuous infusion during the APN311 infusion. The dose is increased (e.g. increase in infusion rate during antibody infusion) and/or additional bolus doses are administered on an as needed basis. Accordingly, the prescribed morphine dose is at least 0.9 mg/kg per day, at least 4.5 mg/kg per treatment cycle (comprising 5 antibody treatment days), and at least 13.5 mg/kg per overall treatment time (comprising three cycles).

In other examples of non-continuous (or bolus) infusions of ch14.18, morphine has been administered in infusion rates up to 1.2 mg/kg/h over 24 hours.

In still another example, ch14.18/Sp2/0 is given in a dose of 25 mg/m$^2$/day on four consecutive days. Each dose of ch14.18/Sp2/0 is infused i.v. over 5.75 hours, starting at 1.25 mg/m$^2$/h×0.5 h, then 2.5 mg/m$^2$/h×0.5 h, then 3.75 mg/m$^2$/h×0.5 h, then to 5 mg/m$^2$/h for the remaining dose, if tolerated. In said example, each treatment cycle starts on day 0, and day 0 of a treatment cycle is the first day of treatment with the respective cytokine.

TABLE 2

Schema for the administration of 5 cycles of ch14.18/Sp2/0, cytokines, and isotretinoin (retinoic acid or RA).

| Cycle 1 | Cycle 2 | Cycle 3 | Cycle 4 | Cycle 5 |
|---|---|---|---|---|
| Ch14.18 | Ch14.18 | Ch14.18 | Ch14.18 | Ch14.18 |
| GM-CSF | Aldesleukin (IL-2) | GM-CSF | Aldesleukin (IL-2) | GM-CSF |
| RA | RA | RA | RA | RA |

Ch14.18/SP2/0 treatment is administered every 28 days at 25 mg/m$^2$/day×4 days for all 5 cycles; GM-CSF at 250 micrograms/m$^2$/day for 14 days; Aldesleukin (IL-2) at 3 MIU/m$^2$/day for first week, 4.5 MIU/m$^2$/day for second week.

TABLE 3

Treatment schema for cycles with GM-CSF

| Day | 0 | 1 | 2 | 3 | 4 | 5 | 6 | 7 | 8 | 9 | 10 | 11 | 12 | 13 | 14-23 | 24 |
|---|---|---|---|---|---|---|---|---|---|---|---|---|---|---|---|---|
| GM-CSF | X | X | X | X | X | X | X | X | X | X | X | X | X | X | | Begin Cycle 2&4 |
| ch14.18 | | | | ⇧ | ⇧ | ⇧ | ⇧ | | | | | | | | | |
| RA | | | | | | | | | | | ⇧ | ⇧ | ⇧ | ⇧ | ⇧ | |

Note: In variation to the treatment schema above, the RA treatment is started on day 11 of the first cycle, but according to the schema on day 10 of the third and fifth cycle. Accordingly, in variation to the treatment schema above, day 24 of the first treatment cycle is also the last day of RA treatment of the first cycle.

GM-CSF is given at 250 micrograms/m²/day as subcutaneous injection (strongly recommended) or i.v. as a 2 hour infusion daily from Day 0 through 13 (daily with the infusion of ch14.18/SP2/0 and for 3 days before and 7 days after the antibody treatment).

TABLE 4

Treatment schema for cycles with aldesleukin (IL-2)

| Day | 0 | 1 | 2 | 3 | 4-6 | 7 | 8 | 9 | 10 | 11-13 | 14 | 15 | 16 | 17 | 18-27 |
|---|---|---|---|---|---|---|---|---|---|---|---|---|---|---|---|
| IL-2 | X | X | X | X | | X | X | X | X | | | | | | |
| ch14.18 | | | | | | ⇧ | ⇧ | ⇧ | ⇧ | | | | | | |
| RA | | | | | | | | | | | ⇧ | ⇧ | ⇧ | ⇧ | ⇧ |

On days 28-31 of the aldesleukin cycles no treatment is administered. On day 32, the next treatment cycle (with GM-CSF) is started (day 32=day 0 of the following cycle).

Aldesleukin (Interleukin-2, IL-2) in a dose of 3 MIU/m²/day is given by continuous infusion (using a CADD® Ambulatory Infusion Pump or a similar infusion pump) for 4 days (on Days 0-3) during the first week of each cycle. During the second week of each cycle, Aldesleukin (IL-2) is given at 4.5 MIU/m²/day for 4 days (on Days 7 to 10, with the infusion of ch14.18/SP2/0). Aldesleukin is continuously infused i.v. over 96 hours through a catheter via an ambulatory infusion pump in 5% dextrose in water (may contain 0.1% human serum albumin if needed), total volume dependent upon the pump.

A sixth treatment cycle may be added with 14 days of no treatment (starting on day 24 of the 5. cycle, which is day 0 of the sixth cycle) followed by 14 days of the administration of isotretinoin only.

In said example, hydroxyzine (1 mg/kg; max dose 50 mg) or diphenhydramine (0.5-1.0 mg/kg; max dose 50 mg) are given i.v. over 10 minutes to start 20 minutes prior to ch14.18/SP2/0 infusion; acetaminophen (10 mg/kg; max dose 650 mg) p.o. is given 20 minutes prior to ch14.18/SP2/0 infusion; and/or a morphine sulfate loading dose of 50 mcg/kg is given immediately prior to ch14.18/SP2/0 administration and then continued with morphine sulfate drip with an infusion rate of 20-50 micrograms/kg/h to continue for two hours after completion of the ch14.18/SP2/0 infusion. Additionally, other narcotics such as hydromorphone or fentanyl may be used. Alternatively, lidocaine infusion may be used in conjunction with an i.v. bolus of morphine, if required. The administration guidelines for lidocaine infusion are shown below:

Administration of Lidocaine:

a. Give lidocaine i.v. bolus at 2 mg/kg in 50 cc normal saline (NS) over 30 min prior to the start of ch14.18/SP2/0 infusion.

b. At the beginning of ch14.18/SP2/0 infusion, start i.v. lidocaine infusion at 1 mg/kg/h and continue until two hours after the completion of ch14.18/SP2/0 infusion.

c. May give morphine i.v. bolus 25-50 microgram/kg every 2 h, if needed.

In said example, one may also consider the administration of gabapentin with loading doses of morphine, and give morphine infusion/bolus as needed; may start with gabapentin 10 mg/kg/day and titrate up to 30-60 mg/kg/day depending on the clinical response.

In said example, doses of hydroxyzine (or diphenhydramine) and acetaminophen can be repeated every 6 h, if needed; i.v. or p.o.

In said example, additional doses of morphine can be given during the ch14.18/SP2/0 infusion to treat neuropathic pain followed by an increase in the morphine sulfate infusion rate, but patients should be monitored closely. If patients cannot tolerate morphine (e.g., itching), fentanyl or hydromorphone can be substituted for morphine. Alternatively, lidocaine infusion may be used in conjunction with i.v. bolus of morphine, if needed.

The term "morphine dose" as used herein refers to the amount of morphine (in mg or mcg) per kg of body weight of the patient. Accordingly, if it is referred to a daily morphine dose, it is the amount of morphine (in mg or mcg) per kg of body weight of the patient per day, or if it is referred to a morphine dose per hour, it is the amount of morphine (in mg or mcg) per kg of body weight of the patient per hour (or morphine infusion rate), or if it is referred to a morphine dose per treatment cycle, it is the amount of morphine (in mg or mcg) per kg of body weight of the patient per treatment cycle, or if it is referred to a morphine dose per overall treatment time, it is the amount of morphine (in mg or mcg) per kg of body weight of the patient per overall treatment time.

In some embodiments, the daily morphine dose administered during one or more days of continuous intravenous infusion of the antibody according to the invention and/or of all morphine treatment days is lower than the daily morphine dose during non-continuous administration of the antibody, e.g. in one or more of the examples described above. In certain embodiments, the daily morphine dose administered in a continuous antibody infusion schedule is 80% or less of the morphine dose administered in or prescribed for a non-continuous antibody infusion schedule in the first treatment cycle, 58% or less in the second treatment cycle, 57% or less in the third treatment cycle, 42% or less in the fourth treatment cycle, 34% or less in the fifth treatment cycle. In one embodiment, the daily morphine dose administered in an antibody treatment schedule according to the invention is lower than the daily morphine dose administered in an antibody treatment schedule of a continuous intravenous antibody infusion for 5 days in a daily dose of 40 mg/m². In some embodiments, the daily morphine dose administered during one or more days of continuous intravenous infusion of the antibody according to the invention and/or of all morphine treatment days is lower than 0.9, 0.72, 0.48, 0.38, 0.4375, and/or 0.205 mg/kg/day.

In certain embodiments, the daily morphine dose administered on the fifth, sixth, seventh, eighths, ninth, and/or tenth day of administration of the antibody in the first treatment cycle (applying a continuous intravenous infusion of the antibody according to the invention) is lower than the daily morphine dose in a non-continuous infusion schedule, e.g. 78% or less. In certain embodiments, the morphine dose administered on said day and any following days of the treatment cycle and/or of the overall treatment time is lower than the daily morphine dose in a non-continuous infusion schedule. In certain embodiments, the daily morphine dose administered on the third, fourth, fifth, sixth, seventh, eighths, ninth, and/or tenth day of administration of the antibody in the second treatment cycle (applying a continuous intravenous infusion of the antibody according to the invention) is lower than the daily morphine dose in a non-continuous infusion schedule, e.g. 60% or less. In certain embodiments, the morphine dose administered on said day and any following days of the treatment cycle and/or of the overall treatment time is lower than the daily morphine dose in a non-continuous infusion schedule. In some embodiments, the daily morphine dose administered on the first day of administration of the antibody in the third and any following treatment cycles (applying a continuous intravenous infusion of the antibody according to the invention) is lower than the daily morphine dose in a non-continuous infusion schedule, e.g. 57% or less. In certain embodiments, the morphine dose administered on said day and any following days of the treatment cycle and/or of the overall treatment time is lower than the daily morphine dose in a non-continuous infusion schedule.

In some embodiments, morphine is administered only for some but not all days on which the antibody is administered, e.g. only on the first 1, 2, 3, 4, 5, 6, or 7 days of continuous antibody infusion, e.g. in treatment cycles two, three, four, and/or five. In some embodiments, in cycle 6 of continuous antibody infusion, no morphine is administered.

In some embodiments, the morphine infusion rate, i.e. the morphine amount per kg body weight of the patient (or morphine dose) per hour, administered during one or more hours or days of the continuous intravenous infusion of the antibody according to the invention and/or of all hours or days of morphine treatment is lower than the standard morphine infusion rate prescribed for said schedule and/or the morphine infusion rate during non-continuous administration of the antibody in the examples described above, e.g. 96% or less on the second, 84% or less on the third, 65% or less on the fourth, 41% or less on the fifth, 14% on the sixth, 5% or less on the seventh, 3% on the eighth, 2% or less on the ninth, and/or 1% on the tenth day in the first treatment cycle, 72% or less in the second treatment cycle, 30% or less in the third treatment cycle, 22% or less in the fourth treatment cycle, 18% or less in the fifth treatment cycle. In some embodiments, the morphine infusion rate administered during one or more days of continuous intravenous infusion of the antibody according to the invention and/or of all morphine treatment days is lower than 50, 40, 30, 20, 10, and/or 5 mcg/kg/h, and/or lower than any range in between these infusion rates. In some embodiments, the morphine infusion rate administered during one or more days of continuous intravenous infusion of the antibody according to the invention and/or of all morphine treatment days is lower than 30 mcg/kg/h in the first and optionally any following treatment cycles, lower than 22 mcg/kg/h in the second and optionally any following treatment cycles, lower than 10 mcg/kg/h in the third and optionally any following treatment cycles, lower than mcg/kg/h in the fourth and optionally any following treatment cycles, and/or lower than 6 mcg/kg/h in the fifth and optionally any following treatment cycles.

In certain embodiments, the morphine dose per treatment cycle administered during one or more treatment cycles comprising the continuous intravenous infusion of the antibody according to the invention is lower than the morphine dose per treatment cycle in a non-continuous infusion schedule, e.g. 66% or less in the first treatment cycle; 64% or less, or 28% or less in the second treatment cycle; 29% or less, or 13% or less in the third treatment cycle; 16% or less, or 7% or less in the fourth treatment cycle; and/or 15% or less, or 6% or less in the fifth treatment cycle. In certain embodiments, the morphine dose per treatment cycle of the second and any following treatment cycles administered during one or more treatment cycles comprising the continuous intravenous infusion of the antibody according to the invention is lower than the morphine dose per treatment cycle in a non-continuous infusion schedule. In certain embodiments, the morphine dose of said treatment cycle and any following treatment cycles, and/or of the overall treatment time is lower than the morphine dose per treatment cycle in a non-continuous infusion schedule. In some embodiments, the morphine dose per treatment cycle administered during one or more treatment cycles comprising the continuous intravenous infusion of the antibody according to the invention is lower than 7.2, 4.8, 4.5, 2, 1.75, and/or 0.82 mg/kg/cycle, or lower than any range in between these doses.

In some embodiments, the morphine dose of the overall treatment time (applying a continuous intravenous infusion of the antibody according to the invention) is lower than the morphine dose of the overall treatment time in a non-continuous infusion schedule. In one embodiment, the morphine dose of the overall treatment time (applying a continuous intravenous infusion of the antibody according to the invention) is 55% or less, 50% or less, 45% or less, or 40% or less of the morphine dose of the overall treatment time in a non-continuous infusion schedule. In some embodiments, the morphine dose of the overall treatment time (applying a continuous intravenous infusion of the antibody according to the invention) is lower than 43.2, 28.8, 13.5, 10, 8.75, and/or 4.1 mg/kg/overall treatment time, and/or lower than any range in between these doses.

In some embodiments, the reference morphine doses in non-continuous infusion schedules, as referred to herein in comparison to the morphine doses in continuous infusion schedules according to the present invention, refer to the standard morphine doses for said schedule, or morphine doses prescribed for said schedule (e.g. as specified in the clinical study protocols. In some embodiments, the reference morphine doses as referred to herein refers to the morphine dose administered on the first day of treatment with the preparation comprising an anti-GD2 antibody in a treatment cycle with a continuous and/or non-continuous antibody infusion schedule, and is referred to as "starting morphine dose".

Accordingly, the term "reference morphine dose" as used herein shall comprise the morphine doses of treatment schedules other than those according to the present invention, and/or starting morphine doses; and shall encompass all examples of such morphine doses as referred to herein in comparison to the other morphine doses in continuous infusion schedules according to the present invention.

In certain embodiments, the reference morphine dose per hour infusion, i.e. the reference infusion rate, during the administration period of the antibody is 50 mcg/kg/h. In certain embodiments, the reference morphine dose per hour infusion, i.e. the reference infusion rate, during the administration period of the antibody is 30 mcg/kg/h. In certain embodiments, the reference morphine dose is 50, 40, 30, and/or 20 mcg/kg/h. In certain embodiments, the reference morphine dose is 0.9, 0.72, 0.48, 0.38, 0.4375, and/or 0.205 mg/kg/day. In certain embodiments, the reference morphine dose is 7.2, 4.8, 4.5, 2, 1.75, and/or 0.82 mg/kg/cycle. In certain embodiments, the reference morphine dose is 43.2, 28.8, 13.5, 10, 8.75, and/or 4.1 mg/kg/overall treatment time. In certain embodiments, the reference indometacin dose is 0.3 to 0.5 mg/kg/dose, or 25 or 50 mg/dose, orally or intravenously every 6 hours. In some embodiments, the reference morphine doses in non-continuous infusion schedules, as referred to above in comparison to the morphine doses in continuous infusion schedules according to the present invention, refer to the morphine doses as actually administered to the patients (e.g. the respective mean of the morphine doses administered to all treated patients of a clinical study).

The morphine doses in continuous infusion schedules according to the present invention, as referred to herein in comparison to the morphine doses in non-continuous infusion schedules, may refer to the standard morphine doses for said schedule, or morphine doses prescribed for said schedule (e.g. as specified in the clinical study protocols). In certain embodiments, the morphine dose per hour infusion, i.e. the infusion rate, during one or more hours or days of the continuous administration of the antibody is lower than 50 mcg/kg/h. In certain embodiments, the morphine dose per hour infusion, i.e. the infusion rate, during one or more hours or days of the continuous administration of the antibody is lower than 30 mcg/kg/h. In some embodiments, the morphine doses in continuous infusion schedules according to the present invention, as referred to above in comparison to the morphine doses in non-continuous infusion schedules, refer to the morphine doses as actually administered to the patients (e.g. the respective mean of the morphine doses administered to all treated patients of a clinical study).

In general, individual analgesic doses may vary depending on the individual patient's pain tolerance. Dosing may be adapted to obtain optimal analgesia.

The treatment period with the preparation comprising an anti-GD2 antibody may be combined with one or more treatment periods with a cytokine, one or more treatment periods with a retinoid, and/or one or more treatment periods with an analgesic. In one embodiment, the treatment period with the preparation comprising an anti-GD2 antibody combined with one or more of any such other treatment periods represent one treatment cycle.

In one embodiment, a patient who is treated with the method according to the invention is also treated with GM-CSF, IL-2, and/or isotretinoin, and optionally morphine, and/or one or more morphine derivatives, and/or one or more other analgesics. In one embodiment, the treatment period with the preparation comprising an anti-GD2 antibody is preceded by a treatment period with the cytokine. In one embodiment, the treatment period with the preparation comprising an anti-GD2 antibody is accompanied by a treatment period with the cytokine. In one embodiment, the treatment period with the preparation comprising an anti-GD2 antibody is preceded by a treatment period with the cytokine and accompanied by another treatment period with the cytokine.

Figure 8:
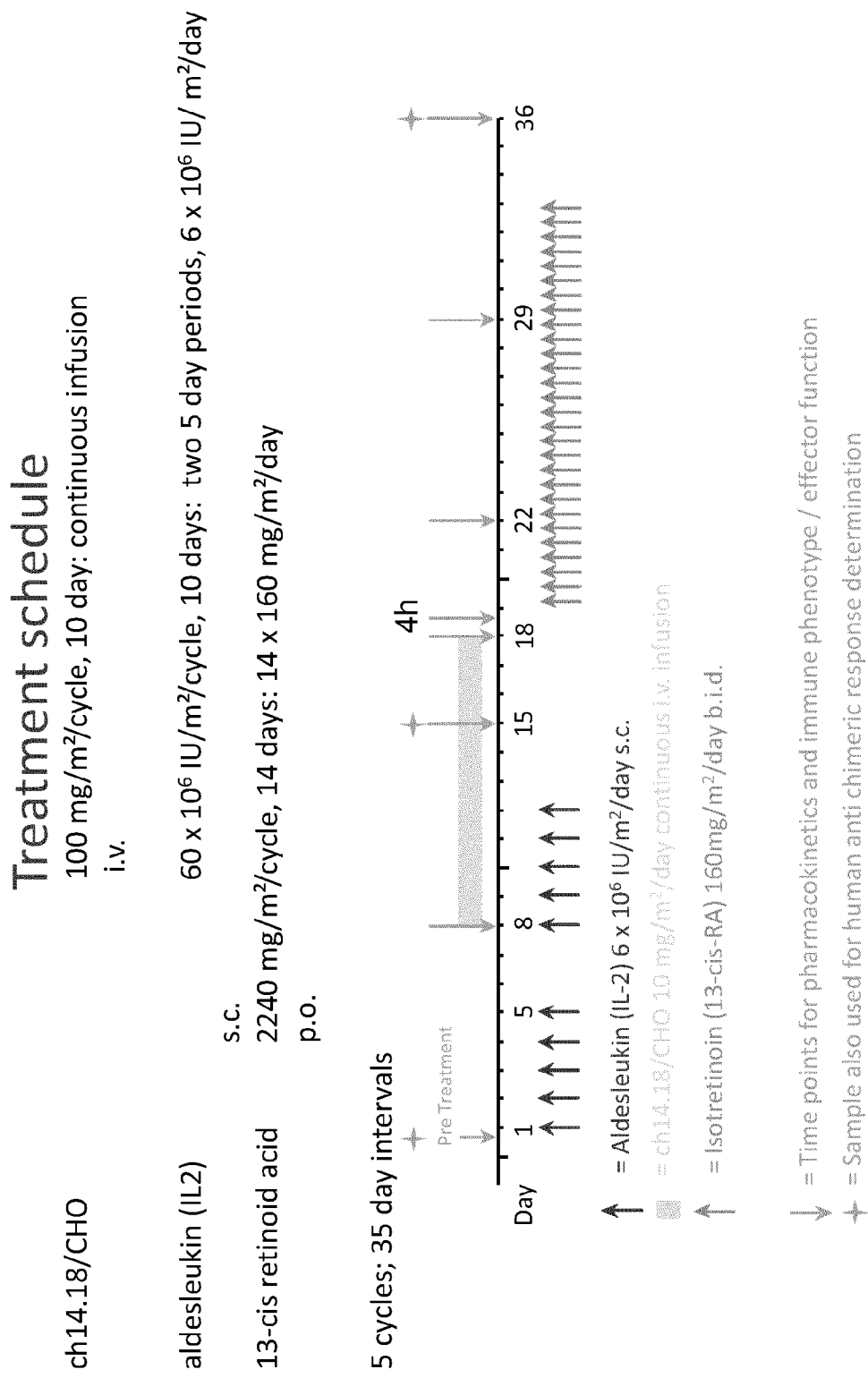
FIGS. 8 and 9 show examples of schematic treatment schedules for the treatment with a preparation comprising an anti-GD2 antibody combined with other treatments.
Figure 9:
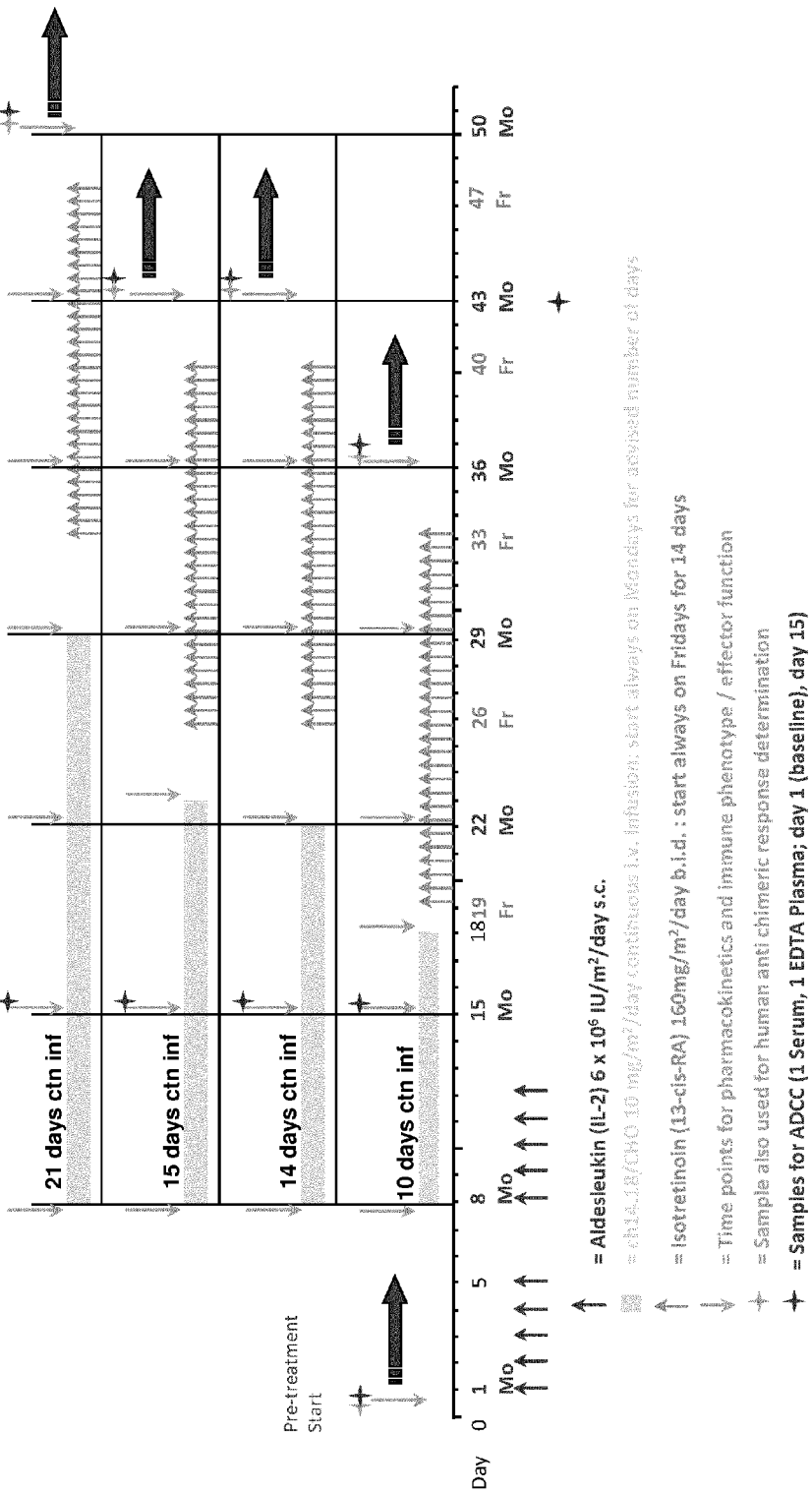

A "treatment period" with a specific preparation or treatment as used herein means the period of time in which said specific preparation or treatment is administered to the patient, i.e. the time period of subsequent treatment days. For example, if the preparation comprising a cytokine is administered for 5 consecutive days, followed by one or more days of no administration of the preparation comprising a cytokine, then the treatment period with the preparation comprising a cytokine comprises 5 days. In another example, if the preparation comprising the anti-GD2 antibody is administered continuously over 24 h for 10 consecutive days, followed by one or more days of no administration of the preparation comprising the anti-GD2 antibody, then the treatment period with the preparation comprising the anti-GD2 antibody comprises 10 days. In another example, if isotretinoin is administered twice a day for 14 days, followed by one or more days of no isotretinoin administration, then the treatment period with isotretinoin comprises 14 days. Any such treatment periods may be repeated and/or overlap. For example, the treatment schedules as depicted in FIGS. 8 and 9 comprise two 5-day treatment periods with IL-2, the second of which is overlapping with the 10-day (or 14-, 15-, or 21-day) treatment period with ch14.18 (APN311), followed by a 14-day treatment period with isotretinoin.

The terms "combined" or "combination" as used herein in relation to treatment periods shall mean that two or more treatment periods with the same and/or different drugs or treatments are comprised in one treatment cycle. Said two or more treatment periods with different drugs or treatments may partially or entirely overlap, or may not overlap. Any such treatment periods may be separated by an interval of no treatment with the same and/or different drugs or treatments.

The term "treatment cycle" as used herein means a course of one or more treatments or treatment periods that is repeated on a regular schedule with periods of rest in between. For example, a treatment given for one week followed by three weeks of rest is one treatment cycle. In one embodiment, one treatment cycle comprises one treatment period with the preparation comprising an anti-GD2 antibody. The treatment cycle may optionally further comprise one or more treatment periods with a cytokine, one or more treatment periods with a retinoid, and/or one or more treatment periods with an analgesic.

In one embodiment, one treatment cycle comprises 28 to 49 days, e.g. 28, 35, 42, or 49 days or any range in between these periods. The treatment cycle starts with the day when the patient first receives any of the treatments comprised in said cycle (day 1), e.g. the administration of an preparation comprising an anti-GD2 antibody, and/or the cytokine, and/or any other preparation or treatment.

The treatment period with the anti-GD2 antibody and/or with a cytokine may be followed by a treatment period with a retinoid (e.g. isotretinoin), either directly or with an interval of one or more days of no treatment, e.g. 1, 2, 3, 4, or 5 days of no treatment. In one embodiment, isotretinoin is administered orally twice a day in a dose of 160 mg/m$^2$/ day for 14 days, e.g. from day 19 to day 32 of the treatment cycle. The treatment period with isotretinoin may be followed by an interval of one or more days of no treatment, e.g. 1, 2, 3, 4, or 5 days of no treatment.

In one embodiment, the treatment cycle comprises two 5-day treatment periods with the cytokine, e.g. on days 1 to 5 and 8 to 12 of the treatment cycle, one 10-day treatment period with the anti-GD2 antibody (e.g. with 10 or 15 mg/m²/day to administer a dose of 100 or 150 mg/m²/cycle), e.g. on days 8 to 17 of the treatment cycle, and one 14-day treatment period with isotretinoin, e.g. on days 19 to 32 of the treatment cycle, followed by 3 days of no treatment, before the next cycle begins on day 36, which is then day 1 of the second treatment cycle.

In one embodiment, the treatment cycle comprises two 5-day treatment periods with the cytokine, e.g. on days 1 to 5 and 8 to 12 of the treatment cycle, one 14-day treatment period with the anti-GD2 antibody (e.g. with 7 or 15 mg/m²/day to administer a dose of 100 or 210 mg/m²/cycle), e.g. on days 8 to 21 of the treatment cycle, and one 14-day treatment period with isotretinoin, e.g. on days 26 to 39 of the treatment cycle, followed by 3 days of no treatment, before the next cycle begins on day 43, which is then day 1 of the second treatment cycle.

In one embodiment, the treatment cycle comprises two 5-day treatment periods with the cytokine, e.g. on days 1 to 5 and 8 to 12 of the treatment cycle, one 15-day treatment period with the anti-GD2 antibody (e.g. with 10 mg/m²/day to administer a dose of 150 mg/m²/cycle), e.g. on days 8 to 22 of the treatment cycle, and one 14-day treatment period with isotretinoin, e.g. on days 26 to 39 of the treatment cycle, followed by 3 days of no treatment, before the next cycle begins on day 43, which is then day 1 of the second treatment cycle.

In one embodiment, the treatment cycle comprises two 5-day treatment periods with the cytokine, e.g. on days 1 to 5 and 8 to 12 of the treatment cycle, one 21-day treatment period with the anti-GD2 antibody (e.g. with 7 or 10 mg/m²/day to administer a dose of 150 or 210 mg/m²/cycle), e.g. on days 8 to 28 of the treatment cycle, and one 14-day treatment period with isotretinoin, e.g. on days 33 to 46 of the treatment cycle, followed by 3 days of no treatment, before the next cycle begins on day 50, which is then day 1 of the second treatment cycle.

In one embodiment, the treatment cycle comprises one 3-day treatment period with the immunocytokine (e.g. APN301), e.g. on days to 6 of the treatment cycle, two treatment periods with the cytokine, e.g. GM-CSF, e.g. on days 1 and 2 and on 8 to 14 of the treatment cycle, and one 14-day treatment period with isotretinoin, e.g. on days 11 to 24 of the treatment cycle, followed by 4 days of no treatment, before the next cycle begins on day 29, which is then day 1 of the second treatment cycle.

In one embodiment, the treatment cycle comprises one 4-day treatment period with the preparation comprising the anti-GD2 antibody (e.g. ch14.18/SP2/0), for example administered in a dose of 25 mg/m²/day, on days 3 to 6 of a 24-day treatment cycle beginning with day 0 (if GM-CSF is used as cytokine), or on days 7 to 10 of a 32-day treatment cycle beginning with day 0 (if IL-2 is used as cytokine), for 5 cycles (e.g. the first with GM-CSF, the second with IL-2, the third with GM-CSF, the fourth with IL-2, and the fifth with GM-CSF); one or two treatment periods with a cytokine (e.g. GM-CSF at 250 micrograms/m²/day for 14 days, on days 0 to 13 of a treatment cycle beginning with day 0; or Aldesleukin (IL-2) in a dose of 3 MIU/m²/day on days 0 to 3 and 4.5 MIU/m²/day on days 7 to 10 of a treatment cycle beginning with day 0, and one treatment period with RA, e.g. isotretinoin on days 10 to 23 of a treatment cycle beginning with day 0 (if GM-CSF is used as cytokine), or on days 14 to 27 of a treatment cycle beginning with day 0 (if IL-2 is used as cytokine). In an embodiment, the treatment schedule is as specified in Table 2, 3 and/or 4.

The treatment cycle may be repeated, either identically or in an amended form, e.g. with a different dose or schedule, or with different additional treatments (e.g. with one or more other cytokines). Thus, the overall treatment time (i.e. the time period comprising all subsequent treatment cycles, or the overall continuous treatment period) may comprise at least 1, or 2 or more cycles, or up to 10 cycles. In one embodiment, the overall treatment time comprises 3, 4, 5, 6, 7, 8, 9, or 10 cycles. As described above, treatment cycles may comprise time periods of no treatment (intervals in which no treatment is administered to the patient, i.e. no antibody, no cytokine, no other drug). Thus, as used herein, the overall treatment time may also comprise said intervals of no treatment within treatment cycles.

In one embodiment, the 35, 42 or 49 day treatment cycle as specified above is repeated 4 or 5 times, so that the overall continuous treatment period comprises 5 or 6 treatment cycles.

Preferably the present invention is defined as follows:

Definition 1: A method for treating a GD2 positive cancer by administering a preparation comprising an anti-GD2 antibody to a patient as a continuous intravenous infusion over 24 hours per day.

Definition 2: A method according to definition 1, wherein the preparation comprising an anti-GD2 antibody is administered in a dose sufficient to induce tumor cell lysis (cytolysis threshold dose).

Definition 3: A method according to definition 2, wherein the cytolysis threshold dose is determined individually for each patient.

Definition 4: A method according to definitions 2 or 3, wherein the cytolysis threshold dose is determined by a complement dependent cytolysis assay.

Definition 5: A method according to definitions 2 or 3, wherein the cytolysis threshold dose is determined by a whole blood test.

Definition 6: A method according to any one of definitions 1 to 5, wherein the cytolysis threshold dose is the dose determined in a specific CDC assay or WBT to induce at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% of the maximal possible target cell lysis in that respective assay.

Definition 7: A method according to any one of definitions 1 to 6, wherein the cytolysis threshold dose is the dose determined in a specific CDC assay or WBT to induce 30%, 35%, 40%, 45%, 50%, 55%, 60%, 65%, 70%, 75%, 80%, 85%, 90%, 95%, or 100% of the maximal possible target cell lysis in that respective assay.

Definition 8: A method according to any one of definitions 1 to 7, wherein the cytolysis threshold dose is 470 to 1000, 470 to 10000, 1410 to 3000, or 2350 to 5000 ng/mL serum or plasma.

Definition 9: A method according to any one of definitions 1 to 8, wherein the cytolysis threshold dose is 2 to 250, 2 to 2500, 2 to 100, 5 to 200, 6 to 750, 6 to 7500, 10 to 1250, 10 to 12500, 6 to 300, 10 to 500, 15 to 600, or 25 to 1000 ng/mL whole blood.

Definition 10: A method according to any one of definitions 1 to 9, wherein the preparation comprising an anti-GD2 antibody is administered in a dose to achieve the cytolysis threshold dose in the patient's serum, plasma or whole blood within 1, 2, 3, or 4 days of the treatment with the preparation comprising an anti-GD2 antibody.

Definition 11: A method according to any one of definitions 1 to 10, wherein the threshold cytolysis is maintained even for one or more time periods within the overall treatment time, where the patient is not treated with the preparation comprising an anti-GD2 antibody.

Definition 12: A method according to any one of definitions 1 to 11, wherein the level of cytolysis is maintained over the entire treatment cycle.

Definition 13: A method according to any one of definitions 1 to 12, wherein the level of cytolysis is maintained over the overall treatment time.

Definition 14: A method according to any one of definitions 1 to 13, wherein the preparation comprising an anti-GD2 antibody is administered in in a daily dose of 1 to 30 mg/m$^2$, 1 to 35 mg/m$^2$, 1 to 50 mg/m$^2$, or 1 to 60 mg/m$^2$.

Definition 15: A method according to any one of definitions 1 to 14, wherein the preparation comprising an anti-GD2 antibody is administered in in a daily dose of 1, 2, 3, 4, 5, 6, 7, 7.5, 8, 9, 10, 12, 15, 20, 25, 30, 32, 35, 40, 45, 50, or 60 mg/m$^2$.

Definition 16: A method according to any one of definitions 1 to 15, wherein the preparation comprising an anti-GD2 antibody is administered for a treatment period until the predetermined overall patient dose has been administered.

Definition 17: A method according to any one of definitions 1 to 16, wherein the preparation comprising an anti-GD2 antibody is administered for a treatment period until a certain therapeutic effect has been reached.

Definition 18: A method according to any one of definitions 1 to 17, wherein the preparation comprising an anti-GD2 antibody is administered by using a mini-pump.

Definition 19: A method according to any one of definitions 1 to 18, wherein the anti-GD2 antibody is a chimeric or humanized antibody.

Definition 20: A method according to any one of definitions 1 to 19, wherein the anti-GD2 antibody is ch14.18/CHO or ch14.18/SP2/0.

Definition 21: A method according to any one of definitions 1 to 20, wherein the preparation comprising the anti-GD2 antibody is APN311 or APN301.

Definition 22: A method according to any one of definitions 1 to 21, wherein the preparation comprising an anti-GD2 antibody is administered in a dose of 7, 10, 15, or 25 mg/m$^2$/day.

Definition 23: A method according to any one of definitions 1 to 22, wherein the preparation comprising an anti-GD2 antibody is administered for 4, 10, 14, 15, or 21 consecutive days.

Definition 24: A method according to any one of definitions 1 to 23, wherein the preparation comprising an anti-GD2 antibody is administered for 3, 4, 5, or 6 treatment cycles.

Definition 25: A method according to any one of definitions 1 to 24, wherein the preparation comprising an anti-GD2 antibody is APN311 and is administered in a dose of 10 mg/m$^2$/day for 10 consecutive days for 6 treatment cycles.

Definition 26: A method according to any one of definitions 1 to 24, wherein the anti-GD2 antibody is ch14.18/SP2/0 and is administered in a dose of 25 mg/m$^2$/day for 4 consecutive days for 5 treatment cycles.

Definition 27: A method according to any one of definitions 1 to 26, wherein the administration of the preparation comprising an anti-GD2 antibody is preceded and/or accompanied by the administration of IL-2 and/or GM-CSF or another cytokine.

Definition 28: A method according to any one of definitions 1 to 27, wherein the administration period of the preparation comprising an anti-GD2 antibody may be followed by an administration period of isotretinoin or another retinoid.

Definition 29: A method according to any one of definitions 1 to 28, wherein the administration of the preparation comprising an anti-GD2 antibody is accompanied by the administration of morphine and/or one or more other analgesics.

Definition 30: A method according to any one of definitions 1 to 29, wherein the daily morphine dose administered during one or more days of continuous intravenous infusion of the antibody according to the invention and/or of all morphine treatment days is lower than the daily morphine dose during non-continuous administration of the antibody.

Definition 31: A method according to any one of definitions 1 to 30, wherein morphine is administered only for some but not all days on which the antibody is administered.

Definition 32: A method according to any one of definitions 1 to 31, wherein the morphine dose per treatment cycle administered during one or more treatment cycles comprising the continuous intravenous infusion of the antibody according to the invention is lower than the morphine dose per treatment cycle in a non-continuous infusion schedule.

Definition 33: A method according to any one of definitions 1 to 32, wherein the morphine dose of the overall treatment time is lower than the morphine dose of the overall treatment time in a non-continuous infusion schedule.

Definition 34: A method according to any one of definitions 1 to 33, wherein the morphine dose administered during one or more hours or days of continuous intravenous infusion of the antibody according to the invention and/or of all morphine treatment hours or days is lower than 50 mcg/kg/h, or lower than 30 mcg/kg/h.

Definition 35: A method according to any one of definitions 1 to 34, wherein the daily morphine dose administered during one or more days of continuous intravenous infusion of the antibody according to the invention and/or of all morphine treatment days is lower than 0.9, 0.72, 0.48, 0.38, 0.4375, and/or 0.205 mg/kg/day.

Definition 36: A method according to any one of definitions 1 to 35, wherein the dose of the one or more analgesics, especially morphine, is reduced within the overall treatment time, within a treatment cycle, during the antibody treatment period within a treatment cycle, from one antibody treatment day to the next antibody treatment day within a treatment cycle, and/or from one treatment cycle to the next.

Definition 37: A method according to any one of definitions 1 to 36, wherein the morphine dose is continuously reduced within a treatment cycle, during the antibody treatment period within a treatment cycle, and/or from one antibody treatment day to the next antibody treatment day within a treatment cycle.

Definition 38: An anti-GD2 antibody for use in a treatment according to any one of definitions 1 to 37.

Definition 39: Use of an anti-GD2 antibody in the preparation of a medicament for the treatment according to any one of definitions 1 to 37.

EXAMPLES

Example 1: APN311 and APN301 Sequences and Related Data

APN311 Sequence Data

TABLE 5

| Molecular Weight (MW) and pI (calculated) | | | | | |
|---|---|---|---|---|---|
| | pI[1] | MW [D][1] | No. of AS | Conditions | 2D-DIGE[2] |
| Antibody | 8.61 | 144701.10 | 1324 | non-reducing | x |
| Antibody (1/2) | 8.58 | 72359.56 | 662 | reducing | x |

TABLE 5-continued

| Molecular Weight (MW) and pI (calculated) | | | | | |
|---|---|---|---|---|---|
| | pI[1] | MW [D][1] | No. of AS | Conditions | 2D-DIGE[2] |
| Heavy Chain | 8.58 | 48306.59 | 442 | reducing | x |
| Light Chain | 8.48 | 24070.98 | 220 | reducing | x |

[1]Calculated via http://web.expasy.org/compute_pi/
[2]Due to the molecular weight of the dyes, shifts to slightly higher molecular weights are to be expected for 2D-DIGE Nucleotide Sequence (cDNA, Incl. Leader)

"TAG" works as a "stop codon" and therefore is not translated into the peptide sequence.

```
Light Chain (SEQ ID NO: 1):
  1 ATG GAA GCC CCA GCG CAG CTT CTC TTC CTC CTG CTA CTC TGG CTC CCA GAT ACC ACT GGA
 61 GAA ATA GTG ATG ACG CAG TCT CCA GCC ACC CTG TCT GTG TCT CCA GGG GAA AGA GCC ACC
121 CTC TCC TGC AGA TCT AGT CAG AGT CTT GTA CAC CGT AAT GGA AAC ACC TAT TTA CAT TGG
181 TAC CTG CAG AAG CCA GGC CAG TCT CCA AAG CTC CTG ATT CAC AAA GTT TCC AAC CGA TTT
241 TCT GGG GTC CCA GAC AGG TTC AGT GGC AGT GGA TCA GGG ACA GAT TTC ACA CTC AAG ATC
301 AGC AGA GTG GAG GCT GAG GAT CTG GGA GTT TAT TTC TGT TCT CAA AGT ACA CAT GTT CCT
361 CCG CTC ACG TTC GGT GCT GGG ACC AAG CTG GAG CTG AAA CGA ACT GTG GCT GCA CCA TCT
421 GTC TTC ATC TTC CCG CCA TCT GAT GAG CAG TTG AAA TCT GGA ACT GCC TCT GTT GTG TGC
481 CTG CTG AAT AAC TTC TAT CCC AGA GAG GCC AAA GTA CAG TGG AAG GTG GAT AAC GCC CTC
541 CAA TCG GGT AAC TCC CAG GAG AGT GTC ACA GAG CAG GAC AGC AAG GAC AGC ACC TAC AGC
601 CTC AGC AGC ACC CTG ACG CTG AGC AAA GCA GAC TAC GAG AAA CAC AAA GTC TAC GCC TGC
661 GAA GTC ACC CAT CAG GGC CTG AGC TCG CCC GTC ACA AAG AGC TTC AAC AGG GGA GAG TGT
721 TAG Heavy Chain (SEQ ID NO: 2):
  1 ATG GGA TGG ACC TGG ATC TTT ATT TTA ATC CTG TCG GTA ACT ACA GGT GTC CAC TCT GAG
 61 GTC CAA CTG CTG CAG TCT GGA CCT GAG CTG GAG AAG CCT GGC GCT TCA GTG ATG ATA TCC
121 TGC AAG GCT TCT GGT TCC TCA TTC ACT GGC TAC AAC ATG AAC TGG GTG AGG CAG AAC ATT
181 GGA AAG AGC CTT GAA TGG ATT GGA GCT ATT GAT CCT TAC TAT GGT GGA ACT AGC TAC AAC
241 CAG AAG TTC AAG GGC AGG GCC ACA TTG ACT GTA GAC AAA TCG TCC AGC ACA GCC TAC ATG
301 CAC CTC AAG AGC CTG ACA TCT GAG GAC TCT GCA GTC TAT TAC TGT GTA AGC GGA ATG GAG
361 TAC TGG GGT CAA GGA ACC TCA GTC ACC GTC TCC TCA GCC TCC ACC AAG GGC CCA TCG GTC
421 TTC CCC CTG GCA CCC TCC TCC AAG AGC ACC TCT GGG GGC ACA GCG GCC CTG GGC TGC CTG
481 GTC AAG GAC TAC TTC CCC GAA CCG GTG ACG GTG TCG TGG AAC TCA GGC GCC CTG ACC AGC
541 GGC GTG CAC ACC TTC CCG GCT GTC CTA CAG TCC TCA GGA CTC TAC TCC CTC AGC AGC GTG
601 GTG ACC GTG CCC TCC AGC AGC TTG GGC ACC CAG ACC TAC ATC TGC AAC GTG AAT CAC AAG
661 CCC AGC AAC ACC AAG GTG GAC AAG AGA GTT GAG CCC AAA TCT TGT GAC AAA ACT CAC ACA
721 TGC CCA CCG TGC CCA GCA CCT GAA CTC CTG GGG GGA CCG TCA GTC TTC CTC TTC CCC CCA
781 AAA CCC AAG GAC ACC CTC ATG ATC TCC CGG ACC CCT GAG GTC ACA TGC GTG GTG GTG GAC
841 GTG AGC CAC GAA GAC CCT GAG GTC AAG TTC AAC TGG TAC GTG GAC GGC GTG GAG GTG CAT
901 AAT GCC AAG ACA AAG CCG CGG GAG GAG CAG TAC AAC AGC ACG TAC CGT GTG GTC AGC GTC
961 CTC ACC GTC CTG CAC CAG GAC TGG CTG AAT GGC AAG GAG TAC AAG TGC AAG GTC TCC AAC
```

```
1021 AAA GCC CTC CCA GCC CCC ATC GAG AAA ACC ATC TCC AAA GCC AAA GGG CAG CCC CGA GAA

1081 CCA CAG GTG TAC ACC CTG CCC CCA TCC CGG GAG GAG ATG ACC AAG AAC CAG GTC AGC CTG

1141 ACC TGC CTG GTC AAA GGC TTC TAT CCC AGC GAC ATC GCC GTG GAG TGG GAG AGC AAT GGG

1201 CAG CCG GAG AAC AAC TAC AAG ACC ACG CCT CCC GTG CTG GAC TCC GAC GGC TCC TTC TTC

1261 CTC TAT AGC AAG CTC ACC GTG GAC AAG AGC AGG TGG CAG CAG GGG AAC GTC TTC TCA TGC

1321 TCC GTG ATG CAT GAG GCT CTG CAC AAC CAC TAC ACG CAG AAG AGC CTC TCC CTG TCC CCG

1381 GGT AAA TGA
``` nucleotide 1 to 60 (striked out): leader sequence
last nucleotide (striked out): stop codon
Peptide Sequence (Incl. Signal Peptide)
The signal peptide is split off during post translational processing and is not part of the final recombinant protein anymore.

```
Light Chain (SEQ ID NO: 3):
  1  M E A P A Q L L F L L L L W L P D T T G
 21  E I V M T Q S P A T L S V S P G E R A T
 41  L S C R S S Q S L V H R N G N T Y L H W
 61  Y L Q K P G Q S P K L L I H K V S N R F
 81  S G V P D R F S G S G S G T D F T L K I
101  S R V E A E D L G V Y F C S Q S T H V P
121  P L T F G A G T K L E L K R T V A A P S
141  V F I F P P S D E Q L K S G T A S V V C
161  L L N N F Y P R E A K V Q W K V D N A L
181  Q S G N S Q E S V T E Q D S K D S T Y S
201  L S S T L T L S K A D Y E K H K V Y A C
221  E V T H Q G L S S P V T K S F N R G E C Heavy Chain (SEQ ID NO: 4):
  1  M G W T W I F I L I L S V T T G V H S E
 21  V Q L L Q S G P E L E K P G A S V M I S
 41  C K A S G S S F T G Y N M N W V R Q N I
 61  G K S L E W I G A I D P Y Y G G T S Y N
 81  Q K F K G R A T L T V D K S S S T A Y M
101  H L K S L T S E D S A V Y Y C V S G M E
121  Y W G Q G T S V T V S S A S T K G P S V
141  F P L A P S S K S T S G G T A A L G C L
161  V K D Y F P E P V T V S W N S G A L T S
181  G V H T F P A V L Q S S G L Y S L S S V
201  V T V P S S S L G T Q T Y I C N V N H K
221  P S N T K V D K R V E P K S C D K T H T
241  C P P C P A P E L L G G P S V F L F P P
261  K P K D T L M I S R T P E V T C V V V D
281  V S H E D P E V K F N W Y V D G V E V H
301  N A K T K P R E E Q Y N S T Y R V V S V
321  L T V L H Q D W L N G K E Y K C K V S N
341  K A L P A P I E K T I S K A K G Q P R E
361  P Q V Y T L P P S R E E M T K N Q V S L
381  T C L V K G F Y P S D I A V E W E S N G
401  Q P E N N Y K T T P P V L D S D G S F F
421  L Y S K L T V D K S R W Q Q G N V F S C
441  S V M H E A L H N H Y T Q K S L S L S P
461  G K
``` amino acid 1 to 20 (striked out): leader sequence
APN301 Sequence Data

TABLE 6

Molecular Weight (MW) and pI (calculated)

| | pI[1] | MW [D][1] | No. of AS | Conditions | 2D-DIGE[2] |
|---|---|---|---|---|---|
| Immunocytokine | 8.52 | 175741.35 | 1592 | non-reducing | x |
| Antibody | 8.61 | 144941.37 | 1326 | non-reducing | |
| Immunocytokine (1/2) | 8.49 | 87879.68 | 796 | reducing | x |
| Antibody (1/2) | 8.57 | 72479.69 | 663 | reducing | |
| Heavy Chain + IL-2 | 8.47 | 63861.72 | 576 | reducing | x |
| Heavy Chain | 8.59 | 48461.73 | 443 | reducing | |
| Light Chain | 8.27 | 24035.97 | 220 | reducing | x |
| IL-2 | 7.05 | 15418.01 | 133 | reducing | |

[1] Calculated via http://web.expasy.org/compute pi/
[2] Due to the molecular weight of the dyes, shifts to slightly higher molecular weights are to be expected for 2D-DIGE
3) IL-2 should not be cleaved off the immunocytokine under reducing condition, as it is bound covalently via a linker to the Fc portion and therefore the heavy chain, antibody (1/2) and the antibody should not be present on a 2D-DIGE Nucleotide Sequence (cDNA, Incl. Leader)
"TAG" and "TGA" work as "stop codons" and therefore are not translated into the peptide sequence.

```
Light Chain (SEQ ID NO: 5):
  1  ATG AAG TTG CCT GTT AGG CTG TTG GTG CTG ATG TTC TGG ATT CCT GCT TCC TTA AGC GAC
 61  GTG GTG ATG ACC CAG ACC CCC CTG TCC CTG CCC GTG ACC CCC GGC GAG CCC GCC TCC ATC
```

```
121 TCC TGC AGA TCT AGT CAG AGT CTT GTA CAC CGT AAT GGA AAC ACC TAT TTA CAT TGG TAC
181 CTG CAG AAG CCA GGC CAG TCT CCA AAG CTC CTG ATT CAC AAA GTT TCC AAC CGA TTT TCT
241 GGG GTC CCA GAC AGG TTC AGT GGC AGT GGA TCA GGG ACA GAT TTC ACA CTC AAG ATC AGC
301 AGA GTG GAG GCT GAG GAT CTG GGA GTT TAT TTC TGT TCT CAA AGT ACA CAT GTT CCT CCG
361 CTC ACG TTC GGT GCT GGG ACC AAG CTG GAG CTG AAA CGA ACT GTG GCT GCA CCA TCT GTC
421 TTC ATC TTC CCG CCA TCT GAT GAG CAG TTG AAA TCT GGA ACT GCC TCT GTT GTG TGC CTG
481 CTG AAT AAC TTC TAT CCC AGA GAG GCC AAA GTA CAG TGG AAG GTG GAT AAC GCC CTC CAA
541 TCG GGT AAC TCC CAG GAG AGT GTC ACA GAG CAG GAC AGC AAG GAC AGC ACC TAC AGC CTC
601 AGC AGC ACC CTG ACG CTG AGC AAA GCA GAC TAC GAG AAA CAC AAA GTC TAC GCC TGC GAA
661 GTC ACC CAT CAG GGC CTG AGC TCG CCC GTC ACA AAG AGC TTC AAC AGG GGA GAG TGT ~~TAG~~
```

Heavy Chain (incl. IL-2; SEQ ID NO: 6):
```
   1 ~~ATG AAG TTG CCT GTT AGG CTG TTG GTG CTG ATG TTC TGG ATT CCT GCT TCC TTA AGC~~ GAG
  61 GTG CAG CTG GTG CAG TCC GGC GCC GAG GTG GAG AAG CCC GGC GCC TCC GTG AAG ATC TCC
 121 TGC AAG GCC TCC GGC TCC TCC TTC ACC GGC TAC AAC ATG AAC TGG GTG CGC CAG AAC ATC
 181 GGC AAG TCC CTG GAG TGG ATC GGC GCC ATC GAC CCC TAC TAC GGC GGC ACC TCC TAC AAC
 241 CAG AAG TTC AAG GGC CGC GCC ACC CTG ACC GTG GAC AAG TCC ACC TCC ACC GCC TAC ATG
 301 CAC CTG AAG TCC CTG CGC TCC GAG GAC ACC GCC GTG TAC TAC TGC GTG TCC GGC ATG GAG
 361 TAC TGG GGC CAG GGC ACC TCC GTG ACC GTG TCC TCC GCC TCC ACC AAG GGC CCA TCG GTC
 421 TTC CCC CTG GCA CCC TCC TCC AAG AGC ACC TCT GGG GGC ACA GCG GCC CTG GGC TGC CTG
 481 GTC AAG GAC TAC TTC CCC GAA CCG GTG ACG GTG TCG TGG AAC TCA GGC GCC CTG ACC AGC
 541 GGC GTG CAC ACC TTC CCG GCT GTC CTA CAG TCC TCA GGA CTC TAC TCC CTC AGC AGC GTG
 601 GTG ACC GTG CCC TCC AGC AGC TTG GGC ACC CAG ACC TAC ATC TGC AAC GTG AAT CAC AAG
 661 CCC AGC AAC ACC AAG GTG GAC AAG AGA GTT GAG CCC AAA TCT TGT GAC AAA ACT CAC ACA
 721 TGC CCA CCG TGC CCA GCA CCT GAA CTC CTG GGG GGA CCG TCA GTC TTC CTC TTC CCC CCA
 781 AAA CCC AAG GAC ACC CTC ATG ATC TCC CGG ACC CCT GAG GTC ACA TGC GTG GTG GTG GAC
 841 GTG AGC CAC GAA GAC CCT GAG GTC AAG TTC AAC TGG TAC GTG GAC GGC GTG GAG GTG CAT
 901 AAT GCC AAG ACA AAG CCG CGG GAG GAG CAG TAC AAC AGC ACG TAC CGT GTG GTC AGC GTC
 961 CTC ACC GTC CTG CAC CAG GAC TGG CTG AAT GGC AAG GAG TAC AAG TGC AAG GTC TCC AAC
1021 AAA GCC CTC CCA GCC CCC ATC GAG AAA ACC ATC TCC AAA GCC AAA GGG CAG CCC CGA GAA
1081 CCA CAG GTG TAC ACC CTG CCC CCA TCC CGG GAG GAG ATG ACC AAG AAC CAG GTC AGC CTG
1141 ACC TGC CTG GTC AAA GGC TTC TAT CCC AGC GAC ATC GCC GTG GAG TGG GAG AGC AAT GGG
1201 CAG CCG GAG AAC AAC TAC AAG ACC ACG CCT CCC GTG CTG GAC TCC GAC GGC TCC TTC TTC
1261 CTC TAT AGC AAG CTC ACC GTG GAC AAG AGC AGG TGG CAG CAG GGG AAC GTC TTC TCA TGC
1321 TCC GTG ATG CAT GAG GCT CTG CAC AAC CAC TAC ACG CAG AAG AGC CTC TCC CTG TCC CCG
1381 GGT AAA GCC CCA ACT TCA AGT TCT ACA AAG AAA ACA CAG CTG CAA CTG GAG CAT CTC CTG
1441 CTG GAT CTC CAG ATG ATT CTG AAT GGA ATT AAC AAC TAC AAG AAT CCC AAA CTC ACC AGG
1501 ATG CTC ACA TTC AAG TTC TAC ATG CCC AAG AAG GCC ACA GAG CTC AAA CAT CTC CAG TGT
1561 CTA GAG GAG GAA CTC AAA CCT CTG GAG GAA GTG CTA AAC CTC GCT CAG AGC AAA AAC TTC
1621 CAC TTA AGA CCT AGG GAC TTA ATC AGC AAT ATC AAC GTA ATA GTT CTG GAA CTA AAG GGA
1681 TCC GAA ACA ACA TTC ATG TGT GAA TAT GCT GAT GAG ACA GCA ACC ATT GTA GAA TTT CTG
1741 AAC AGA TGG ATT ACC TTT TGT CAA AGC ATC ATC TCA ACA CTA ACT ~~TGA~~
``` nucleotide 1 to 57 (striked out): leader sequence
nucleotide 1387 to 1385: IL-2 sequence last nucleotide (striked out): stop codon
Peptide Sequence (Incl. Signal Peptide)

The signal peptide is split off during post translational processing and is not part of the final recombinant protein anymore.

```
Light Chain (SEQ ID NO: 7):
  1   M K L P V R L L V L M F W I P A S L S D
 21   V V M T Q T P L S L P V T P G E P A S I
 41   S C R S S Q S L V H R N G N T Y L H W Y
 61   L Q K P G Q S P K L L I H K V S N R F S
 81   G V P D R F S G S G S G T D F T L K I S
101   R V E A E D L G V Y F C S Q S T H V P P
121   L T F G A G T K L E L K R T V A A P S V
141   F I F P P S D E Q L K S G T A S V V C L
161   L N N F Y P R E A K V Q W K V D N A L Q
181   S G N S Q E S V T E Q D S K D S T Y S L
201   S S T L T L S K A D Y E K H K V Y A C E
221   V T H Q G L S S P V T K S F N R G E C Heavy Chain (incl. IL-2; SEQ ID NO: 8):
  1   M K L P V R L L V L M F W I P A S L S E
 21   V Q L V Q S G A E V E K P G A S V K I S
 41   C K A S G S S F T G Y N M N W V R Q N I
 61   G K S L E W I G A I D P Y Y G G T S Y N
 81   Q K F K G R A T L T V D K S T S T A Y M
101   H L K S L R S E D T A V Y Y C V S G M E
121   Y W G Q G T S V T V S S A S T K G P S V
141   F P L A P S S K S T S G G T A A L G C L
161   V K D Y F P E P V T V S W N S G A L T S
181   G V H T F P A V L Q S S G L Y S L S S V
201   V T V P S S S L G T Q T Y I C N V N H K
221   P S N T K V D K R V E P K S C D K T H T
241   C P P C P A P E L L G G P S V F L F P P
261   K P K D T L M I S R T P E V T C V V V D
281   V S H E D P E V K F N W Y V D G V E V H
301   N A K T K P R E E Q Y N S T Y R V V S V
321   L T V L H Q D W L N G K E Y K C K V S N
341   K A L P A P I E K T I S K A K G Q P R E
361   P Q V Y T L P P S R E E M T K N Q V S L
381   T C L V K G F Y P S D I A V E W E S N G
401   Q P E N N Y K T T P P V L D S D G S F F
421   L Y S K L T V D K S R W Q Q G N V F S C
441   S V M H E A L H N H Y T Q K S L S L S P
461   G K A P T S S S T K K T Q L Q L E H L L
481   L D L Q M I L N G I N N Y K N P K L T R
501   M L T F K F Y M P K K A T E L K H L Q C
521   L E E E L K P L E E V L N L A Q S K N F
541   H L R P R D L I S N I N V I V L E L K G
561   S E T T F M C E Y A D E T A T I V E F L
581   N R W I T F C Q S I I S T L T
``` amino acid 1 to 19 (striked out): leader sequence
amino acid 463 to 595: IL-2 sequence Two GMP compliant batches of the ch14.18/CHO (APN311) antibody have been produced. These two batches of the drug that have been produced are Lot T651204-A (containing 4.3 ml (4.6 mg/ml) antibody) and Lot T900310-A (containing 4.5 ml (4.5 mg/ml) antibody. The APN311 monoclonal antibody bulk preparation is manufactured as a concentrate for the preparation of IV infusions.

TABLE 7

Composition of the final APN311 preparation

| | |
|---|---|
| Product Name | Mouse-human chimeric monoclonal anti-GD2 IgG1 antibody (ch14.18/CHO; APN311) |
| Content | 4.25-4.75 mg/ml (the exact content per mL may slightly vary from lot to lot and is given on each vial) |
| Buffer | 20 mM histidine, 5% saccharose, 0.01% Tween 20, WFI |
| pH Value | 5.5-6.5 |
| Excipient | None |

Preparation Guide

The antibody must be prepared under sterile conditions. The appropriate volume of ch14.18/CHO antibody (APN311) should be withdrawn from the vials. It is recommended that the antibody solution is filtered (0.2 to 1.2 µm) before injection into the patient either by using an in-line filter during infusion (as some centres do routinely) or by filtering the solution with a particle filter (e.g. filter Nr. MF1830, Impromediform, Germany). The volume of the antibody is added to an infusion bag containing 100 ml NaCl 0.9% and 5 ml human albumin 20%.

Calculation of the Quantity of ch14.18/CHO (APN311) to be Diluted

The amount of ch14.18/CHO (APN311) to be administered is calculated as follows: ☐Dosage: 10 mg/m²/day, day 8-17, as 24 h infusion.

Example calculation: If a patient has a body surface area (BSA) of 0.7, he/she needs 7 mg (10×0.7) per day, or 70 mg for ten treatment days (one cycle).

Example 2: CDC Assay Method

Principle for CDC (Complement Dependent Cytotoxicity)
Induction of tumor cell cytotoxicity of normal human serum or plasma in the presence of APN301 or APN311, or of patients' serum or plasma after infusion of one of these antibodies, to the GD2 antigen positive LAN-1 neuroblastoma cancer cell line (target cells) was determined in a $^{51}$Chromium release assay.

The target cells were incubated with $Na_2^{51}Cr(VI)O_4$, which permeates the cell membrane and binds to cytoplasmatic proteins in the reduced Cr-III-valent form, thereby not leaking out anymore of an intact cell. When these cells are lysed after incubation with serum or plasma and antibodies or patients' serum or plasma, radioactivity is released into the supernatant dependent on the lytic capacity in the tested samples.

Spontaneous background lysis and total lysis (maximally achievable cell lysis or maximal possible target cell lysis) by a surfactant were determined in each individual experiment. After subtracting spontaneous lysis, the lysis induced by the tested samples was calculated as % of total lysis.

Serum or Plasma Sampling:

Whole blood from normal human donors or from patients was sampled using heparinized vacutainer vials for plasma or serum clotting vials for serum. Vials were centrifuged at 2000 g for 20 minutes. The supernatant plasma or serum could be used immediately for the assay or stored at −20° C. (no thawing and re-freezing allowed).

Labeling of Target Cells with $^{51}$Cr:

LAN-1 cells were cultivated in RPMI 1640 with 10% heat inactivated FCS. The day preceding the assay they were transferred into fresh flasks and fresh medium.

The assay was carried out in a 96-well flat bottom cell culture plate, using $4\times10^4$ labeled cells per well with an activity of 800 nCi $^{51}$Cr per well.

The needed amount of cells was harvested from the culture flasks, the suspension centrifuged and re-suspended in 1 ml of PBS def. with 0.1% EDTA and 1% FCS. The calculated volume of the $^{51}$Cr solution was added, cells were incubated for 90 minutes at 37° C. and 5% $CO_2$ under gentle rotation of the tube.

Then the cell suspension was washed twice with cell culture medium to remove radioactivity from outside the cells. This medium contained additionally 100 U/ml penicillin G and 100 μg/ml streptomycin sulphate. The pellet of labeled cells after the washing steps was resuspended to the wanted concentration of $4\times10^5$ cells per ml.

Assay Procedure:

For the assessment of cytolytic capacity of antibodies, the following was pipetted:

50 μl of the samples (antibody dilutions)
100 μl 1:4 pre-diluted normal human serum or plasma
100 μl $^{51}$Cr labeled cell suspension ($4\times10^5$ per ml)

For the assessment of cytolytic capacity of patients' plasma or serum, the following was pipetted:

50 μl medium
100 μl 1:4 pre-diluted patients' plasma or serum
100 μl $^{51}$Cr labeled cell suspension ($4\times10^5$ per mL)

Assay plates for CDC were incubated in a $CO_2$ incubator at 37° C., 5% $CO_2$, for 4 hours, or when compared directly to a WBT, for 20 hours.

Then the supernatants of each well are harvested using harvesting frames with absorption cartridges and a harvesting press (skatron). These cartridges soaked with the cell supernatants are transferred into counting vials of the gamma counter. Radioactivity, which is proportional to the release of chromium after a damage of the labeled target cells, is measured from all samples and expressed in counts per minute (cpm). Results are calculated as % lysis subtracting the cpms of spontaneous lysis from all sample values and relating to the cpm of the maximally achievable lysis with a surfactant which is 100%.

$$\frac{100 \times (cpm \text{ sample minus } cpm \text{ spontaneous lysis})}{cpm \text{ maximal lysis minus spontaneous lysis}} = \% \text{ lysis of samples}$$

The above described CDC assay method has been used for the results as shown in FIGS. 1, 2, 3, and 5.

A similar CDC assay method has been used for the results as shown in FIG. 7, however, calcein has been used as label for the LAN-1 cells instead of chromium.

Example 3: WBT Method

Principle for WBT (Whole Blood Test):

Induction of tumor cell cytotoxicity of normal human whole blood in the presence of APN301 or APN311, or of patients' whole blood after infusion of one of these antibodies, to the GD2 antigen positive LAN-1 neuroblastoma cancer cell line (target cells) was determined in a $^{51}$Chromium release assay.

The target cells were incubated with $Na_2^{51}Cr(VI)O_4$, which permeates the cell membrane and binds to cytoplasmatic proteins in the reduced Cr-III-valent form, thereby not leaking out of intact cells anymore. When these cells are lysed after incubation with whole blood and antibodies or patients' whole blood, radioactivity is released into the supernatant dependent on the lytic capacity in the tested samples.

Spontaneous background lysis and total lysis (maximally achievable lysis or maximal possible target cell lysis) by a surfactant were determined in each individual experiment. After subtracting spontaneous lysis, the lysis induced by the tested samples was calculated as % of total lysis.

Blood Sampling:

Whole blood from normal human donors or from patients was sampled using heparinized vacutainer vials.

Labeling of Target Cells with $^{51}$Cr:

LAN-1 cells were cultivated in RPMI 1640 with 10% heat inactivated FCS. The day preceding the assay they were transferred into fresh flasks and fresh medium.

The assay was carried out in a 96-well flat bottom cell culture plate, using $4\times10^4$ labeled cells per well with an activity of 800 nCi $^{51}$Cr per well.

The needed amount of cells was harvested from the culture flasks, the suspension centrifuged and re-suspended in 1 ml of PBS def. with 0.1% EDTA and 1% FCS. The calculated volume of the $^{51}$Cr solution was added, cells were incubated for 90 minutes at 37° C. and 5% $CO_2$ under gentle rotation of the tube.

Then the cell suspension was washed twice with cell culture medium to remove radioactivity from outside the cells. This medium contained additionally 100 U/ml penicillin G and 100 μg/ml streptomycin sulfate. The pellet of labeled cells after the washing steps was re-suspended to the wanted concentration of $4\times10^5$ cells per ml.

Assay Procedures:

For the assessment of cytolytic capacity of antibodies the following was pipetted:

50 μl of the samples (antibody dilutions)
100 μl 1:2 pre-diluted normal human whole blood
100 μl $^{51}$Cr labeled cell suspension ($4\times10^5$ per ml)

For the assessment of cytolytic capacity of patients' whole blood the following was pipetted:

50 μl medium
100 μl 1:2 pre-diluted patient's blood
100 μl $^{51}$Cr labeled cell suspension ($4\times10^5$ per ml)

Assay plates are incubated in a $CO_2$ incubator at 37° C., 5% $CO_2$, for 20 hours.

Then the supernatants of each well are harvested using harvesting frames with absorption cartridges and a harvesting press (skatron). These cartridges soaked with the cell supernatants are transferred into counting vials of the gamma counter. Radioactivity which is proportional to the release of chromium after a damage of the labelled target cells is measured from all samples and expressed in counts per minute (cpm). Results are calculated as % lysis subtracting the cpms of spontaneous lysis from all sample values and relating to the cpm of the maximally achievable lysis with a surfactant which is 100%.

$$\frac{100 \times (cpm \text{ sample minus } cpm \text{ spontaneous lysis})}{cpm \text{ maximal lysis minus spontaneous lysis}} = \% \text{ lysis of samples}$$

The above described WBT method has been used for the results as shown in FIGS. 1, 2, 3, and 4.

Example 4: Patient Treatment with a Continuous Intravenous Infusion of a Preparation Comprising an Anti-GD2 Antibody In a compassionate use setting of the treatment with ch14.18/CHO (APN311) in 41 patients with relapsed or refractory neuroblastoma, a continuous infusion modality has been used in order to possibly reduce the pain always associated with anti-GD2 antibody immunotherapy, in conjunction with s.c. IL2 and isotretinoin. Clinical responses were determined by local physicians based on evaluations of metaiodobenzylguanidine scintigraphy (mIBG), magnetic resonance imaging (MRI) or X-ray computed tomography (CT), bone marrow histology (assessed by aspirate or trephine biopsy) and catecholamines.

mIBG: 31 out of 41 patients had disease detected in mIBG before immunotherapy.

5 of these 31 patients (16%) had a complete response (CR), 7 (23%) had a partial response (PR), 4 (13%) had stable disease (SD) and 13 (42%) had progressive disease (PD). 2 patients (6%) are not evaluable. For one of them no mIBG examinations after immunotherapy were available, the other patient had the remaining tumor removed by surgery before restaging assessments after immunotherapy were done.

Overall, in 12 out of 31 patients (39%) with detectable disease in mIBG before immunotherapy a response (CR or PR) was detected after immunotherapy.

Furthermore, in 3 out of the 13 patients with PD after completion of immunotherapy (23%), a PR was detected after the 3rd immunotherapy cycle.

MRI/CT: 13 out of 41 patients had detectable disease in MRI or CT in soft tissue before immunotherapy.

One additional patient with a positive MRI at baseline was not evaluable as the remaining tumor was completely resected before final restaging assessments. After 3 immunotherapy cycles this patient had SD.

5 of the 13 patients with detectable disease in MRI or CT before immunotherapy (38%) had a PR, 4 (31%) had SD and 3 (23%) had PD. Evaluation of one patient (8%) is pending.

Bone marrow: 19 out of 41 patients had detectable disease in bone marrow before immunotherapy. 4 of these 19 patients (21%) showed a response after immunotherapy in the respective tests. Additionally, in 6 patients (32%) a response was detected after 3 immunotherapy cycles. PD, however, was noticed in 4 of these patients in other examinations after 3 cycles, and in 2 of these patients at the end of the immunotherapy.

Catecholamines: 18 out of 41 patients had increased catecholamine levels (Vanillyl mandelic acid (VMA) and/or Homovanillic acid (HVA)) before immunotherapy. In 7 of these 18 patients (39%) normal catecholamine levels were detected after 3 cycles of immunotherapy and/or after completion of immunotherapy.

Figure 10:
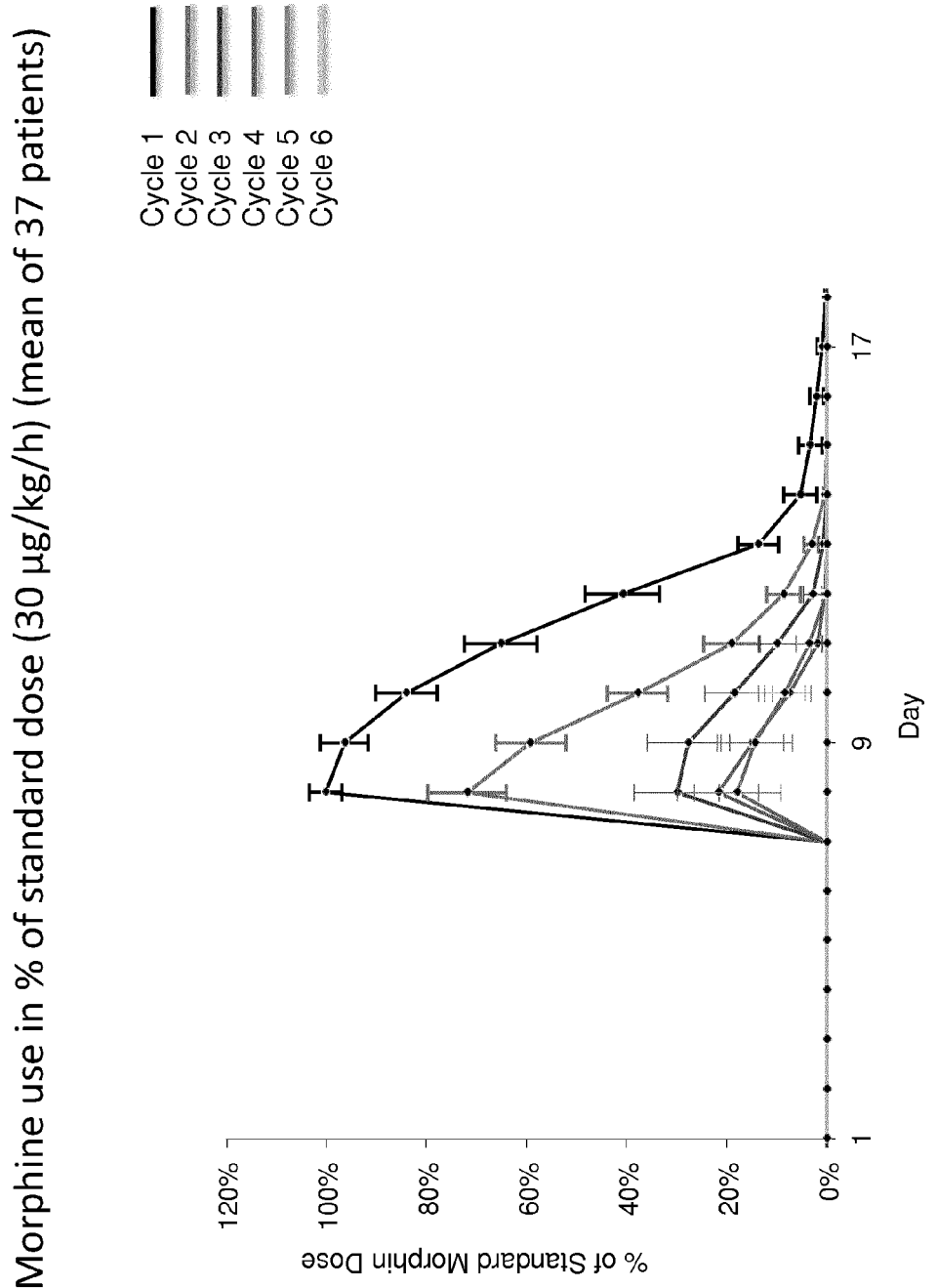
FIG. 10 shows the morphine use in % of the prescribed standard infusion rate (30 mcg/kg/h) during APN311 continuous infusions of 37 patients (mean values). Antibody infusions were always initiated on Day 8.

In addition to these marked response rates observed in the relapsed/refractory patients treated under a compassionate use setting by the continuous infusion modality, in all of these patients an impressive reduction of the pain side effect was noticed, allowing to substantially reduce or even completely avoid treatment with morphine:

The standard dose of i.v. morphine for this schedule is 30 μg/kg/h. In patients receiving ch14.18/CHO (APN311) continuous infusions, significantly less i.v. morphine was used compared to patients who receive ch14.18/CHO (APN311) bolus infusions. In many patients it was even possible to discontinue i.v. morphine completely and to treat pain with oral Gabapentin only. The morphine use during ch14.18/CHO (APN311) continuous infusions is displayed in FIG. 10 and Table 9. Antibody infusions were always initiated on Day 8. The actual morphine dose (mean of 37 patients) per overall treatment time (comprising all 6 treatment cycles) was 5.4 mg/kg compared to the prescribed morphine dose of 13.5 mg/kg of a previous phase I clinical study (0.9 mg/kg/day, infused over 8 h per day for 5 days per cycle, 3 cycles), and compared to 10 mg/kg of an ongoing phase III clinical study, both with non-continuous antibody infusion schedules (0.48 mg/kg/day on the first day and 0.38 mg/kg/day on the subsequent treatment days, infused over 8 h per day for 5 days per cycle, 5 cycles).

In addition, a Phase I/II study administering APN311 by continuous infusion combined with subcutaneous aldesleukin (IL2) in patients with primary refractory or relapsed neuroblastoma) has been set up to
- reduce the toxicity (pain) profile whilst maintaining immunomodulatory efficacy of ch14.18/CHO mAb (APN311) treatment in combination with a fixed dose of s.c. IL2.
- reduce the toxicity (pain) by establishing a continuous infusion scheme over 10 to 21 days at up to three dose levels (total doses: 100 mg/m$^2$-150 mg/m$^2$-200 mg/m$^2$).
- Improve patient compliance.
- Keep or even improve efficacy of immune therapy.

Preliminary results from this Phase I/II study show that the use of opioids, especially morphine, to control the massive incapacitating pain frequently occurring during the treatment with GD2 specific antibodies (including APN311) is significantly lower in these patients already during the first infusion cycles. From the 3$^{rd}$ cycle onwards it may be even possible to completely refrain from the standard morphine administration since patients will not require it due to the increased tolerability of the medication due to the improved application scheme.

The significantly reduced doses of morphine cause less of the opioid treatment related adverse effects and therefore even allow an out-patient treatment setting, which in turn will positively influence the ability of the pediatric patients to follow the normal lifestyle of children, e.g. ability to play and attend school, etc.

TABLE 8

Blood samples analysed with a WBT shown in FIGS. 11 to 16.

| patient | day of treatment (within the treatment cycle) | cycle |
|---|---|---|
| MJ | 15 | I |
|  | 8 | II |
|  | 10 | II |

TABLE 8-continued

Blood samples analysed with a WBT shown in FIGS. 11 to 16.

| patient | day of treatment (within the treatment cycle) | cycle |
|---|---|---|
| NG | before | — |
|  | 8 | I |
|  | 10 | I |
|  | 15 | I |
| JK | 8 | III |
|  | 10 | III |
|  | 15 | III |
| MM | 15 | III |
| GA | 8 | V |
|  | 10 | V |
| CJJ | 10 | V |

Blood samples taken at the beginning (i.e. on the first day) of the treatment period with APN311 (corresponding to day 8 of the treatment cycle) were taken prior to the start of the APN311 treatment.

TABLE 9

Morphine administration

| | Cycle | Day 8 | Day 9 | Day 10 | Day 11 | Day 12 | Day 13 | Day 14 | Day 15 | Day 16 | Day 17 | dose per cycle in mg/kg |
|---|---|---|---|---|---|---|---|---|---|---|---|---|
| % of standard infus. rate | 1 | 100% | 96% | 84% | 65% | 41% | 14% | 5% | 3% | 2% | 1% | |
| infusion rate in mcg/kg/h | | 30.04 | 28.93 | 25.19 | 19.56 | 12.26 | 4.10 | 1.60 | 1.00 | 0.60 | 0.29 | |
| daily dose in mg/kg | | 0.72 | 0.69 | 0.60 | 0.47 | 0.29 | 0.10 | 0.04 | 0.02 | 0.01 | 0.01 | 2.97 |
| % of standard infus. rate | 2 | 72% | 59% | 38% | 19% | 9% | 3% | 0% | 0% | 0% | 0% | |
| infusion rate in mcg/kg/h | | 21.61 | 17.13 | 9.53 | 3.73 | 1.06 | 0.13 | 0.01 | 0 | 0 | 0 | |
| daily dose in mg/kg | | 0.52 | 0.41 | 0.23 | 0.09 | 0.03 | 0.00 | 0.00 | 0 | 0 | 0 | 1.28 |
| % of standard infus. rate | 3 | 30% | 28% | 18% | 10% | 3% | 1% | 0% | 0% | 0% | 0% | |
| infusion rate in mcg/kg/h | | 9.01 | 8.10 | 4.53 | 1.96 | 0.37 | 0.04 | 0 | 0 | 0 | 0 | |
| daily dose in mg/kg | | 0.22 | 0.19 | 0.11 | 0.05 | 0.01 | 0.00 | 0 | 0 | 0 | 0 | 0.58 |
| % of standard infus. rate | 4 | 22% | 15% | 8% | 2% | 0% | 0% | 0% | 0% | 0% | 0% | |
| infusion rate in mcg/kg/h | | 6.61 | 4.34 | 2.02 | 0.39 | 0 | 0 | 0 | 0 | 0 | 0 | |
| daily dose in mg/kg | | 0.16 | 0.10 | 0.05 | 0.01 | 0 | 0 | 0 | 0 | 0 | 0 | 0.32 |
| % of standard infus. rate | 5 | 18% | 14% | 8% | 4% | 0% | 0% | 0% | 0% | 0% | 0% | |
| infusion rate in mcg/kg/h | | 5.41 | 4.05 | 2.02 | 0.78 | 0 | 0 | 0 | 0 | 0 | 0 | |
| daily dose in mg/kg | | 0.13 | 0.10 | 0.05 | 0.02 | 0 | 0 | 0 | 0 | 0 | 0 | 0.29 |
| % of standard infus. rate | 6 | 0% | 0% | 0% | 0% | 0% | 0% | 0% | 0% | 0% | 0% | |
| infusion rate in mcg/kg/h | | 0 | 0 | 0 | 0 | 0 | 0 | 0 | 0 | 0 | 0 | |
| daily dose in mg/kg | | 0 | 0 | 0 | 0 | 0 | 0 | 0 | 0 | 0 | 0 | 0.00 |

The invention claimed is:

1. A method for treating a patient with a GD2 positive cancer in a manner such that a side effect of pain is substantially reduced in the patient during treatment comprising administering a preparation comprising a chimeric anti-GD2 antibody, wherein the chimeric anti-GD2 antibody is ch14.18/CHO or ch14.18/SP2/0, to the patient as a continuous intravenous infusion over 24 hours per day, wherein the preparation is administered to the patient in a daily dose of 1 to 25 mg/m$^2$ of the chimeric anti-GD2 antibody and in a dose of 50 to 150 mg/m$^2$/cycle of the chimeric anti-GD2 antibody, and wherein a side effect of pain is substantially reduced compared to a non-continuous infusion schedule of the preparation comprising the chimeric anti-GD2 antibody.

2. The method of claim 1, wherein the preparation is administered to the patient in a dose of 10 mg/m$^2$/day of the chimeric anti-GD2 antibody for 10 consecutive days or in a dose of 15, 20, or 25 mg/m$^2$/day of the chimeric anti-GD2 antibody for 4 consecutive days.

3. The method of claim 1, wherein the chimeric anti-GD2 antibody is ch14.18/CHO.

4. The method of claim 1, wherein the chimeric anti-GD2 antibody is ch14.18/SP2/0.

5. The method of claim 1, wherein the preparation comprising the chimeric anti-GD2 antibody is administered to the patient for 2 or more treatment cycles.

6. The method of claim 1, wherein the preparation comprising the chimeric anti-GD2 antibody is APN311 and is administered to the patient in a dose of 10 mg/m$^2$/day of the chimeric anti-GD2 antibody for 10 consecutive days for 2 or more treatment cycles.

7. The method of claim 1, wherein the chimeric anti-GD2 antibody is ch14.18/SP2/0 and is administered to the patient in a dose of 15, 20, or 25 mg/m$^2$/day of the chimeric anti-GD2 antibody for 4 consecutive days for 2 or more treatment cycles.

8. The method of claim 1, wherein the administration of the preparation comprising the chimeric anti-GD2 antibody is preceded and/or accompanied by the administration of IL-2 and/or GM-CSF or another cytokine.

9. The method of claim 1, wherein the administration period of the preparation comprising the chimeric anti-GD2 antibody is followed by an administration of isotretinoin or another retinoid.

10. The method of claim 1, further comprising administering morphine and/or an analgesic to the patient.

11. The method of claim 10, wherein a daily morphine dose administered during one or more days of continuous intravenous infusion of the preparation comprising the chimeric anti-GD2 antibody and/or of all morphine treatment days is lower than the daily morphine dose during non-continuous administration of the preparation comprising the chimeric anti-GD2 antibody.

12. The method of claim 10, wherein morphine is administered on some but not all days on which the preparation comprising the chimeric anti-GD2 antibody is administered.

13. The method of claim 10, wherein a morphine dose per treatment cycle administered during one or more treatment cycles comprising the continuous intravenous infusion of the preparation comprising the chimeric anti-GD2 antibody is lower than a standard morphine dose per treatment cycle in a non-continuous infusion schedule of the preparation comprising the chimeric anti-GD2 antibody.

14. The method of claim 10, wherein a morphine dose of the overall treatment time is lower than a standard morphine dose of the overall treatment time in a non-continuous infusion schedule of the preparation comprising the chimeric anti-GD2 antibody.

15. The method of claim 10, wherein a morphine dose administered during one or more hours or days of continuous intravenous infusion of the preparation comprising the chimeric anti-GD2 antibody and/or of all morphine treatment hours or days is lower than 50 mcg/kg/h, or lower than 30 mcg/kg/h.

16. The method of a claim 10, wherein the daily morphine dose administered during one or more days of continuous intravenous infusion of the preparation comprising the chimeric anti-GD2 antibody and/or of all morphine treatment days is lower than 0.9, 0.72, 0.48, 0.38, 0.4375, or 0.205 mg/kg/day.

17. The method of claim 10, wherein a dose of one or more analgesics is reduced within an overall treatment time, within a treatment cycle, during a chimeric anti-GD2 antibody treatment period within a treatment cycle, from one chimeric anti-GD2 antibody treatment day to a next chimeric anti-GD2 antibody treatment day within a treatment cycle, and/or from one treatment cycle to a next treatment cycle.

18. The method of claim 1, wherein the GD2 positive cancer is neuroblastoma, glioblastoma, medulloblastoma, astrocytoma, melanoma, small-cell lung cancer, desmoplastic small round cell tumor, osteosarcoma, rhabdomyosarcoma, or another soft tissue sarcoma.

19. The method of claim 18, wherein the patient suffers from primary refractory or relapsed high risk-neuroblastoma or from minimal residual disease in high-risk neuroblastoma.

* * * * *

SEQUENCE LISTING

<160> NUMBER OF SEQ ID NOS: 8

<210> SEQ ID NO 1
<211> LENGTH: 723
<212> TYPE: DNA
<213> ORGANISM: Artificial
<220> FEATURE:
<223> OTHER INFORMATION: artificial antibody chain

<400> SEQUENCE: 1

```
atggaagccc cagcgcagct tctcttcctc ctgctactct ggctcccaga taccactgga      60
gaaatagtga tgacgcagtc tccagccacc ctgtctgtgt ctccagggga aagagccacc     120
ctctcctgca gatctagtca gagtcttgta caccgtaatg gaaacaccta tttacattgg     180
tacctgcaga agccaggcca gtctccaaag ctcctgattc acaaagtttc caaccgattt     240
tctggggtcc cagacaggtt cagtgcagt ggatcaggga cagatttcac actcaagatc     300
agcagagtgg aggctgagga tctgggagtt tatttctgtt ctcaaagtac acatgttcct     360
ccgctcacgt tcggtgctgg gaccaagctg gagctgaaac gaactgtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
```

```
ctcagcagca cccctgacgct gagcaaagca gactacgaga aacacaaagt ctacgcctgc    660
gaagtcaccc atcagggcct gagctcgccc gtcacaaaga gcttcaacag gggagagtgt    720
tag                                                                   723
```

<210> SEQ ID NO 2
<211> LENGTH: 1389
<212> TYPE: DNA
<213> ORGANISM: Artificial
<220> FEATURE:
<223> OTHER INFORMATION: artificial antibody chain

<400> SEQUENCE: 2

```
atgggatgga cctggatctt tattttaatc ctgtcggtaa ctacaggtgt ccactctgag     60
gtccaactgc tgcagtctgg acctgagctg gagaagcctg gcgcttcagt gatgatatcc    120
tgcaaggctt ctggttcctc attcactggc tacaacatga actgggtgag gcagaacatt    180
ggaaagagcc ttgaatggat tggagctatt gatccttact atggtggaac tagctacaac    240
cagaagttca gggcagggc acattgact gtagacaaat cgtccagcac agcctacatg    300
cacctcaaga gcctgacatc tgaggactct gcagtctatt actgtgtaag cggaatggag    360
tactggggtc aaggaacctc agtcaccgtc tcctcagcct ccaccaaggg cccatcggtc    420 ttcccctgg cacctcctc aagagcacc tctggggca gcggccct gggctgcctg    480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccgt gcccagcacc tgaactcctg gggggaccgt cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaagggca gccccgagaa   1080 ccacaggtgt acaccctgcc cccatcccgg gaggagatga ccaagaacca ggtcagcctg   1140
acctgcctgg tcaaaggctt ctatcccagc gacatcgccg tggagtggga gagcaatggg   1200
cagccggaga acaactacaa gaccacgcct cccgtgctgg actccgacgg ctccttcttc   1260
ctctatagca agctcaccgt ggacaagagc aggtggcagc aggggaacgt cttctcatgc   1320
tccgtgatgc atgaggctct gcacaaccac tacacgcaga agagcctctc cctgtccccg   1380
ggtaaatga                                                           1389
```

<210> SEQ ID NO 3
<211> LENGTH: 240
<212> TYPE: PRT
<213> ORGANISM: Artificial
<220> FEATURE:
<223> OTHER INFORMATION: artificial antibody chain

<400> SEQUENCE: 3

```
Met Glu Ala Pro Ala Gln Leu Leu Phe Leu Leu Leu Leu Trp Leu Pro
  1               5                  10                  15

Asp Thr Thr Gly Glu Ile Val Met Thr Gln Ser Pro Ala Thr Leu Ser
                 20                  25                  30
```

Val Ser Pro Gly Glu Arg Ala Thr Leu Ser Cys Arg Ser Ser Gln Ser
         35                  40                  45

Leu Val His Arg Asn Gly Asn Thr Tyr Leu His Trp Tyr Leu Gln Lys
 50                  55                  60

Pro Gly Gln Ser Pro Lys Leu Leu Ile His Lys Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Leu Gly Val Tyr Phe
                100                 105                 110

Cys Ser Gln Ser Thr His Val Pro Pro Leu Thr Phe Gly Ala Gly Thr
            115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 4
<211> LENGTH: 462
<212> TYPE: PRT
<213> ORGANISM: Artificial
<220> FEATURE:
<223> OTHER INFORMATION: artificial antibody chain

<400> SEQUENCE: 4

Met Gly Trp Thr Trp Ile Phe Ile Leu Ile Leu Ser Val Thr Thr Gly
 1               5                  10                  15

Val His Ser Glu Val Gln Leu Leu Gln Ser Gly Pro Glu Leu Glu Lys
             20                  25                  30

Pro Gly Ala Ser Val Met Ile Ser Cys Lys Ala Ser Gly Ser Ser Phe
         35                  40                  45

Thr Gly Tyr Asn Met Asn Trp Val Arg Gln Asn Ile Gly Lys Ser Leu
 50                  55                  60

Glu Trp Ile Gly Ala Ile Asp Pro Tyr Tyr Gly Thr Ser Tyr Asn
 65                  70                  75                  80

Gln Lys Phe Lys Gly Arg Ala Thr Leu Thr Val Asp Lys Ser Ser Ser
                 85                  90                  95

Thr Ala Tyr Met His Leu Lys Ser Leu Thr Ser Glu Asp Ser Ala Val
                100                 105                 110

Tyr Tyr Cys Val Ser Gly Met Glu Tyr Trp Gly Gln Gly Thr Ser Val
            115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

```
Val Lys Asp Tyr Phe Pro Glu Pro Val Thr Val Ser Trp Asn Ser Gly
            165                 170                 175
Ala Leu Thr Ser Gly Val His Thr Phe Pro Ala Val Leu Gln Ser Ser
        180                 185                 190
Gly Leu Tyr Ser Leu Ser Ser Val Val Thr Val Pro Ser Ser Ser Leu
    195                 200                 205
Gly Thr Gln Thr Tyr Ile Cys Asn Val Asn His Lys Pro Ser Asn Thr
210                 215                 220
Lys Val Asp Lys Arg Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Glu Glu Met Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
    450                 455                 460

<210> SEQ ID NO 5
<211> LENGTH: 720
<212> TYPE: DNA
<213> ORGANISM: Artificial
<220> FEATURE:
<223> OTHER INFORMATION: artificial antibody chain

<400> SEQUENCE: 5
atgaagttgc ctgttaggct gttggtgctg atgttctgga ttcctgcttc cttaagcgac    60
gtggtgatga cccagacccc cctgtccctg cccgtgaccc ccggcgagcc cgcctccatc   120
tcctgcagat ctagtcagag tcttgtacac cgtaatggaa acacctattt acattggtac   180
ctgcagaagc caggccagtc tccaaagctc ctgattcaca agtttccaa ccgattttct    240 ggggtcccag acaggttcag tggcagtgga tcagggacag atttcacact caagatcagc   300
agagtggagg ctgaggatct gggagtttat ttctgttctc aaagtacaca tgttcctccg   360
```

```
ctcacgttcg gtgctgggac caagctggag ctgaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct caacagggg agagtgttag    720
```

<210> SEQ ID NO 6
<211> LENGTH: 1788
<212> TYPE: DNA
<213> ORGANISM: Artificial
<220> FEATURE:
<223> OTHER INFORMATION: artificial antibody chain

<400> SEQUENCE: 6

```
atgaagttgc ctgttaggct gttggtgctg atgttctgga ttcctgcttc cttaagcgag     60
gtgcagctgg tgcagtccgg cgccgaggtg agaagcccg cgcctccgt gaagatctcc    120 tgcaaggcct ccggctcctc cttcaccggc tacaacatga actgggtgcg ccagaacatc    180
ggcaagtccc tggagtggat cggcgccatc gaccctact acggcggcac ctcctacaac    240
cagaagttca agggccgcgc caccctgacc gtggacaagt ccacctccac cgcctacatg    300
cacctgaagt ccctgcgctc cgaggacacc gccgtgtact actgcgtgtc cggcatggag    360
tactggggcc agggcacctc cgtgaccgtg tcctccgcct ccaccaaggg cccatcggtc    420
ttccccctgg caccctcctc caagagcacc tctgggggca gcggccct gggctgcctg    480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccgt gcccagcacc tgaactcctg gggggaccgt cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaagggca gccccgagaa   1080 ccacaggtgt acaccctgcc cccatcccgg gaggagatga ccaagaacca ggtcagcctg   1140
acctgcctgg tcaaaggctt ctatcccagc gacatcgccg tggagtggga gagcaatggg   1200
cagccggaga acaactacaa gaccacgcct cccgtgctgg actccgacgg ctccttcttc   1260
ctctatagca agctcaccgt ggacaagagc aggtggcagc aggggaacgt cttctcatgc   1320
tccgtgatgc atgaggctct gcacaaccac tacacgcaga agagcctctc cctgtccccg   1380
ggtaaagccc aacttcaag ttctacaaag aaaacacagc tgcaactgga gcatctcctg   1440
ctggatctcc agatgattct gaatggaatt aacaactaca gaatcccaa actcaccagg   1500 atgctcacat tcaagttcta catgcccaag aaggccacag agctcaaaca tctccagtgt   1560
ctagaggagg aactcaaacc tctggaggaa gtgctaaacc tcgctcagag caaaaacttc   1620
cacttaagac ctagggactt aatcagcaat atcaacgtaa tagttctgga actaaaggga   1680
```

```
tccgaaacaa cattcatgtg tgaatatgct gatgagacag caaccattgt agaatttctg    1740
aacagatgga ttacctttg tcaaagcatc atctcaacac taacttga                  1788
```

<210> SEQ ID NO 7
<211> LENGTH: 239
<212> TYPE: PRT
<213> ORGANISM: Artificial
<220> FEATURE:
<223> OTHER INFORMATION: artificial antibody chain

<400> SEQUENCE: 7

Met Lys Leu Pro Val Arg Leu Leu Val Leu Met Phe Trp Ile Pro Ala
1               5                   10                  15

Ser Leu Ser Asp Val Val Met Thr Gln Thr Pro Leu Ser Leu Pro Val
            20                  25                  30

Thr Pro Gly Glu Pro Ala Ser Ile Ser Cys Arg Ser Ser Gln Ser Leu
        35                  40                  45

Val His Arg Asn Gly Asn Thr Tyr Leu His Trp Tyr Leu Gln Lys Pro
    50                  55                  60

Gly Gln Ser Pro Lys Leu Leu Ile His Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Pro Leu Thr Phe Gly Ala Gly Thr Lys
        115                 120                 125

Leu Glu Leu Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 8
<211> LENGTH: 595
<212> TYPE: PRT
<213> ORGANISM: Artificial
<220> FEATURE:
<223> OTHER INFORMATION: artificial antibody chain

<400> SEQUENCE: 8

Met Lys Leu Pro Val Arg Leu Leu Val Leu Met Phe Trp Ile Pro Ala
1               5                   10                  15

Ser Leu Ser Glu Val Gln Leu Val Gln Ser Gly Ala Glu Val Glu Lys
            20                  25                  30

Pro Gly Ala Ser Val Lys Ile Ser Cys Lys Ala Ser Gly Ser Ser Phe
        35                  40                  45

Thr Gly Tyr Asn Met Asn Trp Val Arg Gln Asn Ile Gly Lys Ser Leu

```
                50                  55                  60
Glu Trp Ile Gly Ala Ile Asp Pro Tyr Tyr Gly Gly Thr Ser Tyr Asn
 65                  70                  75                  80

Gln Lys Phe Lys Gly Arg Ala Thr Leu Thr Val Asp Lys Ser Thr Ser
                 85                  90                  95

Thr Ala Tyr Met His Leu Lys Ser Leu Arg Ser Glu Asp Thr Ala Val
                100                 105                 110

Tyr Tyr Cys Val Ser Gly Met Glu Tyr Trp Gly Gln Gly Thr Ser Val
            115                 120                 125

Thr Val Ser Ser Ala Ser Thr Lys Gly Pro Ser Val Phe Pro Leu Ala
        130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ala Pro
450                 455                 460

Thr Ser Ser Ser Thr Lys Lys Thr Gln Leu Gln Leu Glu His Leu Leu
465                 470                 475                 480
```

```
Leu Asp Leu Gln Met Ile Leu Asn Gly Ile Asn Asn Tyr Lys Asn Pro
            485                 490                 495
Lys Leu Thr Arg Met Leu Thr Phe Lys Phe Tyr Met Pro Lys Lys Ala
            500                 505                 510
Thr Glu Leu Lys His Leu Gln Cys Leu Glu Glu Glu Leu Lys Pro Leu
        515                 520                 525
Glu Glu Val Leu Asn Leu Ala Gln Ser Lys Asn Phe His Leu Arg Pro
        530                 535                 540
Arg Asp Leu Ile Ser Asn Ile Asn Val Ile Val Leu Glu Leu Lys Gly
545                 550                 555                 560
Ser Glu Thr Thr Phe Met Cys Glu Tyr Ala Asp Glu Thr Ala Thr Ile
                565                 570                 575
Val Glu Phe Leu Asn Arg Trp Ile Thr Phe Cys Gln Ser Ile Ile Ser
            580                 585                 590
Thr Leu Thr
        595
```